United States Patent
Glimcher et al.

(10) Patent No.: US 8,293,477 B2
(45) Date of Patent: Oct. 23, 2012

(54) METHODS FOR MODULATING BONE FORMATION AND MINERALIZATION BY MODULATING KRC ACTIVITY

(75) Inventors: Laurie H. Glimcher, West Newton, MA (US); Dallas C. Jones, Brookline, MA (US); Marc Wein, Brookline, MA (US)

(73) Assignee: Cornell University, Itacha, NY (US)

( * ) Notice: Subject to any disclaimer, the term of this patent is extended or adjusted under 35 U.S.C. 154(b) by 811 days.

(21) Appl. No.: 11/918,503

(22) PCT Filed: Apr. 14, 2006

(86) PCT No.: PCT/US2006/014295
§ 371 (c)(1),
(2), (4) Date: Feb. 23, 2009

(87) PCT Pub. No.: WO2006/113559
PCT Pub. Date: Oct. 26, 2006

(65) Prior Publication Data
US 2009/0318338 A1 Dec. 24, 2009

Related U.S. Application Data

(60) Provisional application No. 60/671,619, filed on Apr. 15, 2005.

(51) Int. Cl.
*C12Q 1/00* (2006.01)
*C12Q 1/68* (2006.01)
(52) U.S. Cl. .................. 435/6.13; 435/7.21; 435/69.1
(58) Field of Classification Search .................. None
See application file for complete search history.

(56) References Cited

U.S. PATENT DOCUMENTS

| 2002/0022021 A1 | 2/2002 | Emerson |
| 2004/0191220 A1 | 9/2004 | Einat et al. |
| 2010/0204053 A1* | 8/2010 | Glimcher ............ 506/9 |

FOREIGN PATENT DOCUMENTS

| WO | WO-2004/060304 A2 | 7/2004 |
| WO | WO-2005/001482 A1 | 1/2005 |
| WO | WO-2005/042726 A2 | 5/2005 |

OTHER PUBLICATIONS

Affolter, et al., "Nuclear interpretation of Dpp signaling in *Drosophila*," *EMBO J.*, vol. 20(13):3298-305 (2001).
Allen, et al., "Developmental anomalies and neoplasia in animals and cells deficient in the large zinc finger protein KRC," *Genes Chromosomes Cancer*, vol. 35(4):287-98 (2002).
Allen, et al., "Downregulation of KRC induces proliferation, anchorage independence, and mitotic cell death in HeLa cells," *Exp Cell Res.*, vol. 260(2):346-56 (2000).
Allen, Carl E. et al., "KRC controls cell growth by regulating the transcription of c-myc," Presented at the American Society of Biochemistry and Molecular Biology Annual Meeting, Washington, D.C., p. A1391, Abstract No. 473 (1998).
Allen, et al., "The kappa B transcriptional enhancer motif and signal sequences of V(D)J recombination are targets for the zinc finger protein HIVEP3/KRC: a site selection amplification binding study," *BMC Immunol.*, vol. 22;3(1):10 (2002).
Alliston, Tamara et al., "TGF-β-induced repression of CBFA1 by Smad3 decreases cbfa1 and osteocalcin expression and inhibits osteoblast differentiation," *The EMBO Journal*, vol. 20(9):2254-2272 (2001).
Anders, Hans-Joachim et al., "Murine Models of Renal Disease: Possibilities and Problems in Studies Using Mutant Mice," *Exp. Nephrol.*, vol. 8:181-193 (2000).
Angel P, et al., "Phorbol ester-inducible genes contain a common cis element recognized by a TPA-modulated trans-acting factor," *Cell*, vol. 49(6):729-39 (1987).
Arch, et al., "Tumor necrosis factor receptor-associated factors (TRAFs)—a family of adapter proteins that regulates life and death," *Genes Dev.*, vol. 12(18):2821-30 (1998).
Arias, et al., "Activation of cAMP and mitogen responsive genes relies on a common nuclear factor," *Nature*, vol. 370(6486):226-9 (1994).
Arora, et al., "The *Drosophila schnurri* gene acts in the Dpp/TGF beta signaling pathway and encodes a transcription factor homologous to the human MBP family," *Cell*, vol. 81(5):781-90 (1995).
Bachmeyer, et al., "Regulation by phosphorylation of the zinc finger protein KRC that binds the kappaB motif and V(D)J recombination signal sequences," *Nucleic Acids Res.*, vol. 27(2):643-8 (1999).
Behre, et al., "C-Jun is a JNK-independent coactivator of the PU.1 transcription factor," *J. Biol. Chem.*, vol. 274(8):4939-46 (1999).
Behrens, et al., "Jun N-terminal kinase 2 modulates thymocyte apoptosis and T cell activation through c-Jun and nuclear factor of activated T cell (NF-AT)," *Proc. Natl. Acad. Sci. USA*, vol. 98(4):1769-74 (2001).
Bianchi, et al., "Integrin LFA-1 interacts with the transcriptional co-activator JAB1 to modulate AP-1 activity," *Nature*, vol. 404(6778):617-21 (2000).
Binetruy, et al., "Ha-Ras augments c-Jun activity and stimulates phosphorylation of its activation domain," *Nature*, vol. 351(6322):122-7 (1991).
Bishop, Jo, "Chromosomal insertion of foreign DNA," *Reprod. Nutr. Dev.*, vol. 36:607-618 (1996).
Blokzijl, Andries et al., "Physical and Functional Interaction between GATA-3 and Smad3 Allows TGF-β Regulation of GATA Target Genes," *Current Biology*, vol. 12:35-45 (2002).

(Continued)

*Primary Examiner* — David Romeo
(74) *Attorney, Agent, or Firm* — Nelson Mullins Riley & Scarborough LLP; Debra J. Milasincic, Esq.

(57) ABSTRACT

This invention demonstrates that KRC molecules have multiple important functions as modulating agents in regulating a wide variety of cellular processes including bone formation and mineralization. TGF-β signaling in osteoblasts promotes the formation of a multimeric complex between KRC, Runx2, Smad3, and the E3 ubiquitin ligase, WWP1 which inhibits Runx2 function due to the ability of WWP1 to promote Runx2 polyubiquitination and proteasome-dependent degradation. Furthermore, KRC and WWP1 form a complex with RSK2 which promotes RSK2 phosphorylation and inhibits RSK2 function due to the ability of WWP 1 to promote RSK2 ubiquitination. Methods for identifying modulators of KRC activity are provided. Methods for modulating an immune response, bone formation and mineralization, and KRC-associated disorders using agents that modulate KRC expression and/or activity are also provided.

9 Claims, No Drawings

OTHER PUBLICATIONS

Borden, et al., "The solution structure of the RING finger domain from the acute promyelocytic leukaemia proto-oncoprotein PML," *EMBO J.*, vol. 14(7):1532-41 (1995).

Bork, Peer, "Powers and Pitfalls in Sequence Analysis: The 70% Hurdle," *Genome Research*, vol. 10:398-400 (2000).

Cameron, Ewan R., "Recent Advances in Transgenic Technology," *Molecular Biotechnology*, vol. 7:253-265 (1997).

Cao, et al., "TRAF6 is a signal transducer for interleukin-1," Nature, vol. 383(6599):443-6 (1996).

Castellanos, et al., "Expression of the leukocyte early activation antigen CD69 is regulated by the transcription factor AP-1," *J. Immunol.*, vol. 159(11):5463-73 (1997).

Claret, et al., "A new group of conserved coactivators that increase the specificity of AP-1 transcription factors," *Nature*, vol. 383(6599):453-7 (1996).

Cleland, Jeffrey L. et al., "Emerging protein delivery methods," *Current Opinion in Biotechnology*, vol. 12:212-219 (2001).

Cohn, et al., "Characterization of Sp1, AP-1, CBF and KRC binding sites and minisatellite DNA as functional elements of the metastasis-associated mts1/S100A4 gene intronic enhancer," *Nucleic Acids Res.*, vol. 29(16):3335-46 (2001).

Daga, Andrea et al., "Patterning of cells in the *Drosophila* eye by Lozenge, which shares homologous domains with AML1," *Genes & Development*, vol. 10:1194-1205 (1996).

Dai, et al., "The zinc finger protein schnurri acts as a Smad partner in mediating the transcriptional response to decapentaplegic," *Dev. Biol.*, vol. 227(2):373-87 (2000).

Deng, et al., "c-Fos transcriptional activity stimulated by H-Ras-activated protein kinase distinct from JNK and ERK," *Nature*, vol. 371(6493):171-5 (1994).

Denning, C. et al., "Deletion of the α(1,3)galactosyl transferase (*GGTA1*) gene and the prion protein (*PrP*) gene in sheep," *Nature Biotechnology*, vol. 19:559-562 (2001).

Deonarain, Mahendra P., "Ligand-targeted receptor-mediated vectors for gene delivery," *Exp. Opin. Ther. Patents*, vol. 8(1):53-69 (1998).

Derynck, Rik et al., "Smads: Transcriptional Activators of TGF-β Responses," *Cell*, vol. 95:737-740 (1998).

Doerks, Tobias et al., "Protein annotation: detective work for function prediction," *TIG*, vol. 14(6):248-250 (1998).

Dong, et al., "JNK is required for effector T-cell function but not for T-cell activation," *Nature*, vol. 405(6782):91-4 (2000).

Dumitru, et al., "TNF-alpha induction by LPS is regulated post-transcriptionally via a Tpl2/ERK-dependent pathway," *Cell*, vol. 103(7):1071-83 (2000).

Durand, et al., "A 275 basepair fragment at the 5' end of the interleukin 2 gene enhances expression from a heterologous promoter in response to signals from the T cell antigen receptor," *J. Exp. Med.*, vol. 165(2):395-407 (1987).

Eck, Stephen L. et al., "Gene-Based Therapy," *Goodman & Gilman's The Pharmacological Basis of Therapeutics*, Ninth Edition, McGraw-Hill, Chpt. 5, pp. 77-101 (1996).

Gerlai, Robert, "Gene-targeting studies of mammalian behavior: is is the mutation or the background genotype," *Trends Neurosci.*, vol. 19:177-181 (1996).

Ghosh, et al., "NF-KappaB and Rel Proteins: Evolutionarily conserved mediators of immune responses," Annu. Rev. Immunol., vol. 16:226-260 (1998).

Glimcher, Laurie H. et al., "Control of Postnatal Bone Mass by the Zinc Finger Adapter Protein Schnurri-3," *Ann. N.Y. Acad. Sci.*, vol. 1116:174-181 (2007).

Górecki, Dariusz C., "Prospects and problems of gene therapy: an update," *Expert Opinion Emerging Drugs*, vol. 6(2):187-198 (2001).

Grieder, et al., "Schnurri is required for *Drosophila* Dpp signaling and encodes a zinc finger protein similar to the mammalian transcription factor PRDII-BF1," *Cell*, vol. 81(5):791-800 (1995).

Hicar, et al., "Embryonic expression and regulation of the large zinc finger protein KRC," *Genesis*, vol. 33(1):8-20 (2002).

Hicar, et al., "Structure of the human zinc finger protein HIVEP3: molecular cloning, expression, exon-intron structure, and comparison with paralogous genes HIVEP1 and HIVEP2," *Genomics*, vol. 71(1):89-100 (2001).

Himes, et al., "High mobility group protein I(Y) is required for function and for c-Rel binding to CD28 response elements within the GM-CSF and IL-2 promoters," Immunity, vol. 5(5):479-89 (1996).

Hjelmsoe, et al., "The kappaB and V(D)J recombination signal sequence binding protein KRC regulates transcription of the mouse metastasis-associated gene S100A4/mts1," *J. Biol. Chem.*, vol. 275(2):913-20 (2000).

Houdebine, Louis-Marie, "Production of pharmaceutical proteins from transgenic animals," *Journal of Biotechnology*, vol. 34:269-287 (1994).

Humpherys, David et al., "Epigenetic Instability in ES Cells and Cloned Mice," *Science*, vol. 293:95-97 (2001).

Ip, et al., "Signal transduction by the c-Jun N-terminal kinase (JNK)—from inflammation to development," *Curr. Opin. Cell Biol.*, vol. 10(2):205-19 (1998).

Isakov, et al., "Protein kinase C(theta) in T cell activation," *Annu. Rev. Immunol.*, vol. 20:761-94 (2002).

Jain, et al., "Nuclear factor of activated T cells contains Fos and Jun," *Nature*, vol. 356(6372):801-4 (1992).

Jain, et al., "Transcriptional regulation of the IL-2 gene," *Curr. Opin. Immunol.*, vol. 7(3):333-42 (1995).

Jochum, et al., "AP-1 in mouse development and tumorigenesis," *Oncogene*, vol. 20(19):2401-12 (2001).

Jones, Dallas C. et al., "Regulation of Adult Bone Mass by the Zinc Finger Adapter Protein Schnurri-3," *Science*, vol. 312:1223-1227 (2006).

Jones, Dallas C. et al., "Schnurri-3: A Key Regulator of Postnatal Skeletal Remodeling," *Adv. Exp. Med. Biol.*, Osteoimmunology, Interactions of the Immune and Skeletal Systems, Yongwon Choi, Ed., Springer, vol. 602, Chapter 1, pp. 1-13 (2007).

Jones, Dallas C. et al., "Schnurri-3 is an essential regulator of osteoblast function and adult bone mass," *Ann. Rheum. Dis*, vol. 66(Suppl. III):iii49-iii51 (2007).

Kamei, et al., "A CBP integrator complex mediates transcriptional activation and AP-1 inhibition by nuclear receptors," *Cell*, vol. 85(3):403-14 (1996).

Kappel, Catherine A. et al., "Regulating gene expression in transgenic animals," *Current Opinion in Biotechnology*, vol. 3:548-553 (1992).

Karin, et al., "AP-1 function and regulation," *Curr. Opin. Cell Biol.*, vol. 9(2):240-6 (1997).

Karin M., "The NF-kappa B activation pathway: its regulation and role in inflammation and cell survival," *Cancer J. Sci. Am.*, vol. 4 Suppl 1:S92-9 (1998).

Krishnan, Venkatesh et al., "Parathyroid Hormone Bone Anabolic Action Requires Cbfa1/Runx2-Dependent Signaling," *Molecular Endocrinology*, vol. 17(3):423-435 (2003).

Kuroiwa, Yoshimi et al., "Sequential targeting of the genes encoding immunoglobulin-μ and prion protein in cattle," *Nature Genetics*, vol. 36(7):775-780 (2004).

Lee, et al., "Activating protein-1, nuclear factor-kappaB, and serum response factor as novel target molecules of the cancer-amplified transcription coactivator ASC-2," *Mol. Endocrinol.*, vol. 14(6):915-25 (2000).

Lee, et al., "Steroid receptor coactivator-1 coactivates activating protein-1-mediated transactivations through interaction with the c-Jun and c-Fos subunits," *J. Biol. Chem.*, vol. 273(27):16651-4 (1998).

Lee, et al., "TRAF2 is essential for JNK but not NF-kappaB activation and regulates lymphocyte proliferation and survival," *Immunity*, vol. 7(5):703-13 (1997).

Leppa, et al., "Diverse functions of JNK signaling and c-Jun in stress response and apoptosis," *Oncogene*, vol. 18(45):6158-62 (1999).

Liberati, et al., "Smads bind directly to the Jun family of AP-1 transcription factors," *Proc. Natl. Acad. Sci. USA*, vol. 96(9):4844-9 (1999).

Lindsten, et al., "Regulation of lymphokine messenger RNA stability by a surface-mediated T cell activation pathway," *Science*, vol. 244(4902):339-43 (1989).

Lund, Anders H. et al., "RUNX: A triology of cancer genes," *Cancer Cell*, vol. 1:213-215 (2002).

Lutterbach, B. et al., "Role of the transcription factor AML-1 in acute leukemia and hematopoietic differentiation," *Gene*, vol. 245:223-235 (2000).

Macian, et al., "Transcriptional mechanisms underlying lymphocyte tolerance," *Cell*, vol. 109(6):719-31 (2002).

Mak, et al., "KRC transcripts: identification of an unusual alternative splicing event," *Immunogenetics*, vol. 48(1):32-9 (1998).

Mak, et al., "The V(D)J recombination signal sequence and kappa B binding protein Rc binds DNA as dimers and forms multimeric structures with its DNA ligands," *Nucleic Acids Res.*, vol. 22(3):383-90 (1994).

Massagué, Joan et al., "Transcriptional control by the TGF-β/Smad signaling system," *The EMBO Journal*, vol. 19(8):1745-1754 (2000).

Matunis, et al., "Punt and schnurri regulate a somatically derived signal that restricts proliferation of committed progenitors in the germline," *Development*, vol. 124(21):4383-91 (1997).

Mondino, et al., "Defective transcription of the IL-2 gene is associated with impaired expression of c-Fos, FosB, and JunB in anergic T helper 1 cells," *J. Immunol.*, vol. 157(5):2048-57 (1996).

Moreadith, Randall Wade et al., "Gene targeting in embryonic stem cells: the new physiology and metabolism," *J. Mol. Med.*, vol. 75:208-216 (1997).

Moreau, et al., "Bone-specific expression of the alpha chain of the nascent polypeptide-associated complex, a coactivator potentiating c-Jun-mediated transcription," *Mol. Cell Biol.*, vol. 18(3):1312-21 (1998).

Mullins, John J. et al., "Transgenesis in Nonmurine Species," *Hypertension*, vol. 22(4):630-633 (1993).

Mullins, Linda J. et al., "Molecular Medicine in Genetically Engineered Animals," *J. Clin. Invest.*, vol. 97(7):1557-1560 (1996).

Murphy, et al., "Molecular interpretation of ERK signal duration by immediate early gene products," *Nat. Cell Biol.*, vol. 4(8):556-64 (2002).

Nakano, et al., "TRAF5, an activator of NF-kappaB and putative signal transducer for the lymphotoxin-beta receptor," *J. Biol. Chem.*, vol. 271(25):14661-4 (1996).

Ngo; J. Thomas et al., "Computational Complexity Protein Structure Prediction, and the Levinthal Paradox," *The Protein Folding Problem and Tertiary Structure Prediction*, Chpt. 14, pp. 491-495 (1994).

Oukka, et al., "A mammalian homolog of *Drosophila schnurri*, KRC, regulates TNF receptor-driven responses and interacts with TRAF2," *Mol. Cell.*, vol. 9(1):121-31 (2002).

Oukka, Mohamed et al., "*Schnurri*-3 (KRC) Interacts with c-Jun to Regulate the IL-2 Gene in T Cells," *J. Exp. Med.*, vol. 199(1):15-24 (2004).

Pearson, Helen, "Surviving a knockout blow," *Nature*, vol. 415:8-9 (2002).

Pessah, et al., "C-Jun associates with the oncoprotein Ski and suppresses Smad2 transcriptional activity," *J. Biol. Chem.*, vol. 277(32):29094-100 (2002).

Polejaeva, I.A. et al., "New Advances in Somatic Cell Nuclear Transfer: Application in Transgenesis," *Theriogenology*, vol. 53:117-126 (2000).

Rayter, et al., "p21ras mediates control of IL-2 gene promoter function in T cell activation," *EMBO J.*, vol. 11(12):4549-56 (1992).

Rooney, et al., "Coordinate and cooperative roles for NF-AT and AP-1 in the regulation of the murine IL-4 gene," *Immunity*, vol. 2(5):473-83 (1995).

Rothe, et al., "A novel family of putative signal transducers associated with the cytoplasmic domain of the 75 kDa tumor necrosis factor receptor," *Cell*, vol. 78(4):681-92 (1994).

Rudinger J., "Characteristics of the amino acids as components of a peptide hormone sequence," *Peptide Hormones*, University Park Press, J.A. Parsons, Ed., Chpt. 1, pp. 1-7 (1976).

Rülicke, T. et al., "Germ line transformation of mammals by pronuclear microinjection," *Experimental Physiology*, vol. 85(6):589-601 (2000).

Schalkwyk, L.C. et al., "Interpretation of knockout experiments: the congenic footprint," *Genes, Brain and Behavior*, vol. 6:299-303 (2007).

Shi, Meng-Jiao et al., "CBFα3 (AML2) Is Induced by TGF-β1 to Bind and Activate the Mouse Germline Ig α Promoter," *The Journal of Immunology*, vol. 161:6751-6760 (1998).

Sigmund, Curt D., "Viewpoint: Are Studies in Genetically Altered Mice Out of Control?" *Arterioscler. Thromb. Vasc. Biol.*, vol. 20:1425-1429 (2000).

Skolnick, Jeffrey et al., "From genes to protein structure and function: novel applications of computational approaches in the genomic era," *TibTech*, vol. 18:34-39 (2000).

Smith, Temple F. et al., "The challenges of genome sequence annotation or 'The devil is in the details,'" *Nature Biotechnology*, vol. 15:1222-1223 (1997).

Staehling-Hampton, et al., "A *Drosophila* protein related to the human zinc finger transcription factor PRDII/MBPI/HIV-EP1 is required for dpp signaling," *Development*, vol. 121(10):3393-403 (1995).

Sun, et al., "PKC-theta is required for TCR-induced NF-kappaB activation in mature but not immature T lymphocytes," *Nature*, vol. 404(6776):402-7 (2000).

Szabo, et al., "A novel transcription factor, T-bet, directs Th1 lineage commitment," *Cell*, vol. 100(6):655-69 (2000).

Takagi, et al., "Murine Schnurri-2 is required for positive selection of thymocytes," *Nat. Immunol.*, vol. 2(11):1048-53 (2001).

Torres-Vazquez, et al., "Schnurri is required for dpp-dependent patterning of the *Drosophila* wing," *Dev. Biol.*, vol. 227(2):388-402 (2000).

Torres-Vazquez, et al., "The transcription factor Schnurri plays a dual role in mediating Dpp signaling during embryogenesis," *Development*, vol. 128(9):1657-70 (2001).

Udagawa, et al., "Schnurri interacts with Mad in a Dpp-dependent manner," *Genes Cells*, vol. 5(5):359-69 (2000).

Ullman, Katharine S. et al., "Jun family members are controlled by a calcium-regulated, cyclosporin A-sensitive signaling pathway in activated T lymphocytes," *Genes & Development*, vol. 7(2):188-196 (1993).

Verma, Inder M. et al., "Gene therapy—promises, problems and prospects," *Nature*, vol. 389:239-242 (1997).

Wajant, et al., "TNF receptor associated factors in cytokine signaling," *Cytokine Growth Factor Rev.*, vol. 10(1):15-26 (1999).

Wall, R.J. et al., "Transgenic Dairy Cattle: Genetic Engineering on a Large Scale," *J. Dairy Sci.*, vol. 80(9):2213-2224 (1997).

Wall, R.J., "Transgenic Livestock: Progress and Prospects for the Future," *Thenogenology*, vol. 45:57-68 (1996).

Wallach, et al., "Tumor necrosis factor receptor and Fas signaling mechanisms," *Annu. Rev. Immunol.*, vol. 17:331-67 (1999).

Weiss, et al., "Regulation of c-Jun NH(2)-terminal kinase (Jnk) gene expression during T cell activation," *J. Exp. Med.*, vol. 191(1):139-46 (2000).

Wells, James A. et al., "Additivity of Mutational Effects in Proteins," *Biochemistry*, vol. 29(37):8509-8517 (1990).

Wu, et al., "IEX-1L, an apoptosis inhibitor involved in NF-kappaB-mediated cell survival," *Science*, vol. 281(5379):998-1001 (1998).

Wu, Lai-Chu et al., "The DNA-binding activity ability of HIVEP3/KRC decreases upon activation of V(D)J recombination," *Immunogenetics*, vol. 53:564-571 (2001).

Wu, et al., "The mouse DNA binding protein Rc for the kappa B motif of transcription and for the V(D)J recombination signal sequences contains composite DNA-protein interaction domains and belongs to a new family of large transcriptional proteins," *Genomics*, vol. 35(3):415-24 (1996).

Wu, "ZAS: C2H2 zinc finger proteins involved in growth and development," *Gene Expr.*, vol. 10(4):137-52 (2002).

Yanagimachi, R., "Cloning: experience from the mouse and other animals," *Molecular and Cellular Endocrinology*, vol. 187:241-248 (2002).

Yang, Xiangli et al., "ATF4 Is a Substrate of RSK2 and an Essential Regulator of Osteoblast Biology: Implciation for Coffin-Lowry Syndrome," *Cell*, vol. 117:387-398 (2004).

Yeh, et al., "Early lethality, functional NF-kappaB activation, and increased sensitivity to TNF-induced cell death in TRAF2-deficient mice," *Immunity*, vol. 7(5):715-25 (1997).

Zhang, et al., "Smad3 and Smad4 cooperate with c-Jun/c-Fos to mediate TGF-beta-induced transcription," Nature, vol. 394(6696):909-13 (1998).

Zhang, Ying et al., "Transcriptional Regulation of the Transforming Growth Factor-β-inducible Mouse Germ Line Ig α Constant Region Gene by Functional Cooperation of Smad, CREB, and AML, Family Members," *The Journal of Biological Chemistry*, vol. 275(22):16979-16985 (2000).

International Search Report for Application No. PCT/US04/36641, dated May 18, 2005.

International Preliminary Report on Patentability for Application No. PCT/US2004/036641, dated May 8, 2006.

Cubadda, Yolande et al., "u-shaped encodes a zinc finger protein that regulates the proneural genes achaete and scute during the formation of bristles of *Drosophila*," Genes & Development, vol. 11:3083-3095 (1997).

Ducy, Patricia et al., "A Cbfa1-dependent genetic pathway controls bone formation beyond embryonic development," Genes & Development, vol. 13:1025-1036 (1999).

Guo, Haiwei H. et al., "Protein tolerance to random amino acid change," PNAS, vol. 101(25):9205-9210 (2004).

Haenlin, Marc et al., "Transcriptional activity of Pannier is regulated negatively by heterodimerization of the GATA DNA-binding domain with a cofactor encoded by the u-shaped gene of *Drosophila*," Genes & Development, vol. 11:3096-3108 (1997).

Hult, Karl et al., "Engineered enzymes for improved organic synthesis," Current Opinion in Biotechnology, vol. 14:395-400 (2003).

Lee, Hyun Jun et al., "Characterization of cis-Regulatory Elements and Nuclear Factors Conferring Th2-Specific Expression of the IL-5 Gene: A Role for a GATA-Binding Protein," The Journal of Immunology, vol. 160:2343-2352 (1998).

Liew, Chu Kong et al., "Solution Structures of Two CCHC Zinc Fingers from the FOG Family Protein U-Shaped that Mediate Protein-Protein Interactions," Structure, vol. 8:1157-1166 (2000).

Lowry, Jason A. et al., "Molecular Evolution of the GATA Family of Transcription Factors: Conservation Within the DNA-Binding Domain," Journal of Molecular Evolution, vol. 50:103-115 (2000).

Matthews, Jacqueline et al., "A class of zinc fingers involved in protein-protein interactions. Biophysical characterization of CCHC fingers from Fog and U-shaped," Eur. J. Biochem., vol. 267:1030-1038 (2000).

Patient, Roger K. et al., "The GATA Family (vertebrates and invertebrates)," Current Opinion in Genetics & Development, vol. 12:416-422 (2002).

Ting, Chao-Nan et al., "Transcription factor GATA-3 is required for development of the T-cell lineage," Nature, vol. 384:474-478 (1996).

Tsai, Fong-Ying et al., "Knock-in Mutation of Transcription Factor GATA-3 into the GATA-1 Locus: Partial Rescue of GATA-1 Loss of Function in Erythroid Cells," Developmental Biology, vol. 196:218-227 (1998).

Wu, Lai-Chu et al., "Molecular cloning of a zinc finger protein which binds to the heptamer of the signal sequence of V(D)J recombination," Nucleic Acids Research, vol. 21(22):5067-5073 (1993).

\* cited by examiner

SEQUENCE LISTING

```
<160> NUMBER OF SEQ ID NOS: 41

<210> SEQ ID NO 1
<211> LENGTH: 8546
<212> TYPE: DNA
<213> ORGANISM: Homo sapiens
<220> FEATURE:
<221> NAME/KEY: CDS
<222> LOCATION: (889)..(8106)
```

<400> SEQUENCE: 1

```
acacctgcgc gccggaataa ttcatgaaga aggggctgga tccgtgggtc agagaacaca     60
ggaccagttt gccatcccaa ggccgaaggc ctccctccaa cacagttctc caagctctag    120
aaatctctga cacatcttga ccatgagacc acggctggtt tttggcagga ttcgaggcac    180
aaacccagca gcctcaacct agttcatgga ggagcctcgc ggggtcctgg ccaagcaagc    240
ccgcccctct ggtgggaaga gcggcgccta ggtggagggt ggctgccgta ggagtggaca    300
tgaatgctgg ctttcagaga aacagcgtt tcagttttgg tcatcggaag tggtgccttc     360
agcacagaag aagagcgtga tttctcctcc aaggccgttg atctccaacc agaactaaa    420
ggggagaaga gccaccccca gcatccagcg tggcatctct tgtgccagga ccagggatga    480
ctgggccatg gacacagatg tctccaacct tcaaccgttt gcatagcaca cggggggactc    540
gtgggggcca cctgccactg ccagctgaaa taatacaatg gcaatactga catccttcat    600
gacgttttcc cgacagacat tcaggcagaa agtgctggtg cgtttttctgt ctgcaaagta    660
gagggccatc gctcaccaat agaatagcgt gggccctgat gacctgctcc gagtccactc    720
acagccagtg acacttgcaa aaaactccca aagccgtctt gggtttggct cccacagctc    780
ttgaccaatg tggccaaagc tggacacctc cttgggacac tgggattatt cataaatgca    840
gcccgccctg actctcccctg aatagcatct gaagtctttg tgaaggtc atg gat cct    897
                                                   Met Asp Pro
                                                     1
gaa caa agt gtc aag ggc acc aag aag gct gag gga agt ccc cgg aag    945
Glu Gln Ser Val Lys Gly Thr Lys Lys Ala Glu Gly Ser Pro Arg Lys
          5                  10                  15
cgg ctg acc aaa gga gag gcc att cag acc agt gtt tct tcc agc gtc    993
Arg Leu Thr Lys Gly Glu Ala Ile Gln Thr Ser Val Ser Ser Ser Val
 20                  25                  30                  35
cca tac cca ggc agc ggc aca gct ccg acc caa gag agc ccc gcc caa   1041
Pro Tyr Pro Gly Ser Gly Thr Ala Pro Thr Gln Glu Ser Pro Ala Gln
                 40                  45                  50
gag ctc tta gcc ccg cag ccc ttc ccg ggc ccc tca tca gtt ctt agg   1089
Glu Leu Leu Ala Pro Gln Pro Phe Pro Gly Pro Ser Ser Val Leu Arg
             55                  60                  65
gaa ggc tct cag gag aaa acg ggc cag cag cag aag ccc ccc aaa agg   1137
Glu Gly Ser Gln Glu Lys Thr Gly Gln Gln Gln Lys Pro Pro Lys Arg
         70                  75                  80
ccc ccc atc gaa gca tcc gtc cac atc tca cac gtt ccg cag cac cct   1185
Pro Pro Ile Glu Ala Ser Val His Ile Ser His Val Pro Gln His Pro
     85                  90                  95
ctg aca cca gca ttc atg tcg cct ggc aaa cct gag cat ctc ctg gag   1233
Leu Thr Pro Ala Phe Met Ser Pro Gly Lys Pro Glu His Leu Leu Glu
100                 105                 110                 115
ggg tcc aca tgg caa ctg gtt agc ccc atg aga ctc gga ccc tct ggc   1281
Gly Ser Thr Trp Gln Leu Val Ser Pro Met Arg Leu Gly Pro Ser Gly
                120                 125                 130
tcc ttg ctg gcc cct ggg ctc cat cct cag agc cag ctc ctt cct tcc   1329
Ser Leu Leu Ala Pro Gly Leu His Pro Gln Ser Gln Leu Leu Pro Ser
            135                 140                 145
cac gct tcc atc att ccc ccc gag gac ctt cct gga gtc ccc aaa gtc   1377
His Ala Ser Ile Ile Pro Pro Glu Asp Leu Pro Gly Val Pro Lys Val
        150                 155                 160
ttc gtg cct cgt cct tcc cag gtc tcc ttg aag ccc aca gaa gag gca   1425
Phe Val Pro Arg Pro Ser Gln Val Ser Leu Lys Pro Thr Glu Glu Ala
    165                 170                 175
```

```
cac aag aag gag agg aag ccc cag aag cca ggc aag tac atc tgc cag      1473
His Lys Lys Glu Arg Lys Pro Gln Lys Pro Gly Lys Tyr Ile Cys Gln
180             185                 190                 195 tac tgc agc cgg ccc tgt gcc aag ccc agc gtg ctc cag aag cac att      1521
Tyr Cys Ser Arg Pro Cys Ala Lys Pro Ser Val Leu Gln Lys His Ile
                200                 205                 210 cgc tca cac aca ggt gag agg ccc tac ccc tgc ggc ccc tgt ggc ttc      1569
Arg Ser His Thr Gly Glu Arg Pro Tyr Pro Cys Gly Pro Cys Gly Phe
            215                 220                 225 tcc ttc aag acc aag agt aat ctc tac aag cac agg aag tcc cat gcc      1617
Ser Phe Lys Thr Lys Ser Asn Leu Tyr Lys His Arg Lys Ser His Ala
        230                 235                 240 cac cgc atc aaa gca ggc ctg gcc tca ggc atg ggt ggc gag atg tac      1665
His Arg Ile Lys Ala Gly Leu Ala Ser Gly Met Gly Gly Glu Met Tyr
    245                 250                 255 cca cat ggg ctg gag atg gag cgg atc cct ggg gaa gag ttt gag gag      1713
Pro His Gly Leu Glu Met Glu Arg Ile Pro Gly Glu Glu Phe Glu Glu
260                 265                 270                 275 ccc act gag gga gaa agc aca gat tct gaa gag gag act agt gcc acc      1761
Pro Thr Glu Gly Glu Ser Thr Asp Ser Glu Glu Glu Thr Ser Ala Thr
                280                 285                 290 tct ggt cac cct gca gag ctc tcc cca aga ccc aag cag ccc ctt ctc      1809
Ser Gly His Pro Ala Glu Leu Ser Pro Arg Pro Lys Gln Pro Leu Leu
            295                 300                 305 tcc agc ggg cta tac agc tct ggg agc cac agt tcc agc cac gaa cgc      1857
Ser Ser Gly Leu Tyr Ser Ser Gly Ser His Ser Ser Ser His Glu Arg
        310                 315                 320 tgt tcc ctg tcc cag tcc agc aca gcc cag tca ctc gaa gac ccc cct      1905
Cys Ser Leu Ser Gln Ser Ser Thr Ala Gln Ser Leu Glu Asp Pro Pro
    325                 330                 335 cca ttt gtg gaa ccc tca tct gag cac ccc ctg agc cat aaa cct gaa      1953
Pro Phe Val Glu Pro Ser Ser Glu His Pro Leu Ser His Lys Pro Glu
340                 345                 350                 355 gac acc cac acg att aag cag aag ctg gcc ctc cgc tta agc gag agg      2001
Asp Thr His Thr Ile Lys Gln Lys Leu Ala Leu Arg Leu Ser Glu Arg
                360                 365                 370 aag aag gtg atc gat gag cag gcg ttt ctg agc cca ggc agc aaa ggg      2049
Lys Lys Val Ile Asp Glu Gln Ala Phe Leu Ser Pro Gly Ser Lys Gly
            375                 380                 385 agt act gag tct ggg tat ttc tct cgc tcc gag agt gca gag cag cag      2097
Ser Thr Glu Ser Gly Tyr Phe Ser Arg Ser Glu Ser Ala Glu Gln Gln
        390                 395                 400 gtc agc ccc cca aac acc aac gcc aag tcc tac gct gag atc atc ttt      2145
Val Ser Pro Pro Asn Thr Asn Ala Lys Ser Tyr Ala Glu Ile Ile Phe
    405                 410                 415 ggc aag tgt ggg cga ata gga cag cgg acc gcc atg ctg aca gcc acc      2193
Gly Lys Cys Gly Arg Ile Gly Gln Arg Thr Ala Met Leu Thr Ala Thr
420                 425                 430                 435 tcc acc cag ccc ctc ctg ccc ctc tcc acc gaa gac aag ccc agc ctg      2241
Ser Thr Gln Pro Leu Leu Pro Leu Ser Thr Glu Asp Lys Pro Ser Leu
                440                 445                 450 gtg cct ttg tct gta ccc cgg acg cag gtg atc gag cac atc acg aag      2289
Val Pro Leu Ser Val Pro Arg Thr Gln Val Ile Glu His Ile Thr Lys
            455                 460                 465 ctc atc acc atc aac gag gcc gtg gtg gac acc agt gag atc gac agc      2337
Leu Ile Thr Ile Asn Glu Ala Val Val Asp Thr Ser Glu Ile Asp Ser
        470                 475                 480 gtg aag cca agg cgg agc tca ctg tcc agg cgc agc agc atg gag tcc      2385
Val Lys Pro Arg Arg Ser Ser Leu Ser Arg Arg Ser Ser Met Glu Ser
    485                 490                 495
```

```
cca aaa tcc agc ctc tac cgg gag ccc ctg tca tcc cac agt gag aaa    2433
Pro Lys Ser Ser Leu Tyr Arg Glu Pro Leu Ser Ser His Ser Glu Lys
500             505                 510                 515 acc aag cct gaa caa tca ctg ctg agc ctc cag cac ccg ccc agt acc    2481
Thr Lys Pro Glu Gln Ser Leu Leu Ser Leu Gln His Pro Pro Ser Thr
            520                 525                 530 gcc ccc cct gtg cct ctc ctg aga agc cac tca atg cct tct gcc gcc    2529
Ala Pro Pro Val Pro Leu Leu Arg Ser His Ser Met Pro Ser Ala Ala
                535                 540                 545 tgc act atc agc acc ccc cac cac ccc ttc cga ggt agc tac tcc ttc    2577
Cys Thr Ile Ser Thr Pro His His Pro Phe Arg Gly Ser Tyr Ser Phe
            550                 555                 560 gat gac cat atc acc gac tcc gaa gcc ctg agc cgc agc agt cac gtg    2625
Asp Asp His Ile Thr Asp Ser Glu Ala Leu Ser Arg Ser Ser His Val
565             570                 575 ttt acc tcc cac ccc cgg atg ctg aag ccg cag ccg gca atc gaa tta    2673
Phe Thr Ser His Pro Arg Met Leu Lys Pro Gln Pro Ala Ile Glu Leu
580             585                 590                 595 cct ttg gga ggg gaa tac agt tct gag gag cct ggc cca agc agc aaa    2721
Pro Leu Gly Gly Glu Tyr Ser Ser Glu Glu Pro Gly Pro Ser Ser Lys
                600                 605                 610 gac aca gcc tcc aag ccc tcg gac gaa gtg gaa ccc aag gaa agc gag    2769
Asp Thr Ala Ser Lys Pro Ser Asp Glu Val Glu Pro Lys Glu Ser Glu
            615                 620                 625 ctt acc aaa aag acc aag aag ggt ttg aaa aca aag ggg gtg atc tac    2817
Leu Thr Lys Lys Thr Lys Lys Gly Leu Lys Thr Lys Gly Val Ile Tyr
            630                 635                 640 gaa tgt aac ata tgt ggt gct cgg tac aag aaa agg gat aac tac gaa    2865
Glu Cys Asn Ile Cys Gly Ala Arg Tyr Lys Lys Arg Asp Asn Tyr Glu
            645                 650                 655 gcc cac aaa aaa tac tac tgc tca gag ctt cag atc gca aag ccc atc    2913
Ala His Lys Lys Tyr Tyr Cys Ser Glu Leu Gln Ile Ala Lys Pro Ile
660             665                 670                 675 tct gca ggc acc cac aca tct cca gaa gct gaa aag agt cag att gag    2961
Ser Ala Gly Thr His Thr Ser Pro Glu Ala Glu Lys Ser Gln Ile Glu
                680                 685                 690 cat gag ccg tgg tcc caa atg atg cat tac aaa ctg gga acc acc ctg    3009
His Glu Pro Trp Ser Gln Met Met His Tyr Lys Leu Gly Thr Thr Leu
            695                 700                 705 gaa ctc act cca ctg agg aag agg agg aaa gag aag agc ctt ggg gac    3057
Glu Leu Thr Pro Leu Arg Lys Arg Arg Lys Glu Lys Ser Leu Gly Asp
            710                 715                 720 gag gaa gag cca cct gcc ttt gag tcc aca aaa agt cag ttt ggc agc    3105
Glu Glu Glu Pro Pro Ala Phe Glu Ser Thr Lys Ser Gln Phe Gly Ser
725                 730                 735 ccc ggg cca tct gat gct gct cgg aac ctt ccc ctg gag tcc acc aag    3153
Pro Gly Pro Ser Asp Ala Ala Arg Asn Leu Pro Leu Glu Ser Thr Lys
740                 745                 750                 755 tca cca gca gaa cca agt aaa tca gtg ccc tcc ttg gag gga ccc acg    3201
Ser Pro Ala Glu Pro Ser Lys Ser Val Pro Ser Leu Glu Gly Pro Thr
                760                 765                 770 ggc ttc cag cca agg act ccc aag cca ggg tcc ggt tca gaa tca ggg    3249
Gly Phe Gln Pro Arg Thr Pro Lys Pro Gly Ser Gly Ser Glu Ser Gly
                775                 780                 785 aag gag agg aga aca acg tcc aaa gaa att tct gtc atc cag cac acc    3297
Lys Glu Arg Arg Thr Thr Ser Lys Glu Ile Ser Val Ile Gln His Thr
            790                 795                 800 agc tcc ttt gag aaa tct gat tct ctc gag cag ccg agt ggc ttg gaa    3345
Ser Ser Phe Glu Lys Ser Asp Ser Leu Glu Gln Pro Ser Gly Leu Glu
805                 810                 815
```

```
ggg gaa gac aaa cct ctg gcc cag ttc cca tca ccc cca cct gcc cca    3393
Gly Glu Asp Lys Pro Leu Ala Gln Phe Pro Ser Pro Pro Pro Ala Pro
820             825                 830                 835 cac gga cgc tct gct cac tcc ctg cag cct aag ttg gtc cgc cag ccc    3441
His Gly Arg Ser Ala His Ser Leu Gln Pro Lys Leu Val Arg Gln Pro
            840                 845                 850 aac att cag gtt cct gag atc cta gta act gag gag cct gac cgg ccg    3489
Asn Ile Gln Val Pro Glu Ile Leu Val Thr Glu Glu Pro Asp Arg Pro
                855                 860                 865 gac aca gag cca gag ccg ccc cct aag gaa cct gag aag act gag gag    3537
Asp Thr Glu Pro Glu Pro Pro Pro Lys Glu Pro Glu Lys Thr Glu Glu
        870                 875                 880 ttc caa tgg ccc cag cgc agc cag aca ctt gcc cag ctc cca gct gag    3585
Phe Gln Trp Pro Gln Arg Ser Gln Thr Leu Ala Gln Leu Pro Ala Glu
    885                 890                 895 aag gct cca ccc aaa aag aag agg ttg cgc ctg gca gag atg gcc caa    3633
Lys Ala Pro Pro Lys Lys Lys Arg Leu Arg Leu Ala Glu Met Ala Gln
900             905                 910                 915 tca tca ggg gag tcc agc ttc gag tcc tct gtg cct ctg tct cgc agc    3681
Ser Ser Gly Glu Ser Ser Phe Glu Ser Ser Val Pro Leu Ser Arg Ser
            920                 925                 930 ccg agc cag gaa agc aat gtc tct ttg agt ggg tcc agc cgc tca gcc    3729
Pro Ser Gln Glu Ser Asn Val Ser Leu Ser Gly Ser Ser Arg Ser Ala
                935                 940                 945 tcg ttt gag agg gat gac cat ggg aaa gcc gag gcc ccc gat ccc tca    3777
Ser Phe Glu Arg Asp Asp His Gly Lys Ala Glu Ala Pro Asp Pro Ser
        950                 955                 960 tct gac atg cgc ccc aaa ccc ctg ggc acc cac atg ttg act gtc ccc    3825
Ser Asp Met Arg Pro Lys Pro Leu Gly Thr His Met Leu Thr Val Pro
    965                 970                 975 agc cac cac cca cat gcc cga gag atg cgg agg tca gcc tca gag cag    3873
Ser His His Pro His Ala Arg Glu Met Arg Arg Ser Ala Ser Glu Gln
980             985                 990                 995 agc ccc aac gtt tcc cat tct gcc cac atg acc gag aca cgc agc aaa    3921
Ser Pro Asn Val Ser His Ser Ala His Met Thr Glu Thr Arg Ser Lys
            1000                1005                1010 tcc ttt gac tat ggc agc ttg tcc ttg aca ggc cct tct gct cca gcc    3969
Ser Phe Asp Tyr Gly Ser Leu Ser Leu Thr Gly Pro Ser Ala Pro Ala
        1015                1020                1025 cca gtg gct cca cca gcc ggg gag gcc ccg cca gag aga aga aaa tgc    4017
Pro Val Ala Pro Pro Ala Gly Glu Ala Pro Pro Glu Arg Arg Lys Cys
    1030                1035                1040 ttc ttg gtg aga agc ccc tct ctg agc agg cct cca gaa tct gag ttg    4065
Phe Leu Val Arg Ser Pro Ser Leu Ser Arg Pro Pro Glu Ser Glu Leu
1045                1050                1055 gag gtt gcc ccc aag gga aga cag gag agc gaa gaa cca cag ccc tca    4113
Glu Val Ala Pro Lys Gly Arg Gln Glu Ser Glu Glu Pro Gln Pro Ser
1060                1065                1070                1075 tcc agt aaa ccc tct gcc aaa agc tca ttg tcc cag att tcc tct gcg    4161
Ser Ser Lys Pro Ser Ala Lys Ser Ser Leu Ser Gln Ile Ser Ser Ala
            1080                1085                1090 gcc acc tca cat ggt gga ccc cgg gga agg ggc cca ggg cag gac         4209
Ala Thr Ser His Gly Gly Pro Arg Gly Gly Lys Gly Pro Gly Gln Asp
        1095                1100                1105 agg ccc gca ttg ggg ccc act gtg ccc tac aca gaa gca ctg caa gtg    4257
Arg Pro Ala Leu Gly Pro Thr Val Pro Tyr Thr Glu Ala Leu Gln Val
    1110                1115                1120 ttc cac cac ccc gtt gcc cag aca ccc ctg cat gag aag cca tac ctg    4305
Phe His His Pro Val Ala Gln Thr Pro Leu His Glu Lys Pro Tyr Leu
1125                1130                1135
```

```
ccc cca cca gtc tcc ctt ttc tcc ttc cag cat ctc gtg cag cat gag      4353
Pro Pro Pro Val Ser Leu Phe Ser Phe Gln His Leu Val Gln His Glu
1140                1145                1150                1155 cca gga cag tct cca gaa ttc ttc tcc acc cag gcc atg tcc agc ctc      4401
Pro Gly Gln Ser Pro Glu Phe Phe Ser Thr Gln Ala Met Ser Ser Leu
                1160                1165                1170 ctg tcc tca cca tac tcc atg ccc cca ctt cct ccc tcc tta ttt caa      4449
Leu Ser Ser Pro Tyr Ser Met Pro Pro Leu Pro Pro Ser Leu Phe Gln
            1175                1180                1185 gcc cca ccg ctt cct ctc cag cct act gtt ctg cac cca ggc caa ctc      4497
Ala Pro Pro Leu Pro Leu Gln Pro Thr Val Leu His Pro Gly Gln Leu
        1190                1195                1200 cat ctc ccc cag ctc atg cct cac cca gcc aac atc ccc ttc agg caa      4545
His Leu Pro Gln Leu Met Pro His Pro Ala Asn Ile Pro Phe Arg Gln
    1205                1210                1215 ccc cct tcc ttc ctc ccc atg cca tac ccg acc tcc tca gca ctg tct      4593
Pro Pro Ser Phe Leu Pro Met Pro Tyr Pro Thr Ser Ser Ala Leu Ser
1220                1225                1230                1235 tct ggg ttt ttc ctg cct ctg caa tcc cag ttt gca ctt cag ctc cct      4641
Ser Gly Phe Phe Leu Pro Leu Gln Ser Gln Phe Ala Leu Gln Leu Pro
                1240                1245                1250 ggt gat gtg gaa agc cat ctg ccc cag atc aaa acc agc ctg gcc cca      4689
Gly Asp Val Glu Ser His Leu Pro Gln Ile Lys Thr Ser Leu Ala Pro
            1255                1260                1265 ctg gca aca gga agt gct ggc ctc tcc ccc agc caa gag tac agc agt      4737
Leu Ala Thr Gly Ser Ala Gly Leu Ser Pro Ser Gln Glu Tyr Ser Ser
        1270                1275                1280 gac atc cgg cta ccc cct gtg gct ccc cca gcc agc tcc tca gca cct      4785
Asp Ile Arg Leu Pro Pro Val Ala Pro Pro Ala Ser Ser Ser Ala Pro
    1285                1290                1295 aca tca gct cct cca ctg gcc ctg cct gcc tgt cca gac acc atg gtg      4833
Thr Ser Ala Pro Pro Leu Ala Leu Pro Ala Cys Pro Asp Thr Met Val
1300                1305                1310                1315 tcc ctg gtt gtg cct gtc cgt gtt cag acc aat atg ccg tcc tat ggg      4881
Ser Leu Val Val Pro Val Arg Val Gln Thr Asn Met Pro Ser Tyr Gly
                1320                1325                1330 agc gca atg tac acc acc ctt tcc cag atc ttg gtc acc cag tcc caa      4929
Ser Ala Met Tyr Thr Thr Leu Ser Gln Ile Leu Val Thr Gln Ser Gln
            1335                1340                1345 ggc agc tca gca act gtg gca ctt ccc aag ttt gag gaa ccc cca tca      4977
Gly Ser Ser Ala Thr Val Ala Leu Pro Lys Phe Glu Glu Pro Pro Ser
        1350                1355                1360 aag ggg acg act gta tgt ggt gca gat gtg cat gag gtt ggg ccc ggc      5025
Lys Gly Thr Thr Val Cys Gly Ala Asp Val His Glu Val Gly Pro Gly
    1365                1370                1375 cct tct ggg tta agt gaa gag caa agc aga gct ttc cca act cca tac      5073
Pro Ser Gly Leu Ser Glu Glu Gln Ser Arg Ala Phe Pro Thr Pro Tyr
1380                1385                1390                1395 ctg aga gtg cct gtg aca tta cct gaa aga aaa ggc act tcc ctg tca      5121
Leu Arg Val Pro Val Thr Leu Pro Glu Arg Lys Gly Thr Ser Leu Ser
                1400                1405                1410 tca gag agt atc ttg agc ctg gag ggg agt tca tca aca gca ggg gga      5169
Ser Glu Ser Ile Leu Ser Leu Glu Gly Ser Ser Ser Thr Ala Gly Gly
            1415                1420                1425 agc aaa cgt gtc ctt tca cca gct ggc agc ctt gaa ctt acc atg gaa      5217
Ser Lys Arg Val Leu Ser Pro Ala Gly Ser Leu Glu Leu Thr Met Glu
        1430                1435                1440 acc cag cag caa aaa aga gtg aag gag gag gag gct tcc aag gca gat      5265
Thr Gln Gln Gln Lys Arg Val Lys Glu Glu Glu Ala Ser Lys Ala Asp
    1445                1450                1455
```

```
gaa aaa ctt gag ctg gta aaa cca tgc agt gtg gtc ctt acc agc acc      5313
Glu Lys Leu Glu Leu Val Lys Pro Cys Ser Val Val Leu Thr Ser Thr
1460            1465                1470                1475 gag gat ggg aag agg cca gag aaa tcc cac tta ggc aac cag ggc caa      5361
Glu Asp Gly Lys Arg Pro Glu Lys Ser His Leu Gly Asn Gln Gly Gln
        1480                1485                1490 ggc agg agg gag cta gaa atg ctg tcc agc ctg tcc tca gat cca tct      5409
Gly Arg Arg Glu Leu Glu Met Leu Ser Ser Leu Ser Ser Asp Pro Ser
    1495                1500                1505 gac aca aag gaa att cct ccc ctc cct cac cct gca ttg tcc cat ggg      5457
Asp Thr Lys Glu Ile Pro Pro Leu Pro His Pro Ala Leu Ser His Gly
1510                1515                1520 caa gcc cca ggc tca gaa gct ttg aag gaa tat ccc cag cca tct ggc      5505
Gln Ala Pro Gly Ser Glu Ala Leu Lys Glu Tyr Pro Gln Pro Ser Gly
        1525                1530                1535 aaa cct cac cga aga ggg ttg acc cca ctg agc gtg aag aaa gaa gat      5553
Lys Pro His Arg Arg Gly Leu Thr Pro Leu Ser Val Lys Lys Glu Asp
1540                1545                1550                1555 tcc aag gaa caa cct gat ctc ccc tcc ttg gca cct ccg agc tct ctg      5601
Ser Lys Glu Gln Pro Asp Leu Pro Ser Leu Ala Pro Pro Ser Ser Leu
                1560                1565                1570 cct ctg tca gaa acg tcc tcc aga cca gcc aag tca caa gaa ggt acg      5649
Pro Leu Ser Glu Thr Ser Ser Arg Pro Ala Lys Ser Gln Glu Gly Thr
            1575                1580                1585 gac tca aag aag gta ctg cag ttc ccc agc ctc cac aca acc act aat      5697
Asp Ser Lys Lys Val Leu Gln Phe Pro Ser Leu His Thr Thr Thr Asn
        1590                1595                1600 gtc agt tgg tgc tat tta aac tac att aag cca aat cac atc cag cat      5745
Val Ser Trp Cys Tyr Leu Asn Tyr Ile Lys Pro Asn His Ile Gln His
1605                1610                1615 gca gat agg agg tcc tct gtt tac gct ggt tgg tgc ata agt ttg tac      5793
Ala Asp Arg Arg Ser Ser Val Tyr Ala Gly Trp Cys Ile Ser Leu Tyr
1620                1625                1630                1635 aac ccc aac ctt ccg ggg gtt tcc act aaa gct gct ttg tcc ctc ctg      5841
Asn Pro Asn Leu Pro Gly Val Ser Thr Lys Ala Ala Leu Ser Leu Leu
            1640                1645                1650 agg tct aag cag aaa gtg agc aaa gag aca tac acc atg gcc aca gct      5889
Arg Ser Lys Gln Lys Val Ser Lys Glu Thr Tyr Thr Met Ala Thr Ala
        1655                1660                1665 ccg cat cct gag gca gga agg ctt gtg cca tcc agc tcc cgc aag ccc      5937
Pro His Pro Glu Ala Gly Arg Leu Val Pro Ser Ser Ser Arg Lys Pro
    1670                1675                1680 cgc atg aca gag gtt cac ctc cct tca ctg gtt tcc ccg gaa ggc cag      5985
Arg Met Thr Glu Val His Leu Pro Ser Leu Val Ser Pro Glu Gly Gln
1685                1690                1695 aaa gat cta gct aga gtg gag aag gaa gaa gag agg aga ggg gag ccg      6033
Lys Asp Leu Ala Arg Val Glu Lys Glu Glu Glu Arg Arg Gly Glu Pro
1700                1705                1710                1715 gag gag gat gct cct gcc tcc cag aga ggg gag ccg gcg agg atc aaa      6081
Glu Glu Asp Ala Pro Ala Ser Gln Arg Gly Glu Pro Ala Arg Ile Lys
            1720                1725                1730 atc ttc gaa gga ggg tac aaa tca aac gaa gag tat gta tat gtg cga      6129
Ile Phe Glu Gly Gly Tyr Lys Ser Asn Glu Glu Tyr Val Tyr Val Arg
        1735                1740                1745 ggc cgc ggc cga ggg aaa tat gtt tgt gag gag tgt gga att cgc tgc      6177
Gly Arg Gly Arg Gly Lys Tyr Val Cys Glu Glu Cys Gly Ile Arg Cys
    1750                1755                1760 aag aag ccc agc atg ctg aag aaa cac atc cgc acc cac act gac gtc      6225
Lys Lys Pro Ser Met Leu Lys Lys His Ile Arg Thr His Thr Asp Val
1765                1770                1775
```

| | | |
|---|---|---|
| cgg ccc tat gtg tgc aag cac tgt cac ttt gct ttt aaa acc aaa ggg<br>Arg Pro Tyr Val Cys Lys His Cys His Phe Ala Phe Lys Thr Lys Gly<br>1780                       1785                  1790                   1795 | 6273 |
| aat ctg act aag cac atg aag tcg aag gcc cac agc aaa aag tgc caa<br>Asn Leu Thr Lys His Met Lys Ser Lys Ala His Ser Lys Lys Cys Gln<br>                    1800                  1805                   1810 | 6321 |
| gag aca ggg gtg ctg gag gag ctg gaa gcc gaa gaa gga acc agt gac<br>Glu Thr Gly Val Leu Glu Glu Leu Glu Ala Glu Glu Gly Thr Ser Asp<br>1815                       1820                  1825 | 6369 |
| gac ctg ttc cag gac tcg gaa gga cga gag ggt tca gag gct gtg gag<br>Asp Leu Phe Gln Asp Ser Glu Gly Arg Glu Gly Ser Glu Ala Val Glu<br>                    1830                  1835                   1840 | 6417 |
| gag cac cag ttt tcg gac ctg gag gac tcg gac tca gac tca gac ctg<br>Glu His Gln Phe Ser Asp Leu Glu Asp Ser Asp Ser Asp Ser Asp Leu<br>1845                       1850                  1855 | 6465 |
| gac gaa gac gag gat gag gat gag gag gag agc cag gat gag ctg tcc<br>Asp Glu Asp Glu Asp Glu Asp Glu Glu Glu Ser Gln Asp Glu Leu Ser<br>1860                       1865                  1870                   1875 | 6513 |
| aga cca tcc tca gag gcg ccc ccg cct gga cca cat gca ctg cgg<br>Arg Pro Ser Ser Glu Ala Pro Pro Gly Pro Pro His Ala Leu Arg<br>                        1880                  1885                  1890 | 6561 |
| gca gac tcc tca ccc atc ctg ggc cct cag ccc cca gat gcc ccc gcc<br>Ala Asp Ser Ser Pro Ile Leu Gly Pro Gln Pro Pro Asp Ala Pro Ala<br>                    1895                  1900                   1905 | 6609 |
| tct ggc acg gag gcc aca cga ggc agc tcg gtc tcg gaa gct gag cgc<br>Ser Gly Thr Glu Ala Thr Arg Gly Ser Ser Val Ser Glu Ala Glu Arg<br>1910                       1915                  1920 | 6657 |
| ctg aca gcc agc agc tgc tcc atg tcc agc cag agc atg ccg ggc ctc<br>Leu Thr Ala Ser Ser Cys Ser Met Ser Ser Gln Ser Met Pro Gly Leu<br>                    1925                  1930                   1935 | 6705 |
| ccc tgg ctg gga ccg gcc cct ctg ggc tct gtg gag aaa gac aca ggc<br>Pro Trp Leu Gly Pro Ala Pro Leu Gly Ser Val Glu Lys Asp Thr Gly<br>1940                       1945                  1950                   1955 | 6753 |
| tca gcc ttg agc tac aag cct gtg tcc cca aga aga ccg tgg tcc cca<br>Ser Ala Leu Ser Tyr Lys Pro Val Ser Pro Arg Arg Pro Trp Ser Pro<br>                    1960                  1965                   1970 | 6801 |
| agc aaa gaa gca ggc agc cgt cca cca cta gcc cgc aaa cac tcg cta<br>Ser Lys Glu Ala Gly Ser Arg Pro Pro Leu Ala Arg Lys His Ser Leu<br>1975                       1980                  1985 | 6849 |
| acc aaa aac gac tca tct ccc cag cga tgc tcc ccg gcc cga gaa cca<br>Thr Lys Asn Asp Ser Ser Pro Gln Arg Cys Ser Pro Ala Arg Glu Pro<br>                    1990                  1995                   2000 | 6897 |
| cag gcc tca gcc cca agc cca cct ggc ctg cac gtg gac cca gga agg<br>Gln Ala Ser Ala Pro Ser Pro Pro Gly Leu His Val Asp Pro Gly Arg<br>2005                       2010                  2015 | 6945 |
| ggc atg ggc cct ctc cct tgt ggg tct cca aga ctt cag ctg tct cct<br>Gly Met Gly Pro Leu Pro Cys Gly Ser Pro Arg Leu Gln Leu Ser Pro<br>2020                       2025                  2030                   2035 | 6993 |
| ctc acc ctc tgc ccc ctg gga aga gaa ctg gcc cct cga gca cat gtg<br>Leu Thr Leu Cys Pro Leu Gly Arg Glu Leu Ala Pro Arg Ala His Val<br>                    2040                  2045                   2050 | 7041 |
| ctc tcc aaa ctc gag ggt acc acc gac cca ggc ctc ccc aga tac tcg<br>Leu Ser Lys Leu Glu Gly Thr Thr Asp Pro Gly Leu Pro Arg Tyr Ser<br>2055                       2060                  2065 | 7089 |
| ccc acc agg aga tgg tct cca ggt cag gcc gag tca cca cca cgg tca<br>Pro Thr Arg Arg Trp Ser Pro Gly Gln Ala Glu Ser Pro Pro Arg Ser<br>                    2070                  2075                   2080 | 7137 |
| gcg ccg cca ggg aag tgg gcc ttg gct ggg ccg ggc agc ccc tca gcg<br>Ala Pro Pro Gly Lys Trp Ala Leu Ala Gly Pro Gly Ser Pro Ser Ala<br>2085                       2090                  2095 | 7185 |

-continued

| | |
|---|---|
| ggg gag cat ggc cca ggc ttg ggg ctg gcc cca cgg gtt ctc ttc ccg<br>Gly Glu His Gly Pro Gly Leu Gly Leu Ala Pro Arg Val Leu Phe Pro<br>2100                       2105                   2110                 2115 | 7233 |
| ccc gcg cct cta cct cac aag ctc ctc agc aga agc cca gag acc tgc<br>Pro Ala Pro Leu Pro His Lys Leu Leu Ser Arg Ser Pro Glu Thr Cys<br>               2120                   2125                 2130 | 7281 |
| gcc tcc ccg tgg cag aag gcc gag tcc cga agt ccc tcc tgc tca ccc<br>Ala Ser Pro Trp Gln Lys Ala Glu Ser Arg Ser Pro Ser Cys Ser Pro<br>             2135                   2140                 2145 | 7329 |
| ggc cct gct cat cct ctc tcc tcc cga ccc ttc tcc gcc ctc cat gac<br>Gly Pro Ala His Pro Leu Ser Ser Arg Pro Phe Ser Ala Leu His Asp<br>2150                       2155                   2160 | 7377 |
| ttc cac ggc cac atc ctg gcc cgg aca gag gag aac atc ttc agc cac<br>Phe His Gly His Ile Leu Ala Arg Thr Glu Glu Asn Ile Phe Ser His<br>         2165                   2170                 2175 | 7425 |
| ctg cct ctg cac tcc cag cac ttg acc cgt gcc cca tgt ccc ttg att<br>Leu Pro Leu His Ser Gln His Leu Thr Arg Ala Pro Cys Pro Leu Ile<br>2180                       2185                   2190                 2195 | 7473 |
| ccc atc ggt ggg atc cag atg gtg cag gcc cgg cca gga gcc cac ccc<br>Pro Ile Gly Gly Ile Gln Met Val Gln Ala Arg Pro Gly Ala His Pro<br>                   2200                   2205                 2210 | 7521 |
| acc ctg ctg cca ggg ccc acc gca gcc tgg gtc agt ggc ttc tcc ggg<br>Thr Leu Leu Pro Gly Pro Thr Ala Ala Trp Val Ser Gly Phe Ser Gly<br>             2215                   2220                   2225 | 7569 |
| ggt ggc agc gac ctg aca ggg gcc cgg gag gcc cag gag cga ggc cgc<br>Gly Gly Ser Asp Leu Thr Gly Ala Arg Glu Ala Gln Glu Arg Gly Arg<br>         2230                   2235                 2240 | 7617 |
| tgg agt ccc act gag agc tcg tca gcc tcc gtg tcg cct gtg gct aag<br>Trp Ser Pro Thr Glu Ser Ser Ser Ala Ser Val Ser Pro Val Ala Lys<br>2245                       2250                   2255 | 7665 |
| gtc tcc aaa ttc aca ctc tcc tca gag ctg gag ggc agg gac tac ccc<br>Val Ser Lys Phe Thr Leu Ser Ser Glu Leu Glu Gly Arg Asp Tyr Pro<br>2260                       2265                   2270                 2275 | 7713 |
| aag gag agg gag agg acc ggc gga ggc ccg ggc agg cct cct gac tgg<br>Lys Glu Arg Glu Arg Thr Gly Gly Gly Pro Gly Arg Pro Pro Asp Trp<br>                   2280                   2285                 2290 | 7761 |
| aca ccc cat ggg acc ggg gca cct gca gag ccc aca ccc acg cac agc<br>Thr Pro His Gly Thr Gly Ala Pro Ala Glu Pro Thr Pro Thr His Ser<br>               2295                   2300                 2305 | 7809 |
| ccc tgc acc cca ccc gac acc ttg ccc cgg ccg ccc cag gga cgc cgg<br>Pro Cys Thr Pro Pro Asp Thr Leu Pro Arg Pro Pro Gln Gly Arg Arg<br>             2310                   2315                   2320 | 7857 |
| gca gcg cag tcc tgg agc ccc cgc ttg gag tcc ccg cgt gca ccg gcc<br>Ala Ala Gln Ser Trp Ser Pro Arg Leu Glu Ser Pro Arg Ala Pro Ala<br>         2325                   2330                 2335 | 7905 |
| aac ccc gag cct tct gcc acc ccg ccg ctg gac cgc agc agc tct gtg<br>Asn Pro Glu Pro Ser Ala Thr Pro Pro Leu Asp Arg Ser Ser Ser Val<br>2340                       2345                   2350                 2355 | 7953 |
| ggc tgc ctg gca gag gcc tct gcc cgc ttc cca gcc cgg acg agg aac<br>Gly Cys Leu Ala Glu Ala Ser Ala Arg Phe Pro Ala Arg Thr Arg Asn<br>             2360                   2365                   2370 | 8001 |
| ctc tcc ggg gaa tcc agg acc agg cag gac tcc ccc aag ccc tca gga<br>Leu Ser Gly Glu Ser Arg Thr Arg Gln Asp Ser Pro Lys Pro Ser Gly<br>         2375                   2380                 2385 | 8049 |
| agt ggg gag ccc agg gca cat cca cat cag cct gag gac agg gtt ccc<br>Ser Gly Glu Pro Arg Ala His Pro His Gln Pro Glu Asp Arg Val Pro<br>         2390                   2395                 2400 | 8097 |

-continued

```
ccc aac gct tagcctctct ccaactgctt cagcatctgg cttccagtgt        8146
Pro Asn Ala
    2405 ccagcaacag acgtttccag ccactttcct cgaatcatcc cacttcctca gccccatctg 8206 tccctccatc caggagctct cacggcccca tctgttgtac cttcccatgt atgcagttac 8266 ctgtgccttt ttctacacct tttgttgctt aaaagaaac aaacaaatc acatacatac  8326 atttaaaaaa aaaacaacaa cccacgagga gtctgaggct gtgaatagtt tatggttttg 8386 gggaaaggct gatggtgaag cctcctgacc ctccccgctg tggttggcag ccacccaccc 8446 cagaggctgg cagagggaaa ggggtacact gagggagaaa ggaaaaggaa acttcaaaca 8506 atatagaatt aaatgtaaaa ggcagcactc ctgtgtacag                      8546

<210> SEQ ID NO 2
<211> LENGTH: 2406
<212> TYPE: PRT
<213> ORGANISM: Homo sapiens

<400> SEQUENCE: 2

Met Asp Pro Glu Gln Ser Val Lys Gly Thr Lys Lys Ala Glu Gly Ser
 1               5                  10                  15

Pro Arg Lys Arg Leu Thr Lys Gly Glu Ala Ile Gln Thr Ser Val Ser
            20                  25                  30

Ser Ser Val Pro Tyr Pro Gly Gly Thr Ala Pro Thr Gln Glu Ser
        35                  40                  45

Pro Ala Gln Glu Leu Leu Ala Pro Gln Pro Phe Pro Gly Pro Ser Ser
     50                  55                  60

Val Leu Arg Glu Gly Ser Gln Glu Lys Thr Gly Gln Gln Lys Pro
65                  70                  75                  80

Pro Lys Arg Pro Pro Ile Glu Ala Ser Val His Ile Ser His Val Pro
                85                  90                  95

Gln His Pro Leu Thr Pro Ala Phe Met Ser Pro Gly Lys Pro Glu His
            100                 105                 110

Leu Leu Glu Gly Ser Thr Trp Gln Leu Val Ser Pro Met Arg Leu Gly
        115                 120                 125

Pro Ser Gly Ser Leu Leu Ala Pro Gly Leu His Pro Gln Ser Gln Leu
    130                 135                 140

Leu Pro Ser His Ala Ser Ile Ile Pro Pro Glu Asp Leu Pro Gly Val
145                 150                 155                 160

Pro Lys Val Phe Val Pro Arg Pro Ser Gln Val Ser Leu Lys Pro Thr
                165                 170                 175

Glu Glu Ala His Lys Lys Glu Arg Lys Pro Gln Lys Pro Gly Lys Tyr
            180                 185                 190

Ile Cys Gln Tyr Cys Ser Arg Pro Cys Ala Lys Pro Ser Val Leu Gln
        195                 200                 205

Lys His Ile Arg Ser His Thr Gly Glu Arg Pro Tyr Pro Cys Gly Pro
    210                 215                 220

Cys Gly Phe Ser Phe Lys Thr Lys Ser Asn Leu Tyr Lys His Arg Lys
225                 230                 235                 240

Ser His Ala His Arg Ile Lys Ala Gly Leu Ala Ser Gly Met Gly Gly
                245                 250                 255

Glu Met Tyr Pro His Gly Leu Glu Met Glu Arg Ile Pro Gly Glu Glu
            260                 265                 270

Phe Glu Glu Pro Thr Glu Gly Gly Ser Thr Asp Ser Glu Glu Thr
        275                 280                 285
```

```
Ser Ala Thr Ser Gly His Pro Ala Glu Leu Ser Pro Arg Pro Lys Gln
    290                 295                 300

Pro Leu Leu Ser Ser Gly Leu Tyr Ser Ser Gly Ser His Ser Ser Ser
305                 310                 315                 320

His Glu Arg Cys Ser Leu Ser Gln Ser Ser Thr Ala Gln Ser Leu Glu
                325                 330                 335

Asp Pro Pro Pro Phe Val Glu Pro Ser Ser Glu His Pro Leu Ser His
            340                 345                 350

Lys Pro Glu Asp Thr His Thr Ile Lys Gln Lys Leu Ala Leu Arg Leu
        355                 360                 365

Ser Glu Arg Lys Lys Val Ile Asp Glu Gln Ala Phe Leu Ser Pro Gly
    370                 375                 380

Ser Lys Gly Ser Thr Glu Ser Gly Tyr Phe Ser Arg Ser Glu Ser Ala
385                 390                 395                 400

Glu Gln Gln Val Ser Pro Pro Asn Thr Asn Ala Lys Ser Tyr Ala Glu
                405                 410                 415

Ile Ile Phe Gly Lys Cys Gly Arg Ile Gly Gln Arg Thr Ala Met Leu
            420                 425                 430

Thr Ala Thr Ser Thr Gln Pro Leu Leu Pro Leu Ser Thr Glu Asp Lys
        435                 440                 445

Pro Ser Leu Val Pro Leu Ser Val Pro Arg Thr Gln Val Ile Glu His
    450                 455                 460

Ile Thr Lys Leu Ile Thr Ile Asn Glu Ala Val Val Asp Thr Ser Glu
465                 470                 475                 480

Ile Asp Ser Val Lys Pro Arg Arg Ser Ser Leu Ser Arg Arg Ser Ser
                485                 490                 495

Met Glu Ser Pro Lys Ser Ser Leu Tyr Arg Glu Pro Leu Ser Ser His
            500                 505                 510

Ser Glu Lys Thr Lys Pro Glu Gln Ser Leu Leu Ser Leu Gln His Pro
        515                 520                 525

Pro Ser Thr Ala Pro Pro Val Pro Leu Leu Arg Ser His Ser Met Pro
    530                 535                 540

Ser Ala Ala Cys Thr Ile Ser Thr Pro His His Pro Phe Arg Gly Ser
545                 550                 555                 560

Tyr Ser Phe Asp Asp His Ile Thr Asp Ser Glu Ala Leu Ser Arg Ser
                565                 570                 575

Ser His Val Phe Thr Ser His Pro Arg Met Leu Lys Pro Gln Pro Ala
            580                 585                 590

Ile Glu Leu Pro Leu Gly Gly Glu Tyr Ser Ser Glu Glu Pro Gly Pro
        595                 600                 605

Ser Ser Lys Asp Thr Ala Ser Lys Pro Ser Asp Glu Val Glu Pro Lys
    610                 615                 620

Glu Ser Glu Leu Thr Lys Lys Thr Lys Lys Gly Leu Lys Thr Lys Gly
625                 630                 635                 640

Val Ile Tyr Glu Cys Asn Ile Cys Gly Ala Arg Tyr Lys Lys Arg Asp
                645                 650                 655

Asn Tyr Glu Ala His Lys Lys Tyr Tyr Cys Ser Glu Leu Gln Ile Ala
            660                 665                 670

Lys Pro Ile Ser Ala Gly Thr His Thr Ser Pro Glu Ala Glu Lys Ser
        675                 680                 685

Gln Ile Glu His Glu Pro Trp Ser Gln Met Met His Tyr Lys Leu Gly
    690                 695                 700

Thr Thr Leu Glu Leu Thr Pro Leu Arg Lys Arg Arg Lys Glu Lys Ser
705                 710                 715                 720
```

-continued

```
Leu Gly Asp Glu Glu Pro Pro Ala Phe Glu Ser Thr Lys Ser Gln
            725                 730                 735

Phe Gly Ser Pro Gly Pro Ser Asp Ala Ala Arg Asn Leu Pro Leu Glu
            740                 745                 750

Ser Thr Lys Ser Pro Ala Glu Pro Ser Lys Ser Val Pro Ser Leu Glu
            755                 760                 765

Gly Pro Thr Gly Phe Gln Pro Arg Thr Pro Lys Pro Gly Ser Gly Ser
            770                 775             780

Glu Ser Gly Lys Glu Arg Arg Thr Thr Ser Lys Glu Ile Ser Val Ile
785                 790                 795                 800

Gln His Thr Ser Ser Phe Glu Lys Ser Asp Ser Leu Glu Gln Pro Ser
            805                 810                 815

Gly Leu Glu Gly Glu Asp Lys Pro Leu Ala Gln Phe Pro Ser Pro
            820                 825                 830

Pro Ala Pro His Gly Arg Ser Ala His Ser Leu Gln Pro Lys Leu Val
            835                 840                 845

Arg Gln Pro Asn Ile Gln Val Pro Glu Ile Leu Val Thr Glu Glu Pro
850                 855                 860

Asp Arg Pro Asp Thr Glu Pro Glu Pro Pro Lys Glu Pro Glu Lys
865                 870                 875                 880

Thr Glu Glu Phe Gln Trp Pro Gln Arg Ser Gln Thr Leu Ala Gln Leu
            885                 890                 895

Pro Ala Glu Lys Ala Pro Pro Lys Lys Lys Arg Leu Arg Leu Ala Glu
            900                 905                 910

Met Ala Gln Ser Ser Gly Glu Ser Ser Phe Glu Ser Ser Val Pro Leu
            915                 920                 925

Ser Arg Ser Pro Ser Gln Glu Ser Asn Val Ser Leu Ser Gly Ser Ser
            930                 935                 940

Arg Ser Ala Ser Phe Glu Arg Asp Asp His Gly Lys Ala Glu Ala Pro
945                 950                 955                 960

Asp Pro Ser Ser Asp Met Arg Pro Lys Pro Leu Gly Thr His Met Leu
            965                 970                 975

Thr Val Pro Ser His His Pro His Ala Arg Glu Met Arg Ser Ala
            980                 985                 990

Ser Glu Gln Ser Pro Asn Val Ser His Ser Ala His Met Thr Glu Thr
            995                 1000                1005

Arg Ser Lys Ser Phe Asp Tyr Gly Ser Leu Ser Leu Thr Gly Pro Ser
            1010                1015                1020

Ala Pro Ala Pro Val Ala Pro Ala Gly Glu Ala Pro Pro Glu Arg
1025                1030                1035                1040

Arg Lys Cys Phe Leu Val Arg Ser Pro Ser Leu Ser Arg Pro Pro Glu
            1045                1050                1055

Ser Glu Leu Glu Val Ala Pro Lys Gly Arg Gln Glu Ser Glu Glu Pro
            1060                1065                1070

Gln Pro Ser Ser Ser Lys Pro Ser Ala Lys Ser Ser Leu Ser Gln Ile
            1075                1080                1085

Ser Ser Ala Ala Thr Ser His Gly Gly Pro Gly Gly Lys Gly Pro
            1090                1095                1100

Gly Gln Asp Arg Pro Ala Leu Gly Pro Thr Val Pro Tyr Thr Glu Ala
1105                1110                1115                1120

Leu Gln Val Phe His His Pro Val Ala Gln Thr Pro Leu His Glu Lys
            1125                1130                1135

Pro Tyr Leu Pro Pro Pro Val Ser Leu Phe Ser Phe Gln His Leu Val
            1140                1145                1150
```

```
Gln His Glu Pro Gly Gln Ser Pro Glu Phe Phe Ser Thr Gln Ala Met
        1155                1160                1165

Ser Ser Leu Leu Ser Ser Pro Tyr Ser Met Pro Pro Leu Pro Pro Ser
        1170                1175                1180

Leu Phe Gln Ala Pro Pro Leu Pro Leu Gln Pro Thr Val Leu His Pro
1185                1190                1195                1200

Gly Gln Leu His Leu Pro Gln Leu Met Pro His Pro Ala Asn Ile Pro
        1205                1210                1215

Phe Arg Gln Pro Pro Ser Phe Leu Pro Met Pro Tyr Pro Thr Ser Ser
        1220                1225                1230

Ala Leu Ser Ser Gly Phe Phe Leu Pro Leu Gln Ser Gln Phe Ala Leu
        1235                1240                1245

Gln Leu Pro Gly Asp Val Glu Ser His Leu Pro Gln Ile Lys Thr Ser
        1250                1255                1260

Leu Ala Pro Leu Ala Thr Gly Ser Ala Gly Leu Ser Pro Ser Gln Glu
1265                1270                1275                1280

Tyr Ser Ser Asp Ile Arg Leu Pro Pro Val Ala Pro Ala Ser Ser
        1285                1290                1295

Ser Ala Pro Thr Ser Ala Pro Pro Leu Ala Leu Pro Ala Cys Pro Asp
        1300                1305                1310

Thr Met Val Ser Leu Val Val Pro Val Arg Val Gln Thr Asn Met Pro
        1315                1320                1325

Ser Tyr Gly Ser Ala Met Tyr Thr Thr Leu Ser Gln Ile Leu Val Thr
        1330                1335                1340

Gln Ser Gln Gly Ser Ser Ala Thr Val Ala Leu Pro Lys Phe Glu Glu
1345                1350                1355                1360

Pro Pro Ser Lys Gly Thr Thr Val Cys Gly Ala Asp Val His Glu Val
        1365                1370                1375

Gly Pro Gly Pro Ser Gly Leu Ser Glu Glu Gln Ser Arg Ala Phe Pro
        1380                1385                1390

Thr Pro Tyr Leu Arg Val Pro Val Thr Leu Pro Glu Arg Lys Gly Thr
        1395                1400                1405

Ser Leu Ser Ser Glu Ser Ile Leu Ser Leu Glu Gly Ser Ser Ser Thr
        1410                1415                1420

Ala Gly Gly Ser Lys Arg Val Leu Ser Pro Ala Gly Ser Leu Glu Leu
1425                1430                1435                1440

Thr Met Glu Thr Gln Gln Gln Lys Arg Val Lys Glu Glu Ala Ser
        1445                1450                1455

Lys Ala Asp Glu Lys Leu Glu Leu Val Lys Pro Cys Ser Val Val Leu
        1460                1465                1470

Thr Ser Thr Glu Asp Gly Lys Arg Pro Glu Lys Ser His Leu Gly Asn
        1475                1480                1485

Gln Gly Gln Gly Arg Arg Glu Leu Glu Met Leu Ser Ser Leu Ser Ser
        1490                1495                1500

Asp Pro Ser Asp Thr Lys Glu Ile Pro Pro Leu Pro His Pro Ala Leu
1505                1510                1515                1520

Ser His Gly Gln Ala Pro Gly Ser Glu Ala Leu Lys Glu Tyr Pro Gln
        1525                1530                1535

Pro Ser Gly Lys Pro His Arg Arg Gly Leu Thr Pro Leu Ser Val Lys
        1540                1545                1550

Lys Glu Asp Ser Lys Glu Gln Pro Asp Leu Pro Ser Leu Ala Pro Pro
        1555                1560                1565

Ser Ser Leu Pro Leu Ser Glu Thr Ser Ser Arg Pro Ala Lys Ser Gln
        1570                1575                1580
```

-continued

Glu Gly Thr Asp Ser Lys Lys Val Leu Gln Phe Pro Ser Leu His Thr
1585                1590                1595                1600

Thr Thr Asn Val Ser Trp Cys Tyr Leu Asn Tyr Ile Lys Pro Asn His
            1605                1610                1615

Ile Gln His Ala Asp Arg Arg Ser Ser Val Tyr Ala Gly Trp Cys Ile
        1620                1625                1630

Ser Leu Tyr Asn Pro Asn Leu Pro Gly Val Ser Thr Lys Ala Ala Leu
            1635                1640                1645

Ser Leu Leu Arg Ser Lys Gln Lys Val Ser Lys Glu Thr Tyr Thr Met
        1650                1655                1660

Ala Thr Ala Pro His Pro Glu Ala Gly Arg Leu Val Pro Ser Ser Ser
1665                1670                1675                1680

Arg Lys Pro Arg Met Thr Glu Val His Leu Pro Ser Leu Val Ser Pro
            1685                1690                1695

Glu Gly Gln Lys Asp Leu Ala Arg Val Glu Lys Glu Glu Arg Arg
        1700                1705                1710

Gly Glu Pro Glu Glu Asp Ala Pro Ala Ser Gln Arg Gly Glu Pro Ala
            1715                1720                1725

Arg Ile Lys Ile Phe Glu Gly Gly Tyr Lys Ser Asn Glu Glu Tyr Val
        1730                1735                1740

Tyr Val Arg Gly Arg Gly Arg Gly Lys Tyr Val Cys Glu Glu Cys Gly
1745                1750                1755                1760

Ile Arg Cys Lys Lys Pro Ser Met Leu Lys Lys His Ile Arg Thr His
            1765                1770                1775

Thr Asp Val Arg Pro Tyr Val Cys Lys His Cys His Phe Ala Phe Lys
            1780                1785                1790

Thr Lys Gly Asn Leu Thr Lys His Met Lys Ser Lys Ala His Ser Lys
            1795                1800                1805

Lys Cys Gln Glu Thr Gly Val Leu Glu Glu Leu Glu Ala Glu Glu Gly
1810                1815                1820

Thr Ser Asp Asp Leu Phe Gln Asp Ser Glu Gly Arg Glu Gly Ser Glu
1825                1830                1835                1840

Ala Val Glu Glu His Gln Phe Ser Asp Leu Glu Asp Ser Asp Ser Asp
            1845                1850                1855

Ser Asp Leu Asp Glu Asp Glu Asp Glu Glu Glu Ser Gln Asp
            1860                1865                1870

Glu Leu Ser Arg Pro Ser Ser Glu Ala Pro Pro Gly Pro Pro His
            1875                1880                1885

Ala Leu Arg Ala Asp Ser Ser Pro Ile Leu Gly Pro Gln Pro Pro Asp
1890                1895                1900

Ala Pro Ala Ser Gly Thr Glu Ala Thr Arg Gly Ser Ser Val Ser Glu
1905                1910                1915                1920

Ala Glu Arg Leu Thr Ala Ser Ser Cys Ser Met Ser Ser Gln Ser Met
            1925                1930                1935

Pro Gly Leu Pro Trp Leu Gly Pro Ala Pro Leu Gly Ser Val Glu Lys
            1940                1945                1950

Asp Thr Gly Ser Ala Leu Ser Tyr Lys Pro Val Ser Pro Arg Arg Pro
            1955                1960                1965

Trp Ser Pro Ser Lys Glu Ala Gly Ser Arg Pro Pro Leu Ala Arg Lys
            1970                1975                1980

His Ser Leu Thr Lys Asn Asp Ser Ser Pro Gln Arg Cys Ser Pro Ala
1985                1990                1995                2000

-continued

Arg Glu Pro Gln Ala Ser Ala Pro Ser Pro Pro Gly Leu His Val Asp
                2005                2010                2015

Pro Gly Arg Gly Met Gly Pro Leu Pro Cys Gly Ser Pro Arg Leu Gln
                2020                2025                2030

Leu Ser Pro Leu Thr Leu Cys Pro Leu Gly Arg Glu Leu Ala Pro Arg
                2035                2040                2045

Ala His Val Leu Ser Lys Leu Glu Gly Thr Thr Asp Pro Gly Leu Pro
                2050                2055                2060

Arg Tyr Ser Pro Thr Arg Arg Trp Ser Pro Gly Gln Ala Glu Ser Pro
2065                2070                2075                2080

Pro Arg Ser Ala Pro Pro Gly Lys Trp Ala Leu Ala Gly Pro Gly Ser
                2085                2090                2095

Pro Ser Ala Gly Glu His Gly Pro Gly Leu Gly Leu Ala Pro Arg Val
                2100                2105                2110

Leu Phe Pro Pro Ala Pro Leu Pro His Lys Leu Leu Ser Arg Ser Pro
                2115                2120                2125

Glu Thr Cys Ala Ser Pro Trp Gln Lys Ala Glu Ser Arg Ser Pro Ser
                2130                2135                2140

Cys Ser Pro Gly Pro Ala His Pro Leu Ser Ser Arg Pro Phe Ser Ala
2145                2150                2155                2160

Leu His Asp Phe His Gly His Ile Leu Ala Arg Thr Glu Glu Asn Ile
                2165                2170                2175

Phe Ser His Leu Pro Leu His Ser Gln His Leu Thr Arg Ala Pro Cys
                2180                2185                2190

Pro Leu Ile Pro Ile Gly Gly Ile Gln Met Val Gln Ala Arg Pro Gly
                2195                2200                2205

Ala His Pro Thr Leu Leu Pro Gly Pro Thr Ala Ala Trp Val Ser Gly
                2210                2215                2220

Phe Ser Gly Gly Gly Ser Asp Leu Thr Gly Ala Arg Glu Ala Gln Glu
2225                2230                2235                2240

Arg Gly Arg Trp Ser Pro Thr Glu Ser Ser Ser Ala Ser Val Ser Pro
                2245                2250                2255

Val Ala Lys Val Ser Lys Phe Thr Leu Ser Ser Glu Leu Glu Gly Arg
                2260                2265                2270

Asp Tyr Pro Lys Glu Arg Glu Arg Thr Gly Gly Pro Gly Arg Pro
                2275                2280                2285

Pro Asp Trp Thr Pro His Gly Thr Gly Ala Pro Ala Glu Pro Thr Pro
                2290                2295                2300

Thr His Ser Pro Cys Thr Pro Asp Thr Leu Pro Arg Pro Pro Gln
2305                2310                2315                2320

Gly Arg Arg Ala Ala Gln Ser Trp Ser Pro Arg Leu Glu Ser Pro Arg
                2325                2330                2335

Ala Pro Ala Asn Pro Glu Pro Ser Ala Thr Pro Pro Leu Asp Arg Ser
                2340                2345                2350

Ser Ser Val Gly Cys Leu Ala Glu Ala Ser Ala Arg Phe Pro Ala Arg
                2355                2360                2365

Thr Arg Asn Leu Ser Gly Glu Ser Arg Thr Arg Gln Asp Ser Pro Lys
                2370                2375                2380

Pro Ser Gly Ser Gly Glu Pro Arg Ala His Pro His Gln Pro Glu Asp
2385                2390                2395                2400

Arg Val Pro Pro Asn Ala
                2405

```
<210> SEQ ID NO 3
<211> LENGTH: 852
<212> TYPE: PRT
<213> ORGANISM: Homo sapiens

<400> SEQUENCE: 3

Pro Ser Val Leu Gln Lys His Ile Arg Ser His Thr Gly Glu Arg Pro
 1               5                  10                  15

Tyr Pro Cys Gly Pro Cys Gly Phe Ser Phe Lys Thr Lys Ser Asn Leu
             20                  25                  30

Tyr Lys His Arg Lys Ser His Ala His Arg Ile Lys Ala Gly Leu Ala
         35                  40                  45

Ser Gly Met Gly Gly Glu Met Tyr Pro His Gly Leu Glu Met Glu Arg
     50                  55                  60

Ile Pro Gly Glu Glu Phe Glu Glu Pro Thr Glu Gly Ser Thr Asp
 65                  70                  75                  80

Ser Glu Glu Glu Thr Ser Ala Thr Ser Gly His Pro Ala Glu Leu Ser
                 85                  90                  95

Pro Arg Pro Lys Gln Pro Leu Leu Ser Ser Gly Leu Tyr Ser Ser Gly
            100                 105                 110

Ser His Ser Ser Ser His Glu Arg Cys Ser Leu Ser Gln Ser Ser Thr
        115                 120                 125

Ala Gln Ser Leu Glu Asp Pro Pro Phe Val Glu Pro Ser Ser Glu
    130                 135                 140

His Pro Leu Ser His Lys Pro Glu Asp Thr His Thr Ile Lys Gln Lys
145                 150                 155                 160

Leu Ala Leu Arg Leu Ser Glu Arg Lys Lys Val Ile Asp Glu Gln Ala
                165                 170                 175

Phe Leu Ser Pro Gly Ser Lys Gly Ser Thr Glu Ser Gly Tyr Phe Ser
            180                 185                 190

Arg Ser Glu Ser Ala Glu Gln Gln Val Ser Pro Pro Asn Thr Asn Ala
        195                 200                 205

Lys Ser Tyr Ala Glu Ile Ile Phe Gly Lys Cys Gly Arg Ile Gly Gln
    210                 215                 220

Arg Thr Ala Met Leu Thr Ala Thr Ser Thr Gln Pro Leu Leu Pro Leu
225                 230                 235                 240

Ser Thr Glu Asp Lys Pro Ser Leu Val Pro Leu Ser Val Pro Arg Thr
                245                 250                 255

Gln Val Ile Glu His Ile Thr Lys Leu Ile Thr Ile Asn Glu Ala Val
            260                 265                 270

Val Asp Thr Ser Glu Ile Asp Ser Val Lys Pro Arg Arg Ser Ser Leu
        275                 280                 285

Ser Arg Arg Ser Ser Met Glu Ser Pro Lys Ser Ser Leu Tyr Arg Glu
    290                 295                 300

Pro Leu Ser Ser His Ser Glu Lys Thr Lys Pro Glu Gln Ser Leu Leu
305                 310                 315                 320

Ser Leu Gln His Pro Pro Ser Thr Ala Pro Val Pro Leu Leu Arg
                325                 330                 335

Ser His Ser Met Pro Ser Ala Ala Cys Thr Ile Ser Thr Pro His His
            340                 345                 350

Pro Phe Arg Gly Ser Tyr Ser Phe Asp Asp His Ile Thr Asp Ser Glu
        355                 360                 365

Ala Leu Ser Arg Ser Ser His Val Phe Thr Ser His Pro Arg Met Leu
    370                 375                 380
```

-continued

```
Lys Pro Gln Pro Ala Ile Glu Leu Pro Leu Gly Gly Glu Tyr Ser Ser
385                 390                 395                 400

Glu Glu Pro Gly Pro Ser Ser Lys Asp Thr Ala Ser Lys Pro Ser Asp
            405                 410                 415

Glu Val Glu Pro Lys Glu Ser Glu Leu Thr Lys Lys Thr Lys Lys Gly
        420                 425                 430

Leu Lys Thr Lys Gly Val Ile Tyr Glu Cys Asn Ile Cys Gly Ala Arg
        435                 440                 445

Tyr Lys Lys Arg Asp Asn Tyr Glu Ala His Lys Lys Tyr Tyr Cys Ser
    450                 455                 460

Glu Leu Gln Ile Ala Lys Pro Ile Ser Ala Gly Thr His Thr Ser Pro
465                 470                 475                 480

Glu Ala Glu Lys Ser Gln Ile Glu His Glu Pro Trp Ser Gln Met Met
            485                 490                 495

His Tyr Lys Leu Gly Thr Thr Leu Glu Leu Thr Pro Leu Arg Lys Arg
        500                 505                 510

Arg Lys Glu Lys Ser Leu Gly Asp Glu Glu Pro Ala Phe Glu
        515                 520                 525

Ser Thr Lys Ser Gln Phe Gly Ser Pro Gly Pro Ser Asp Ala Ala Arg
530                 535                 540

Asn Leu Pro Leu Glu Ser Thr Lys Ser Pro Ala Glu Pro Ser Lys Ser
545                 550                 555                 560

Val Pro Ser Leu Glu Gly Pro Thr Gly Phe Gln Pro Arg Thr Pro Lys
            565                 570                 575

Pro Gly Ser Gly Ser Glu Ser Gly Lys Glu Arg Arg Thr Thr Ser Lys
        580                 585                 590

Glu Ile Ser Val Ile Gln His Thr Ser Ser Phe Glu Lys Ser Asp Ser
        595                 600                 605

Leu Glu Gln Pro Ser Gly Leu Glu Gly Glu Asp Lys Pro Leu Ala Gln
        610                 615                 620

Phe Pro Ser Pro Pro Ala Pro His Gly Arg Ser Ala His Ser Leu
625                 630                 635                 640

Gln Pro Lys Leu Val Arg Gln Pro Asn Ile Gln Val Pro Glu Ile Leu
            645                 650                 655

Val Thr Glu Glu Pro Asp Arg Pro Asp Thr Glu Pro Glu Pro Pro
            660                 665                 670

Lys Glu Pro Glu Lys Thr Glu Glu Phe Gln Trp Pro Gln Arg Ser Gln
        675                 680                 685

Thr Leu Ala Gln Leu Pro Ala Glu Lys Ala Pro Lys Lys Lys Arg
        690                 695                 700

Leu Arg Leu Ala Glu Met Ala Gln Ser Ser Gly Glu Ser Ser Phe Glu
705                 710                 715                 720

Ser Ser Val Pro Leu Ser Arg Ser Pro Ser Gln Glu Ser Asn Val Ser
            725                 730                 735

Leu Ser Gly Ser Ser Arg Ser Ala Ser Phe Glu Arg Asp Asp His Gly
        740                 745                 750

Lys Ala Glu Ala Pro Asp Pro Ser Ser Asp Met Arg Pro Lys Pro Leu
        755                 760                 765

Gly Thr His Met Leu Thr Val Pro Ser His His Pro His Ala Arg Glu
        770                 775                 780

Met Arg Arg Ser Ala Ser Glu Gln Ser Pro Asn Val Ser His Ser Ala
785                 790                 795                 800

His Met Thr Glu Thr Arg Ser Lys Ser Phe Asp Tyr Gly Ser Leu Ser
            805                 810                 815
```

```
Leu Thr Gly Pro Ser Ala Pro Ala Pro Val Ala Pro Pro Ala Gly Glu
            820                 825                 830

Ala Pro Pro Glu Arg Arg Lys Cys Phe Leu Val Arg Ser Pro Ser Leu
            835                 840                 845

Ser Arg Pro Pro
    850

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 4
gaccaagagu aaucucuact t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 5
guagagauua cucuugguct t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 6
aucugauucu cucgagcagt t                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 7
cugcucgaga gaaucagaut t                                              21

<210> SEQ ID NO 8
<211> LENGTH: 786
<212> TYPE: PRT
<213> ORGANISM: Homo sapiens
```

-continued

```
<400> SEQUENCE: 8

Glu Met Leu Ser Ser Leu Ser Ser Asp Pro Ser Asp Thr Lys Glu Ile
 1               5                  10                  15

Pro Pro Leu Pro His Pro Ala Leu Ser His Gly Gln Ala Pro Gly Ser
            20                  25                  30

Glu Ala Leu Lys Glu Tyr Pro Gln Pro Ser Gly Lys Pro His Arg Arg
        35                  40                  45

Gly Leu Thr Pro Leu Ser Val Lys Lys Glu Asp Ser Lys Glu Gln Pro
    50                  55                  60

Asp Leu Pro Ser Leu Ala Pro Pro Ser Ser Leu Pro Leu Ser Glu Thr
65                  70                  75                  80

Ser Ser Arg Pro Ala Lys Ser Gln Glu Gly Thr Asp Ser Lys Lys Val
                85                  90                  95

Leu Gln Phe Pro Ser Leu His Thr Thr Thr Asn Val Ser Trp Cys Tyr
            100                 105                 110

Leu Asn Tyr Ile Lys Pro Asn His Ile Gln His Ala Asp Arg Arg Ser
        115                 120                 125

Ser Val Tyr Ala Gly Trp Cys Ile Ser Leu Tyr Asn Pro Asn Leu Pro
    130                 135                 140

Gly Val Ser Thr Lys Ala Ala Leu Ser Leu Leu Arg Ser Lys Gln Lys
145                 150                 155                 160

Val Ser Lys Glu Thr Tyr Thr Met Ala Thr Ala Pro His Pro Glu Ala
                165                 170                 175

Gly Arg Leu Val Pro Ser Ser Ser Arg Lys Pro Arg Met Thr Glu Val
            180                 185                 190

His Leu Pro Ser Leu Val Ser Pro Glu Gly Gln Lys Asp Leu Ala Arg
        195                 200                 205

Val Glu Lys Glu Glu Glu Arg Arg Gly Glu Pro Glu Glu Asp Ala Pro
    210                 215                 220

Ala Ser Gln Arg Gly Glu Pro Ala Arg Ile Lys Ile Phe Glu Gly Gly
225                 230                 235                 240

Tyr Lys Ser Asn Glu Glu Tyr Val Tyr Val Arg Gly Arg Gly Arg Gly
                245                 250                 255

Lys Tyr Val Cys Glu Glu Cys Gly Ile Arg Cys Lys Lys Pro Ser Met
            260                 265                 270

Leu Lys Lys His Ile Arg Thr His Thr Asp Val Arg Pro Tyr Val Cys
        275                 280                 285

Lys His Cys His Phe Ala Phe Lys Thr Lys Gly Asn Leu Thr Lys His
    290                 295                 300

Met Lys Ser Lys Ala His Ser Lys Lys Cys Gln Glu Thr Gly Val Leu
305                 310                 315                 320

Glu Glu Leu Glu Ala Glu Gly Thr Ser Asp Asp Leu Phe Gln Asp
                325                 330                 335

Ser Glu Gly Arg Glu Gly Ser Glu Ala Val Glu Glu His Gln Phe Ser
            340                 345                 350

Asp Leu Glu Asp Ser Asp Ser Asp Leu Asp Glu Asp Glu Asp
        355                 360                 365

Glu Asp Glu Glu Glu Ser Gln Asp Glu Leu Ser Arg Pro Ser Ser Glu
    370                 375                 380

Ala Pro Pro Pro Gly Pro Pro His Ala Leu Arg Ala Asp Ser Ser Pro
385                 390                 395                 400

Ile Leu Gly Pro Gln Pro Pro Asp Ala Pro Ala Ser Gly Thr Glu Ala
                405                 410                 415
```

```
Thr Arg Gly Ser Ser Val Ser Glu Ala Glu Arg Leu Thr Ala Ser Ser
            420                 425                 430
Cys Ser Met Ser Ser Gln Ser Met Pro Gly Leu Pro Trp Leu Gly Pro
            435                 440                 445
Ala Pro Leu Gly Ser Val Glu Lys Asp Thr Gly Ser Ala Leu Ser Tyr
450                 455                 460
Lys Pro Val Ser Pro Arg Arg Pro Trp Ser Pro Ser Lys Glu Ala Gly
465                 470                 475                 480
Ser Arg Pro Pro Leu Ala Arg Lys His Ser Leu Thr Lys Asn Asp Ser
                485                 490                 495
Ser Pro Gln Arg Cys Ser Pro Ala Arg Glu Pro Gln Ala Ser Ala Pro
            500                 505                 510
Ser Pro Pro Gly Leu His Val Asp Pro Gly Arg Gly Met Gly Pro Leu
            515                 520                 525
Pro Cys Gly Ser Pro Arg Leu Gln Leu Ser Pro Leu Thr Leu Cys Pro
            530                 535                 540
Leu Gly Arg Glu Leu Ala Pro Arg Ala His Val Leu Ser Lys Leu Glu
545                 550                 555                 560
Gly Thr Thr Asp Pro Gly Leu Pro Arg Tyr Ser Pro Thr Arg Arg Trp
                565                 570                 575
Ser Pro Gly Gln Ala Glu Ser Pro Arg Ser Ala Pro Pro Gly Lys
            580                 585                 590
Trp Ala Leu Ala Gly Pro Gly Ser Pro Ser Ala Gly Glu His Gly Pro
            595                 600                 605
Gly Leu Gly Leu Ala Pro Arg Val Leu Phe Pro Ala Pro Leu Pro
610                 615                 620
His Lys Leu Leu Ser Arg Ser Pro Glu Thr Cys Ala Ser Pro Trp Gln
625                 630                 635                 640
Lys Ala Glu Ser Arg Ser Pro Ser Cys Ser Pro Gly Pro Ala His Pro
                645                 650                 655
Leu Ser Ser Arg Pro Phe Ser Ala Leu His Asp Phe His Gly His Ile
            660                 665                 670
Leu Ala Arg Thr Glu Glu Asn Ile Phe Ser His Leu Pro Leu His Ser
            675                 680                 685
Gln His Leu Thr Arg Ala Pro Cys Pro Leu Ile Pro Ile Gly Gly Ile
            690                 695                 700
Gln Met Val Gln Ala Arg Pro Gly Ala His Pro Thr Leu Leu Pro Gly
705                 710                 715                 720
Pro Thr Ala Ala Trp Val Ser Gly Phe Ser Gly Gly Ser Asp Leu
                725                 730                 735
Thr Gly Ala Arg Glu Ala Gln Glu Arg Gly Arg Trp Ser Pro Thr Glu
            740                 745                 750
Ser Ser Ser Ala Ser Val Ser Pro Val Ala Lys Val Ser Lys Phe Thr
            755                 760                 765
Leu Ser Ser Glu Leu Glu Gly Arg Asp Tyr Pro Lys Glu Arg Glu Arg
            770                 775                 780
Thr Gly
785

<210> SEQ ID NO 9
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
```

```
<220> FEATURE:
<223> OTHER INFORMATION: Description of Artificial Sequence: Synthetic
      oligonucleotide

<400> SEQUENCE: 9
gccaaaucac auccagcaut t                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 10
augcuggaug ugauuuggct t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 11
gcaaguucga gaacgaggat t                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 12
uccucguucu cgaacuugct t                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 13
gaggcucgga gaaggacact t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
```

```
<220> FEATURE:
<223> OTHER INFORMATION: Description of Artificial Sequence: Synthetic
      oligonucleotide

<400> SEQUENCE: 14
guguccuucu ccgagccuct t                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 15
aaacaaguca agaaauuaat t                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 16
uuaauuucuu gacuuguuut t                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 17
uaugaagaag gacgagguct t                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 18
gaccucgucc uucuucauat t                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
```

```
<220> FEATURE:
<223> OTHER INFORMATION: Description of Artificial Sequence: Synthetic
      oligonucleotide

<400> SEQUENCE: 19
ccugaagauc uucaacaact t                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 20
guuguugaag aucuucaggt t                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 21
uuggaacucu acucaaccct t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 22
ggguugagua gaguuccaat t                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 23
ggcacgaaug gaauagauat t                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
```

-continued

```
<220> FEATURE:
<223> OTHER INFORMATION: Description of Artificial Sequence: Synthetic
      oligonucleotide

<400> SEQUENCE: 24
uaucuauucc auucgugcct t                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 25
gaacaacuau ugucugcagt t                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 26
cugcagacaa uaguuguuct t                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 27
agaucauccu uaaauuuugt t                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 28
caaaauuuaa ggaugaucut t                                              21

<210> SEQ ID NO 29
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
```

```
<220> FEATURE:
<223> OTHER INFORMATION: Description of Artificial Sequence: Synthetic
      oligonucleotide

<400> SEQUENCE: 29
ggucacauca aguuaacagt t                                              21

<210> SEQ ID NO 30
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 30
cuguuaacuu gaugugacct t                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 31
ggaaguaguc cuugcacuut t                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 32
aagugcaagg acuacuucct t                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 33
ugcaacagac ccccaacuut t                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
```

```
<220> FEATURE:
<223> OTHER INFORMATION: Description of Artificial Sequence: Synthetic
      oligonucleotide

<400> SEQUENCE: 34
aaguuggggg ucuguugcat t                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 35
accaaguagc aagguucaat t                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 36
uugaaccuug cuacuuggut t                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 37
ggacagaguc agauuacagt t                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 38
cuguaaucug acucugucct t                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
```

-continued

```
<220> FEATURE:
<223> OTHER INFORMATION: Description of Artificial Sequence: Synthetic
      oligonucleotide

<400> SEQUENCE: 39
ccagaaugau gguguugact t                                              21

<210> SEQ ID NO 40
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 40
gucaacacca ucauucuggt t                                              21

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 41

Gly Gly Gly Gly Ser Gly Gly Gly Gly Ser Gly Gly Gly Gly Ser
  1               5                  10                  15
```

METHODS FOR MODULATING BONE FORMATION AND MINERALIZATION BY MODULATING KRC ACTIVITY

RELATED APPLICATIONS

This application claims the benefit of U.S. Provisional Application No. 60/671,619, filed on Apr. 15, 2005, titled "METHODS FOR MODULATING BONE FORMATION AND MINERALIZATION BY MODULATING KRC ACTIVITY". This application is related to PCT/US2004/036641, filed Nov. 3, 2004, which is a continuation-in-part of U.S. application Ser. No. 10/701,401, filed Nov. 3, 2003, which claims the benefit of priority to PCT application PCT/US02/14166, filed May 3, 2002, and U.S. Provisional Application Ser. No. 60/288,369, filed May 3, 2001. The entire contents of each of these applications are incorporated herein by this reference.

GOVERNMENT FUNDING

Work described herein was supported, at least in part, by the National Institutes of Health (NIH) under grant numbers AI29673, AR46983. The government may have certain rights to this invention.

BACKGROUND OF THE INVENTION

Transcription factors are a group of molecules within the cell that function to connect the pathways from extracellular signals to intracellular responses. Immediately after an environmental stimulus, these proteins which reside predominantly in the cytosol are translocated to the nucleus where they bind to specific DNA sequences in the promoter elements of target genes and activate the transcription of these target genes. One family of transcription factors, the ZAS (zinc finger-acidic domain structures) DNA binding protein family is involved in the regulation of gene transcription, DNA recombination, and signal transduction (Mak, C. H., et al. 1998. *Immunogenetics* 48: 32-39).

Zinc finger proteins are identified by the presence of highly conserved Cys2His2 zinc fingers (Mak, C. H., et al. 1998. *Immunogenetics* 48: 32-39). The zinc fingers are an integral part of the DNA binding structure called the ZAS domain. The ZAS domain is comprised of a pair of zinc fingers, a glutamic acid/aspartic acid-rich acidic sequence and a serine/threonine rich sequence (Mak, C. H., et al. 1998. *Immunogenetics* 48: 32-39). The ZAS domains have been shown to interact with the kB like cis-acting regulatory elements found in the promoter or enhancer regions of genes. The ZAS proteins recognize nuclear factor kB binding sites which are present in the enhancer sequences of many genes, especially those involved in immune responses (Bachmeyer, et al. 1999. *Nuc. Acid Res.* 27, 643-648). The ZAS DNA binding proteins have been shown to be transcription regulators of these target genes (Bachmeyer, et al. 1999. *Nuc. Acid Res.* 27, 643-648; Wu et al. 1998. *Science* 281, 998-1001).

The zinc finger transcription factor Kappa Recognition Component ("KRC", also known as schnurri3 or Shn3, and human immunodeficiency virus type I enhancer-binding protein 3 (HIVEP3)) is a member of the ZAS DNA binding family of proteins (Bachmeyer, et al. 1999. *Nuc. Acid Res.* 27, 643-648; Wu et al. 1998. *Science* 281, 998-1001). The KRC gene was identified as a DNA binding protein for the heptameric consensus signal sequences involved in somatic V(D)J recombination of the immune receptor genes (Mak, C. H., et al. 1994. *Nuc. Acid Res.* 22: 383-390). KRC is a substrate for epidermal growth factor receptor kinase and p34cdc2 kinase in vitro (Bachmeyer, et al. 1999. *Nuc. Acid Res.* 27, 643-648).

In *Drosophila*, Schnurri (Shn) plays an important role during embryogenesis in the regulation of genes downstream of decapentaplegic (Dpp), a member of the TGF-β superfamily (Arora, K., et al. (1995). *Cell* 81, 781-790). Ligation of Dpp to its receptors initiates a signal cascade that results in Med, the *Drosophila* Co-Smad homologue, partnering with Mad, the *Drosophila* R-Smad homologue (Dai, H., et al. (2000). *Dev Biol* 227, 373-387). The Mad/Med complex translocates to the nucleus where it interacts with Shn. It has been demonstrated that Shn recruits the necessary transcriptional co-repressors to the Mad/Med complex bound to the regulatory region of Brinker (Brk). Since Brk is a global repressor of Dpp-mediated gene expression, Shn-induced repression of Brk expression thus promotes Dpp's ability to induce expression of target genes (Arora, K., et al. (1995). *Cell* 81, 781-790; Dai, H., et al. (2000). *Dev Biol* 227, 373-387; Marty, T., et al. (2000). *Nat Cell Biol* 2, 745-749).

Although a number of studies have demonstrated that Shn3 regulates the activities of other important transcription proteins, including NF-κB and AP-1, no role for the mammalian Shn genes in TGF-β signaling has yet to be identified (Hong, J. W., et al. (2003). *Proc Natl Acad Sci USA* 100, 12301-12306; Oukka, M., et al. (2004). *J Exp Med* 199, 15-24; Oukka, M., et al. (2002). *Mol Cell* 9, 121-131). Furthermore, the in vivo role(s) of Shn3 remain largely unknown.

Bone is a dynamic tissue whose matrix components are continuously being remodeled to preserve the structural integrity of the skeleton. Bone remodeling is a cyclical process where under normal physiological conditions, bone formation occurs only at sites where bone resorption has previously taken place. Homeostatic remodeling of the skeleton is mediated primarily, if not exclusively, by the osteoclast and the osteoblast (Erlebacher, A., et al. (1995). *Cell* 80, 371-378). Osteoclasts are giant multinucleated cells of hematopoietic origin that are responsible for bone resorption. Osteoblasts, which originate from mesenchymal stem cells, synthesize the matrix constituents on bone forming surfaces. Proliferation, differentiation and bone remodeling activities of these cells involve a complex temporal network of growth factors, signaling proteins, and transcription factors (Karsenty, G., and Wagner, E. F. (2002). *Dev Cell* 2, 389-406). Dysregulation of any one component may disrupt the remodeling process and contribute to the pathogenesis of certain skeletal disorders, such as osteoporosis and Paget's disease. Rare single gene disorders resulting in elevated bone mass due to osteoclast defects, collectively termed osteopetrosis, have been identified. Rarer are single gene disorders, exemplified by Camerati-Engelman syndrome, collectively termed osteosclerosis, in which elevated bone mass is due to intrinsically-elevated osteoblast activity (Appendix 2003).

The transcription factor Runx2 is the principal regulator of osteoblast differentiation during embryonic development. It interacts with a number of nuclear transcription factors, coactivators, and adaptor proteins that interpret extracellular signals to ensure homeostatic osteoblast development and activity (Lian, J. B., et al. (2004). *Crit Rev Eukaryot Gene Expr* 14, 1-41; Stein, G. S., et al. (2004). *Oncogene* 23, 4315-4329). Mutations in Runx2 cause the human autosomal dominant disease cleidoranial dysplasia (Lee, B., et al. (1997). *Nat Genet.* 16, 307-310; Mundlos, S., et al. (1997). *Cell* 89, 773-779; Otto, F., et al. (1997). *Cell* 89, 765-771). Runx2$^{-/-}$ mice exhibit a complete lack of both intramembranous and endochondral ossification, which results in an unmineralized skeleton (Komori, T., et al. (1997). *Cell* 89, 755-764; Otto, F., et al. (1997). *Cell* 89, 765-771). In contrast to the significant progress in understanding the molecular mechanisms responsible for osteoblast differentiation during embryonic development, only a small number of genes are known to regulate postnatal osteoblast function (Yoshida, Y., et al. (2000). *Cell* 103, 1085-1097; Kim, S., et al. (2003). *Genes Dev* 17, 1979-1991). LRP5, a Wnt coreceptor, is important in the regulation of bone mass in adult humans and rodents (Johnson, M. L., et al. (2004). *J Bone Miner Res* 19, 1749-1757). Runx2, in addition to its central role in osteoblast differentiation, also regulates mature osteoblast activity in adult mice (Ducy, P., et al. (1999). *Genes Dev* 13, 1025-1036) in part through its induction of ATF4, another protein demonstrated to be important in postnatal bone formation (Yang, X., et al. (2004). *Cell* 117, 387-398). TGFβ has a complex function in bone homeostasis mediated in part through the activity of the SMAD3 E3 ligase, Smurf1.

Transforming growth factor-β (TGF-β) has been known for some time to have particular importance in skeletal patterning, bone remodeling and bone matrix formation (Chang, H., et al. (2002). *Endocr Rev* 23, 787-823). TGF-β has been found to have a multifaceted role during osteoblastogenesis. TGF-β has been demonstrated to promote early osteoblast differentiation but inhibit the later stages of maturation (Canalis, E. (2003). *Osteoenic Growth Factors*. In Primer on the Metabolic Bone Disease and Disorders of Mineral Metabolism, M. J. Favus, ed. (The American Society for Bone and Mineral Research), pp. 28-31.). TGF-β can elicit different cellular responses in the osteoblast through its ability to positively and negatively regulate gene transcription (Alliston, T., et al. (2001). *Embo J* 20, 2254-2272; Takai, H., et al. (1998). *J Biol Chem* 273, 27091-27096). Both activation and repression of gene expression by TGF-β utilize the same set of ubiquitous Smad proteins. However, specific cofactors that bind to Smads are believed to dictate whether a gene is up-regulated or down-regulated in response to TGF-β (Shi, Y., and Massague, J. (2003). Cell 113, 685-700). A similar transcriptional mechanism may account for the variable effects of TGF-β on osteoblast differentiation. Transcriptional cofactors expressed early in osteoblast differentiation may be required to regulate those genes downstream of TGF-β that drive the initial stages of differentiation. Different cofactors expressed at later time points in osteoblast differentiation would then be necessary for TGF-β to suppress the terminal stage of maturation.

Further elucidation of the factors influencing osteoblast activity would be of value in identifying agents capable of modulating bone formation and mineralization. The identification of such agents and methods of using such agents would be of great benefit in the treatment of disorders that would benefit from increased or decreased bone formation.

SUMMARY OF THE INVENTION

The present invention is based, at least in part, on the discovery that KRC modulates osteoblast formation and mineralization since mice bearing a null mutation in KRC exhibit a pronounced osteosclerotic phenotype, due to augmented osteoblast activity and bone formation. Downstream of TGF-β signaling in osteoblasts the formation of a multimeric complex between KRC, Runx2, Smad3, and the E3 ubiquitin ligase, WWP1 which inhibits Runx2 function due to the ability of WWP1 to promote Runx2 polyubiquitination and proteasome-dependent degradation is promoted. KRC is an integral and required component of this complex, since its absence in osteoblasts results in elevated levels of Runx2 protein, enhanced Runx2 transcriptional activity, elevated transcription of Runx2 target genes, and profoundly increased bone formation in vivo. The present invention is also based, at least in part, on the discovery that KRC and WWP1 also form a complex with RSK2 which promotes RSK2 phosphorylation and inhibits RSK2 function due to the ability of WWP1 to promote RSK2 ubiquitination.

Accordingly, in one aspect, the invention pertains to a method for increasing bone formation and mineralization, comprising contacting an osteoblast with an agent that decreases the expression and/or biological activity of KRC in the osteoblast such that bone formation and mineralization is increased.

In another aspect, the invention pertains to a method for treating or preventing a disease, disorder, condition, or injury that would benefit from increased bone formation and mineralization in a subject, comprising contacting an osteoblast from the subject with an agent that decreases the expression and/or biological activity of KRC in the osteoblast such that the bone formation and mineralization in the subject is increased.

In yet another aspect, the invention pertains to a method for decreasing bone formation and mineralization, comprising contacting an osteoblast with an agent that increases the expression and/or biological activity of KRC in the osteoblast such that bone formation and mineralization is decreased.

In another aspect, the invention pertains to a method for treating or preventing a disease, disorder, condition, or injury that would benefit from decreased bone formation and mineralization in a subject, comprising contacting an osteoblast from the subject with an agent that increases the expression and/or biological activity of KRC in the osteoblast such that the bone formation and mineralization in the subject is decreased.

In one embodiment, the step of contacting occurs in vitro. In one embodiment, the step of contacting occurs in vivo.

In one embodiment, the agent is present on a surface.

In one embodiment, the disease, disorder, condition, or injury is selected from the group consisting of: osteoporosis, osteopenia, osteomalacia, and osteitis deformans (Paget's disease of bone).

In another embodiment, the disease, disorder, condition, or injury is selected from the group consisting of: craniosynostosis and osteitis condensans.

In one embodiment, the agent is selected from the group consisting of: a nucleic acid molecule that is antisense to a KRC molecule, a nucleic acid molecule that is antisense to a RUNX2 molecule, a nucleic acid molecule that is antisense to a WWP1 molecule, a nucleic acid molecule that is antisense to a RSK2 molecule, a KRC siRNA molecule, a RUNX2 siRNA molecule, a WWP1 siRNA molecule, a RSK2 siRNA molecule, a dominant negative KRC molecule, a dominant negative Runx2 molecule, a dominant negative WWP1 molecule, a dominant negative RSK2 molecule, or combinations thereof.

In another embodiment, the agent is selected from the group consisting of: a nucleic acid molecule encoding a KRC polypeptide, a nucleic acid molecule encoding a SMAD3 polypeptide, a nucleic acid molecule encoding a Runx2 polypeptide, a nucleic acid molecule encoding a WWP1 polypeptide, a nucleic acid molecule encoding RSK2 polypeptide, a KRC polypeptide, a SMAD3 polypeptide, a Runx2 polypeptide, a WWP1 polypeptide, a RSK2 polypeptide, or combinations thereof.

In one embodiment, the agent decreases an interaction between a KRC molecule and a Runx2 molecule.

In another embodiment, the agent increases an interaction between a KRC molecule and a Runx2 molecule.

In yet another embodiment, the agent decreases an interaction between a KRC molecule, a SMAD3 molecule, and a Runx2 molecule.

In another embodiment, the agent increases an interaction between a KRC molecule, a SMAD3 molecule, and a Runx2 molecule.

In another embodiment, the agent decreases an interaction between a KRC molecule and a WWP1 molecule.

In one embodiment, the agent increases an interaction between a KRC molecule and a WWP1 molecule.

In another embodiment, the agent decreases an interaction between a KRC molecule, a RSK2 molecule, and a WWP1 molecule.

In one embodiment, the agent increases an interaction between a KRC molecule, a RSK2 molecule, and a WWP 1 molecule.

In yet another embodiment, the agent decreases the ubiquitination of Runx2.

In one embodiment, the agent increases the ubiquitination of Runx2.

In yet another embodiment, the agent decreases the ubiquitination of RSK2.

In one embodiment, the agent increases the ubiquitination of RSK2.

In one embodiment, the osteoblast is further contacted with an agent that decreases the ubiquitination of Runx2.

In one embodiment, the osteoblast is further contacted with an agent that increases the ubiquitination of Runx2.

In one embodiment, the osteoblast is a mature osteoblast.

In another aspect, the invention pertains to a method of identifying compounds useful in increasing bone formation and mineralization comprising, a) providing an indicator composition comprising KRC and Runx2, or biologically active portions thereof;

b) contacting the indicator composition with each member of a library of test compounds;

c) selecting from the library of test compounds a compound of interest that decreases the interaction of KRC and Runx2, or biologically active portions thereof, wherein the ability of the compound to increase bone formation and mineralization is indicated by a decrease in the interaction as compared to the amount of interaction in the absence of the compound.

In still another aspect, the invention pertains to a method of identifying compounds useful in decreasing bone formation and mineralization comprising, a) providing an indicator composition comprising KRC and Runx2, or biologically active portions thereof;

b) contacting the indicator composition with each member of a library of test compounds;

c) selecting from the library of test compounds a compound of interest that increases the interaction of KRC and Runx2, or biologically active portions thereof, wherein the ability of the compound to decrease bone formation and mineralization is indicated by an increase in the interaction as compared to the amount of interaction in the absence of the compound.

In another aspect, the invention pertains to a method of identifying compounds useful in increasing bone formation and mineralization comprising, a) providing an indicator composition comprising KRC and WWP1, or biologically active portions thereof;

b) contacting the indicator composition with each member of a library of test compounds;

c) selecting from the library of test compounds a compound of interest that decreases the interaction of KRC and WWP1, or biologically active portions thereof, wherein the ability of the compound to increase bone formation and mineralization is indicated by a decrease in the interaction as compared to the amount of interaction in the absence of the compound.

In one embodiment, the invention pertains to a method of identifying compounds useful in decreasing bone formation and mineralization comprising, a) providing an indicator composition comprising KRC and WWP1, or biologically active portions thereof;

b) contacting the indicator composition with each member of a library of test compounds;

c) selecting from the library of test compounds a compound of interest that increases the interaction of KRC and WWP 1, or biologically active portions thereof, wherein the ability of the compound to decrease bone formation and mineralization is indicated by an increase in the interaction as compared to the amount of interaction in the absence of the compound.

In one embodiment, the interaction of KRC and the Runx2 molecule is determined by measuring the formation of a complex between KRC and Runx2.

In one embodiment, the indicator composition is a cell comprising a KRC polypeptide and a Runx2 polypeptide, and the effect of the test compound on bone formation and mineralization is determined by measuring the degradation of the Runx2 polypeptide in the presence and absence of the test compound.

In another embodiment, the indicator composition is a cell comprising a KRC polypeptide, a Runx2 polypeptide or biologically active portion thereof, and a reporter gene responsive to the Runx2 polypeptide; and the effect of the test compound on bone formation and mineralization is determined by evaluating the expression of the reporter gene in the presence and absence of the test compound.

In another embodiment, the reporter gene is OSE2-luciferase.

In another embodiment, the interaction of KRC and the WWP1 molecule is determined by measuring the formation of a complex between KRC and WWP1.

In another embodiment, a SMAD3 molecule is also present in the indicator composition.

In another embodiment, a RSK2 molecule is also present in the indicator composition.

In another embodiment, a Runx2 molecule, or biologically active portion thereof, is also present in the indicator composition.

In one embodiment, the biologically active portion of Runx2 comprises the Runt domain.

In one embodiment, the biologically active portion of Runx2 comprises the PPXY domain.

In one embodiment, the interaction is measured by measuring the ubiquitination of the Runx2 molecule.

In still another embodiment, the interaction is measured by measuring Runx2 mRNA production.

In yet another embodiment, the interaction is measured by measuring Runx2 protein levels.

In another embodiment, the interaction is measured by measuring the expression of at least one molecule selected from the group consisting of: BSP, ColI($\alpha$)1, OCN, RANKL, Osterix, RSK2, and ATF4.

In one embodiment, the indicator composition is a cell that expresses a KRC polypeptide.

In one embodiment, the KRC polypeptide is an endogenous polypeptide.

In another embodiment, the KRC polypeptide is an exogenous polypeptide.

In one embodiment, the cell is an osteoblast. In another embodiment, the osteoblast is a mature osteoblast.

In one embodiment, the compound decreases the interaction of Runx2 and CBFβ. In another embodiment, the compound increases the interaction of Runx2 and CBFβ.

DETAILED DESCRIPTION OF THE INVENTION

The present invention is based, at least in part, on the finding that KRC modulates bone formation and mineralization by interacting with Runx2, SMAD3, and/or WWP1. TGF-β signaling in osteoblasts promotes the formation of a multimeric complex between KRC, Runx2, Smad3, and the E3 ubiquitin ligase, WWP1, which inhibits Runx2 function due to the ability of WWP 1 to promote Runx2 polyubiquitination and proteasome-dependent degradation. KRC is an integral and required component of this complex, since its absence in osteoblasts results in elevated levels of Runx2 protein, enhanced Runx2 transcriptional activity, elevated transcription of Runx2 target genes, profoundly increased bone formation in vivo, as well as defective osteoclastogenesis in vivo. The present invention is also based, at least in part, on the discovery that KRC and WWP1 also form a complex with RSK2 which promotes RSK2 phosphorylation and inhibits RSK2 function due to the ability of WWP1 to promote RSK2 ubiquitination.

The KRC protein (for KB binding and putative recognition component of the V(D)J Rss), referred to interchangeably herein as Schnurri-3 (Shn3), is a DNA binding protein comprised of 2282 amino acids. KRC has been found to be present in T cells, B cells, and macrophages. The KRC cDNA sequence is set forth in SEQ ID NO: 1. The amino acid sequence of KRC is set forth in SEQ ID NO:2. KRC is a member of a family of zinc finger proteins that bind to the kB motif (Bachmeyer, C, et al., 1999. *Nuc. Acids. Res.* 27(2):643-648). Zinc finger proteins are divided into three classes represented by KRC and the two MHC Class I gene enhancer binding proteins, MBP1 and MBP2 (Bachmeyer, C, et al., 1999. *Nuc. Acids. Res.* 27(2):643-648).

Zinc finger proteins are identified by the presence of highly conserved Cys2His2 zinc fingers. The zinc fingers are an integral part of the DNA binding structure called the ZAS domain. The ZAS domain is comprised of a pair of zinc fingers, a glutamic acid/aspartic acid-rich acidic sequence and a serine/threonine rich sequence. The ZAS domains have been shown to interact with the kB like cis-acting regulatory elements found in the promoter or enhancer regions of genes. The genes targeted by these zinc finger proteins are mainly involved in immune responses.

The KRC ZAS domain, in particular, has a pair of Cys2-His2 zinc fingers followed by a glutamic acid/aspartic acid-rich acidic sequence and five copies of the serine/threonine-proline-X-arginine/lysine sequence. Southwestern blotting experiments, electrophoretic mobility shift assays (EMSA) and methylation interference analysis has also demonstrated that KRC recombinant proteins bind to the KB motif as well as to the Rss sequence (Bachmeyer, et al. 1999. *Nuc. Acid Res.* 27, 643-648; Wu et al. 1998. *Science* 281, 998-1001) and do so in highly ordered complexes (Mak, C. H., et al. 1994. *Nuc. Acid Res.* 22, 383-390; Wu et al. 1998. *Science* 281, 998-1001).

Similar zinc finger-acidic domain structures are present in human KBP1, MBP1 and MBP2, rat ATBP1 and ATBP2, and mouse αA-CRYBP proteins. KRC has recently been shown to regulate transcription of the mouse metastasis-associated gene, s100A4/1 mts1*, by binding to the Sb element (a kB like sequence) of the gene. (Hjelmsoe, I., et al. 2000. *J. Biol.*

*Chem.* 275(2): 913-920). KRC is regulated by post-translational modification as evidenced by the fact that pre-B cell nuclear protein kinases phosphorylate KRC proteins on serine and tyrosine residues. Phosphorylation increases DNA binding, providing a mechanism by which KRC may respond to signals transmitted from the cell surface (Bachmeyer, C, et al., 1999. *Nuc. Acids. Res.* 27(2):643-648). Two prominent ser/thr-specific protein-kinases that play a central role in signal transduction are cyclic AMP-dependent protein kinase A (PKA) and the protein kinase C (PKC family). Numerous other serine/threonine specific kinases, including the family of mitogen-activated protein (MAP) kinases serve as important signal transduction proteins which are activated in either growth-factor receptor or cytokine receptor signaling. Other protein ser/thr kinases important for intracellular signaling are Calcium-dependent protein kinase (CaM-kinase II) and the c-raf-protooncogene. KRC is known to be a substrate for epidermal growth factor receptor kinase and p34cdc2 kinase in vitro.

The results of a yeast two hybrid screen using amino acid residues 204 to 1055 of KRC (which includes the third zinc finger) as bait demonstrate that KRC interacts with the TRAF family of proteins and that this interaction occurs through the TRAF C domain and that KRC interacts with higher affinity with TRAF2 than with TRAF5 and TRAF6. (See Example 1 of PCT/US02/14166).

Recent research has lead to the isolation of polypeptide factors named TRAFs for tumor necrosis factor receptor associated factors, which participate in the TNFR signal transduction cascade. Six members of the TRAF family of proteins have been identified in mammalian cells (reviewed in Arch, R. H., et al. 1998. *Genes Dev.* 12, 2821-2830). All TRAF proteins, with the exception of TRAF1, contain an amino terminal RING finger domain with a characteristic pattern of cysteines and histidines that coordinate the binding of Zn2+ ions (Borden, K. L. B., et al. 1995. *EMBO J* 14, 1532-1521), which is followed by a stretch of multiple zinc fingers. All TRAFs share a highly conserved carboxy-terminal domain (TRAF-C domain) which is required for receptor binding and can be divided into two parts, a highly conserved domain which mediates homo and heterodimerization of TRAF proteins and also the association of the adapter proteins with their associated receptors and an amino-terminal half that displays a coiled-coil configuration. TRAF molecules have distinct patterns of tissue distribution, are recruited by different cell surface receptors and have distinct functions as revealed most clearly by the analysis of TRAF-deficient mice (see Lomaga, M. A., et al. 1999. *Genes Dev.* 13, 1015-24; Nakano, H., et al. 1999. *Proc. Natl. Acad. Sci. USA* 96, 9803-9808; Nguyen, L. T., et al. 1999. *Immunity* 11, 379-389; Xu, Y., et al. 1996. *Immunity* 5, 407-415; Yeh, W. C., et al. 1997. *Immunity* 7, 715-725).

Tumor necrosis factor (TNF) is a cytokine produced mainly by activated macrophages which elicits a wide range of biological effects. These include an important role in endotoxic shock and in inflammatory, immunoregulatory, proliferative, cytotoxic, and anti-viral activities (reviewed by Goeddel, D. V. et al., 1986. *Cold Spring Harbor Symposia on Quantitative Biology* 51: 597-609; Beutler, B. and Cerami, A., 1988. *Ann. Rev. Biochem.* 57: 505-518; Old, L. J., 1988. *Sci. Am.* 258(5): 59-75; Fiers, W. 1999. *FEBS Lett.* 285(2): 199-212). The induction of the various cellular responses mediated by TNF is initiated by its interaction with two distinct cell surface receptors, an approximately 55 kDa receptor termed TNFR1 and an approximately 75 kDa receptor termed TNFR2. Human and mouse cDNAs corresponding to both receptor types have been isolated and characterized (Loetscher, H. et al., 1990. *Cell* 61:351; Schall, T. J. et al., 1990. *Cell* 61: 361; Smith, C. A. et al., 1990 *Science* 248: 1019; Lewis, M. et al., 1991. *Proc. Natl. Acad. Sci. USA* 88: 2830-2834; Goodwin, R. G. et al., 1991. *Mol. Cell. Biol.* 11:3020-3026).

TNFα binds to two distinct receptors, TNFR1 and TNFR2, but in most cell types NFκB activation and JNK/SAPK activation occur primarily through TNFR1. TNFR1 is known to interact with TRADD which functions as an adaptor protein for the recruitment of other proteins including RIP, a serine threonine kinase, and TRAF2. Of the six known TRAFs, TRAF2, TRAF5 and TRAF6 have all been linked to NFκB activation (Cao, Z., et al. 1996. *Nature* 383: 443-6; Rothe, M., et al. 1994. *Cell* 78: 681-692; Nakano, H., et al. 1996. *J. Biol. Chem.* 271:14661-14664), and TRAF2 in particular has been linked to activation of the JNK/SAPK proteins as shown unequivocally by the failure of TNFα to activate this MAP kinase in cells lacking TRAF2 or expressing a dominant negative form of TRAF2 (Yeh, W. C., et al. 1997. *Immunity* 7: 715-725; Lee, S. Y., et al. 1997. *Immunity* 7:1-20).

Various aspects of the invention are described in further detail in the following subsections:

I. Definitions

As used herein, the term "KRC", used interchangeably with "Shn3" or "schnurri 3", refers to κB binding and putative recognition component of the V(D)J. Rss. The nucleotide sequence of KRC is set forth in SEQ ID NO:1 and the amino acid sequence of KRC is set forth in SEQ ID NO:2. The amino acid sequence of the ZAS domain of KRC is set forth in amino acids 1497-2282 of SEQ ID NO:2 (SEQ ID NO:8). The amino acid sequence of KRC tr is shown in amino acid residues 204 to 1055 of SEQ ID NO:2. As used herein, the term "KRC", unless specifically used to refer to a specific SEQ ID NO, will be understood to refer to a KRC family polypeptide as defined below.

"KRC family polypeptide" is intended to include proteins or nucleic acid molecules having a KRC structural domain or motif and having sufficient amino acid or nucleotide sequence identity with a KRC molecule as defined herein. Such family members can be naturally or non-naturally occurring and can be from the same or different species. For example, a family can contain a first protein of human origin, as well as other, distinct proteins of human origin or, alternatively, can contain homologues of non-human origin. Preferred members of a family may also have common functional characteristics. Preferred KRC polypeptides comprise one or more of the following KRC characteristics: a pair of Cys2-His2 zinc fingers followed by a Glu- and Asp-rich acidic domain and five copies of the ser/Thr-Pro-X-Arg/Lys sequence thought to bind DNA. Another preferred KRC family polypeptide comprises amino acid residues 204 to 1055 of SEQ ID NO:2 (e.g., the "KRC-interacting domain" (KRC tr)).

As used herein, the term "KRC activity", "KRC biological activity" or "activity of a KRC polypeptide" includes the ability to modulate an activity regulated by KRC, a KRC family polypeptide, such as for example KRC tr, or a signal transduction pathway involving KRC. For example, in one embodiment a KRC biological activity includes modulation of an immune response. In another embodiment, KRC modulates bone formation and mineralization. Exemplary KRC activities include e.g., modulating: immune cell activation and/or proliferation (such as by modulating cytokine gene expression), cell survival (e.g., by modulating apoptosis), signal transduction via a signaling pathway (e.g., an NFκB signaling pathway, a JNK signaling pathway, and/or a TGFβ signaling pathway), actin polymerization, ubiquitination of AP-1, ubiquitination of TRAF, degradation of c-Jun, degradation of c-Fos, degradation of SMAD, degradation of GATA3, GATA3 expression, modulation of Th2 cell differentiation, modulation of Th2 cytokine production, IgA production, modulation of GLα transcription, modulation of bone growth, modulation of bone mineralization, modulation of osteoclastogenesis, modulation of osteoblast versus osteoclast activity, e.g., in bone formation and/or remodeling of bone, modulation of osteocalcin gene transcription, degradation of Runx2, e.g., modulation of Runx2 protein levels, ubiquitination of Runx2, modulation of the expression of RSK2, degradation of RSK2, e.g., modulation of RSK2 protein levels, ubiquitination of RSK2, modulation of the phosphorylation of RSK2, modulation of the expression of BSP, ColI(α)1, OCN, Osterix, RANKL, and ATF4, modulation of ATF4 protein levels, and/or modulation of the phosphorylation of ATF4.

As used herein, the various forms of the term "modulate" are intended to include stimulation (e.g., increasing or upregulating a particular response or activity) and inhibition (e.g., decreasing or downregulating a particular response or activity).

As described above and in the appended Examples, KRC modulates bone formation and mineralization through a complex interaction of molecules which are downstream of TGF-β signaling. In one embodiment, the KRC activity is a direct activity, such as an association with a KRC-target molecule or binding partner. As used herein, a "target molecule", "binding partner" or "KRC binding partner" is a molecule with which a KRC protein binds or interacts in nature, such that KRC mediated function is achieved.

As used herein the term "TRAF" refers to TNF Receptor Associated Factor (See e.g., Wajant et al, 1999, *Cytokine Growth Factor Rev* 10:15-26). The "TRAF" family includes a family of cytoplasmic adapter proteins that mediate signal transduction from many members of the TNF-receptor super-family and the interleukin-1 receptor (see e.g., Arch, R. H. et al., 1998, *Genes Dev.* 12:2821-2830). As used herein, the term "TRAF C domain" refers to the highly conserved sequence motif found in TRAF family members.

As used herein, the terms "TRAF interacting portion of a KRC molecule" or "c-Jun interacting portion of a KRC molecule" includes a region of KRC that interacts with TRAF or c-Jun. In a preferred embodiment, a region of KRC that interacts with TRAF or c-Jun is amino acid residues 204-1055 of SEQ ID NO:2 (SEQ ID NO:7). As used herein, the term "KRC interacting portion of a TRAF molecule" or "KRC interacting portion of a TRAF molecule" includes a region of TRAF or c-Jun that interacts with KRC. In a preferred embodiment, a region of TRAF that interacts with KRC is the TRAF C domain.

The term "interact" as used herein is meant to include detectable interactions between molecules, such as can be detected using, for example, a yeast two hybrid assay or coimmunoprecipitation. The term interact is also meant to include "binding" interactions between molecules. Interactions may be protein-protein or protein-nucleic acid in nature.

As used herein, the term "contacting" (i.e., contacting a cell e.g. an immune cell, with an compound) is intended to include incubating the compound and the cell together in vitro (e.g., adding the compound to cells in culture) or administering the compound to a subject such that the compound and cells of the subject are contacted in vivo. The term "contacting" is not intended to include exposure of cells to a KRC modulator that may occur naturally in a subject (i.e., exposure that may occur as a result of a natural physiological process).

As used herein, the term "test compound" includes a compound that has not previously been identified as, or recognized to be, a modulator of KRC activity and/or expression and/or a modulator of bone growth and/or mineralization.

The term "library of test compounds" is intended to refer to a panel or pool comprising a multiplicity of test compounds.

As used herein, the term "cell free composition" refers to an isolated composition which does not contain intact cells. Examples of cell free compositions include cell extracts and compositions containing isolated proteins.

As used herein, the term "indicator composition" refers to a composition that includes a protein of interest (e.g., KRC or a molecule in a signal transduction pathway involving KRC), for example, a cell that naturally expresses the protein, a cell that has been engineered to express the protein by introducing an expression vector encoding the protein into the cell, or a cell free composition that contains the protein (e.g., purified naturally-occurring protein or recombinantly-engineered protein).

As used herein, an "antisense" nucleic acid comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid can hydrogen bond to a sense nucleic acid.

In one embodiment, nucleic acid molecule of the invention is an siRNA molecule. In one embodiment, a nucleic acid molecule of the invention mediates RNAi. RNA interference (RNAi) is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. *Cell* 101, 25-33 (2000). Tuschl, T. et al. *Genes Dev.* 13, 3191-3197 (1999); Cottrell T R, and Doering T L. 2003. Trends Microbiol. 11:37-43; Bushman F. 2003. Mol. Therapy. 7:9-10; McManus M T and Sharp P A. 2002. Nat Rev Genet. 3:737-47). The process occurs when an endogenous ribonuclease cleaves the longer dsRNA into shorter, e.g., 21- or 22-nucleotide-long RNAs, termed small interfering RNAs or siRNAs. The smaller RNA segments then mediate the degradation of the target mRNA. Kits for synthesis of RNAi are commercially available from, e.g. New England Biolabs or Ambion. In one embodiment one or more of the chemistries described herein for use in antisense RNA can be employed in molecules that mediate RNAi.

As used herein, the term "dominant negative" includes molecules, such as KRC molecules (e.g., portions or variants thereof) that compete with native (i.e., wild-type) KRC molecules, but which do not have KRC activity. Such molecules effectively decrease KRC activity in a cell.

As used herein, the term "NFkB signaling pathway" refers to any one of the signaling pathways known in the art which involve activation or deactivation of the transcription factor NFkB, and which are at least partially mediated by the NFkB factor (Karin, 1998, *Cancer J from Scientific American*, 4:92-99; Wallach et al, 1999, *Ann Rev of Immunology*, 17:331-367). Generally, NFkB signaling pathways are responsive to a number of extracellular influences e.g. mitogens, cytokines, stress, and the like. The NFkB signaling pathways involve a range of cellular processes, including, but not limited to, modulation of apoptosis. These signaling pathways often comprise, but are by no means limited to, mechanisms which involve the activation or deactivation via phosphorylation state of an inhibitor peptide of NFkB (IkB), thus indirectly activating or deactivating NFkB.

As used herein, the term "JNK signaling pathway" refers to any one of the signaling pathways known in the art which involve the Jun amino terminal kinase (JNK) (Karin, 1998, *Cancer J from Scientific American*, 4:92-99; Wallach et al, 1999, *Ann Rev of Immunology*, 17:331-367). This kinase is generally responsive to a number of extracellular signals e.g. mitogens, cytokines, stress, and the like. The JNK signaling pathways mediate a range of cellular processes, including, but not limited to, modulation of apoptosis. In a preferred embodiment, JNK activation occurs through the activity of one or more members of the TRAF protein family (See, e.g., Wajant et al, 1999, *Cytokine Growth Factor Rev* 10:15-26).

As used herein, the term "TGFβ signaling pathway" refers to any one of the signaling pathways known in the art which involve transforming growth factor beta. A TGFβ signaling pathway is initiated when this molecule binds to and induces a heterodimeric cell-surface complex consisting of type I (TβRI) and type II (TβRII) serine/threonine kinase receptors. This heterodimeric receptor then propagates the signal through phosphorylation of downstream target SMAD proteins. There are three functional classes of SMAD protein, receptor-regulated SMADs (R-SMADs), e.g. SMAD2 and SMAD3, Co-mediator SMADs (Co-SMADs) and inhibitory SMADs (I-SMADs). Following phosphorylation by the heterodimeric receptor complex, the R-SMADs complex with the Co-SMAD and translocate to the nucleus, where in conjunction with other nuclear proteins, they regulate the transcription of target genes (Derynck, R., et al. (1998) *Cell* 95: 737-740). Reviewed in Massague, J. and Wotton, D. (2000) *EMBO J.* 19:1745.

The nucleotide sequence and amino acid sequence of human SMAD2, is described in, for example, GenBank Accession No. gi:20127489. The nucleotide sequence and amino acid sequence of murine SMAD2, is described in, for example, GenBank Accession No. gi:31560567. The nucleotide sequence and amino acid sequence of human SMAD3, is described in, for example, GenBank Accession No. gi:42476202. The nucleotide sequence and amino acid sequence of murine SMAD3, is described in, for example, GenBank Accession No. gi:31543221.

"GATA3" is a Th2-specific transcription factor that is required for the development of Th2 cells. GATA-binding proteins constitute a family of transcription factors that recognize a target site conforming to the consensus WGATAR (W=A or T and R=A or G). GATA3 interacts with SMAD3 following its phosphorylation by TGFβ signaling to induce the differentiation of T helper cells. The nucleotide sequence and amino acid sequence of human GATA3, is described in, for example, GenBank Accession Nos. gi:4503928 and gi:14249369. The nucleotide sequence and amino acid sequence of murine GATA3, is described in, for example, GenBank Accession No. gi:40254638. The domains of GATA3 responsible for specific DNA-binding site recognition (amino acids 303 to 348) and trans activation (amino acids 30 to 74) have been identified. The signaling sequence for nuclear localization of human GATA-3 is a property conferred by sequences within and surrounding the amino finger (amino acids 249 to 311) of the protein. Exemplary genes whose transcription is regulated by GATA3 include IL-1, IL-12, IL-13, and IL-12Rβ2.

TGFβ also plays a key role in osteoblast differentiation and bone development and remodeling. Osteoblasts secrete and deposit TGFβ into the bone matrix and can respond to it, thus enabling possible autocrine modes of action. TGFβ regulates the proliferation and differentiation of osteoblasts both in vitro and in vivo; however, the effects of TGFβ on osteoblast differentiation depend on the extracellular milieu and the differentiation stage of the cells. TGFβ stimulates proliferation and early osteoblast differentiation, while inhibiting terminal differentiation. Accordingly, TGFβ has been reported to inhibit expression of alkaline phosphatase and osteocalcin, among other markers of osteoblast differentiation and function (Centrella et al., 1994 Endocr. Rev., 15, 27-39). Osteoblasts express cell surface receptors for TGFβ and the effectors, Smad2 and Smad3.

As used herein, the term "bone formation and mineralization" refers to the cellular activity of osteoblasts to synthesize the collagenous precursors of bone extracellular matrix, regulate mineralization of the matrix to form bone, as well as their function in bone remodeling and reformation, e.g., bone mass is maintained by a balance between the activity of osteoblasts that form bone and the osteoclasts that break it down. The mineralization of bone occurs by deposition of carbonated hydroxyapetite crystals in an extracellular matrix consisting of type I collagen and a variety of non-collagenous proteins. As used herein, an "osteoblast" is a bone-forming cell that is derived from mesenchymal osteoprognitor cells and forms an osseous matrix in which it becomes enclosed as an osteocyte. A mature osteoblast is one capable of forming bone extracellular matrix in vivo, and can be identified in vitro by its capacity to form mineralized nodules which reflects the generation of extracellular. An immature osteoblast is not capable of forming mineralized nodules in vitro. As used herein, an "osteoclast" is a large multinucleated cell with abundant acidophilic cytoplasm, functioning in the absorption and removal of osseous tissue. Osteoclasts become highly active in the presence of parathyroid hormone, causing increased bone resorption and release of bone salts (phosphorus and, especially, calcium) into the extracellular fluid.

As used herein, "osteocalcin", also called bone Gla protein, is a vitamin K-dependent, calcium-binding bone protein, the most abundant noncollagen protein in bone. Osteocalcin is specifically expressed in differentiated osteoblasts and odontoblasts. The TGF-β-mediated decrease of osteocalcin has been shown to occur at the mRNA level and does not require new protein synthesis. Transcription from the osteocalcin promoter requires binding of the transcription factor CBFA1, also known as Runx2, to a response element, named OSE2, in the osteocalcin promoter.

Runx factors are DNA binding proteins that can facilitate tissue-specific gene activation or repression (Lutterbach, B., and S. W. Hiebert. (2000) Gene 245:223-235). Mammalian Runx-related genes are essential for blood, skeletal, and gastric development and are commonly mutated in acute leukemias and gastric cancers (Lund, A. H., and M. van Lohuizen. (2002) Cancer Cell. 1:213-215). Runx factors exhibit a tissue-restricted pattern of expression and are required for definitive hematopoiesis and osteoblast maturation. Runx proteins have recently been shown to interact through their C-terminal segment with Smads, a family of signaling proteins that regulate a diverse array of developmental and biological processes in response to transforming growth factor (TGF)-β/bone morphogenetic protein (BMP) family of growth factors. Moreover, subnuclear distribution of Runx proteins is mediated by the nuclear matrix-targeting signal, a protein motif present in the C terminus of Runx factors. Importantly, in vivo osteogenesis requires the C terminus of Runx2 containing the overlapping subnuclear targeting signal and the Smad interacting domain. The Runx and Smad proteins are jointly involved in the regulation of phenotypic gene expression and lineage commitment. Gene ablation studies have revealed that both Runx proteins and Smads are developmentally involved in hematopoiesis and osteogenesis. Furthermore, Runx2 and the BMP-responsive Smads can induce osteogenesis in mesenchymal pluripotent cells.

"Runx2" is one of three mammalian homologues of the Drosophila transcription factors, Runt and Lozenge (Daga, A., et al. (1996) Genes Dev. 10:1194-1205). Runx2 is also expressed in T lymphocytes and cooperates with oncogenes c-myc, p53, and Pim1 to accelerate T-cell lymphoma development in mice (Blyth, K, et al. (2001) Oncogene 20:295-302).

Runx2 expression also plays a key role in osteoblast differentiation and skeletal formation. In addition to osteocalcin, Runx2 regulates expression of several other genes that are activated during osteoblast differentiation, including alkaline phosphatase, collagen, osteopontin, and osteoprotegerin ligand. These genes also contain Runx2-binding sites in their promoters. These observations suggest that Runx2 is an essential transcription factor for osteoblast differentiation. This hypothesis is strongly supported by the absence of bone formation in mouse embryos in which the cbfa1 gene was inactivated. Furthermore, cleidocranial dysplasia, a human disorder in which some bones are not fully developed, has been associated with mutations in a cbfa1 allele. In addition to its role in osteoblast differentiation, Runx2 has been implicated in the regulation of bone matrix deposition by differentiated osteoblasts. The expression of Runx2 is regulated by factors that influence osteoblast differentiation. Accordingly, BMPs can activate, while Smad2 and glucocorticoids can inhibit, Runx2 expression. In addition, Runx2 can bind to an OSE2 element in its own promoter, suggesting the existence of an autoregulatory feedback mechanism of transcriptional regulation during osteoblast differentiation. For a review, see, Alliston, et al. (2000) EMBO J 20:2254.

As described herein, Runx2 interacts with KRC through its Runt DNA binding domain. The best-described binding partner for the Runt domain of Runx2 is CBFβ, a constitutively-expressed factor required for high-affinity DNA binding by Runx2 (Tang, Y. Y., et al. (2000). J Biol Chem 275, 39579-39588; Yoshida, C. A., et al. (2002). Nat Genet 32, 633-638). Although CBFβ−/− mice die at E12.5 due to severe defects in Runx1-mediated hematopoiesis, when CBFβ−/− mice are rescued by transgenic overexpression of CBFβ by the Gata1 promoter, severe dwarfism results that mimicking the phenotype of Runx2−/− mice (Yoshida, C. A., et al. (2002). Nat Genet. 32, 633-638). When bound to CBFβ, Runx family members are protected from ubiquitin/proteasome-mediated degradation (Huang, G., et al. (2001). Embo J 20, 723-733). When bound to CBFβ, Runx2 stability is promoted and it optimally binds target DNA sequences. When bound to Shn3, Runx2 can no longer bind target sequences with high affinity, and Runx2 degradation is accelerated due to enhanced ubiquitination and subsequent proteolysis.

The nucleotide sequence and amino acid sequence of human Runx2, is described in, for example, GenBank Accession No. gi:10863884. The nucleotide sequence and amino acid sequence of murine Runx2, is described in, for example, GenBank Accession No. gi:20806529. The nucleotide sequence and amino acid sequence of human CBFβ, is described in, for example, GenBank Accession No. gi: 47132615 and 47132616. The nucleotide sequence and amino acid sequence of murine CBFβ, is described in, for example, GenBank Accession No. gi: gi:31981853.

As used herein, "WWP1" is a member of the family of E3 ubiquitin ligases with multiple WW domains, which also includes Nedd4, WWP2, and AIP4. WWP1 has previously been shown to interact with all R- and I-Smad proteins, and to promote the ubiquitination of Smad6 and Smad7 (Komuro, A., et al. (2004). *Oncogene* 23, 6914-6923); however, the ability of WWP1 to ubiquitinate Runx proteins, which also possess PPXY motifs in their Runt domains (Jin, Y. H., et al. (2004). *J Biol Chem* 279, 29409-29417), had not been investigated.

The nucleotide sequence and amino acid sequence of human WWP1, is described in, for example, GenBank Accession No. gi:33946331. The nucleotide sequence and amino acid sequence of murine WWP 1, is described in, for example, GenBank Accession No. gi:51709071.

"Bone sialoprotein" or "BSP" is belongs to the osteopontin gene family and is a non-collagenouse bone matrix protein that binds tightly to hydroxyapatite, forming an integral part of the mineralized matrix of bone. The nucleotide sequence and amino acid sequence of human BSP, is described in, for example, GenBank Accession No. gi:38146097. The nucleotide sequence and amino acid sequence of murine BSP, is described in, for example, GenBank Accession No. gi:6678112.

Type I collagen ($\alpha$)1 ("ColI($\alpha$)1"), is a collagenouse bone matrix protein. The nucleotide sequence and amino acid sequence of human ColI($\alpha$)1, is described in, for example, GenBank Accession No. gi:14719826. The nucleotide sequence and amino acid sequence of murine ColI($\alpha$)1, is described in, for example, GenBank Accession No. gi:34328107.

"ATF4", also called "CREB2", and "Osterix", also called "SP7", are transcription factors belonging to the bZIP protein family and C2H2-type zinc-finger protein family, respectively, that are key regulators of bone matrix biosynthesis during remodeling of bone, e.g., during bone formation and mineralization (see, for example, Yang, X., et al. (2004). *Cell* 117, 387-398; Nakashima, K., et al. (2002). *Cell* 108, 17-2). BSP, ColI($\alpha$)1, ATF4, and Osterix are specific markers of bone formation and development. The nucleotide sequence and amino acid sequence of human ATF4, is described in, for example, GenBank Accession No. gi:33469975 and gi:33469973. The nucleotide sequence and amino acid sequence of murine ATF4, is described in, for example, GenBank Accession No. gi:6753127. The nucleotide sequence and amino acid sequence of human SP7, is described in, for example, GenBank Accession No. gi:22902135. The nucleotide sequence and amino acid sequence of murine SP7, is described in, for example, GenBank Accession No gi:18485517.

As used herein, the term "ATF4 signaling pathway" refers to any one of the signaling pathways known in the art which involve Activating Transcription Factor 4 to regulate osteoblast development and function. As discussed above, ATF4 is a transcription factor which functions as a specific repressor of CRE-dependent transcription. The transcriptional repressor activity resides within the C-terminal leucine zipper and basic domain region of the ATF4 protein. ATF4 has been shown to be required for high levels of collagen synthesis by mature osteoblasts and requires phosphorylation by the kinase, RSK2, for optimal extracellular matrix production by osteoblasts (Yang, et al. (2004) *Cell* 117:387). Furthermore, as described herein, animals deficient in KRC have elevated levels of ATF4 and RSK2 mRNA and protein, as well as an accumulation of hyperphosphorylated ATF4. The nucleotide sequence and amino acid sequence of human RSK2, is described in, for example, GenBank Accession No. gi:56243494. The nucleotide sequence and amino acid sequence of murine Rsk2, is described in, for example, GenBank Accession No. gi:22507356.

As used herein, "AP-1" refers to the transcription factor activator protein 1 (AP-1) which is a family of DNA-binding factors that are composed of dimers of two proteins that bind to one another via a leucine zipper motif. The best characterized AP-1 factor comprises the proteins Fos and Jun. (Angel, P. and Karin, M. (1991) *Biochim. Biophys. Acta* 1072:129-157; Orengo, I. F., Black, H. S., et al. (1989) *Photochem. Photobiol.* 49:71-77; Curran, T. and Franza, B. R., Jr. (1988) *Cell* 55, 395-397). The AP-1 dimers bind to and transactivate promoter regions on DNA that contain cis-acting phorbol 12-tetradecanoate 13-acetate (TPA) response elements to induce transcription of genes involved in cell proliferation, metastasis, and cellular metabolism (Angel, P., et al. (1987) *Cell* 49, 729-739. AP-1 is induced by a variety of stimuli and is implicated in the development of cancer and autoimmune disease. The nucleotide sequence and amino acid sequence of human AP-1, is described in, for example, GenBank Accession No. gi:20127489.

As used herein, the term "nucleic acid" includes fragments or equivalents thereof (e.g., fragments or equivalents thereof KRC, TRAF, c-Jun, c-Fos, GATA3, Runx2, SMAD2, SMAD3, GL$\alpha$, CBF$\beta$, ATF4, RSK2, and/or WWP1). The term "equivalent" is intended to include nucleotide sequences encoding functionally equivalent proteins, i.e., KRC variant proteins which have the ability to bind to the natural binding partner(s) of the KRC or variant proteins in a signal transduction pathway involving KRC that retain their biological activity. In a preferred embodiment, a functionally equivalent KRC protein has the ability to bind TRAF, e.g., TRAF2, in the cytoplasm of an immune cell, e.g., a T cell. In another preferred embodiment, a functionally equivalent KRC protein has the ability to bind Jun, e.g., c-Jun, in the nucleoplasm of an immune cell, e.g., a T cell. In another preferred embodiment, a functionally equivalent KRC protein has the ability to bind GATA3 in the nucleoplasm of an immune cell, e.g., a T cell. In yet another preferred embodiment, a functionally equivalent KRC protein has the ability to bind SMAD, e.g., SMAD2 and/or SMAD3, in the cytoplasm of an immune cell, e.g., a B cell. In yet another preferred embodiment, a functionally equivalent KRC protein has the ability to bind SMAD3 in the cytoplasm of an osteoblast. In yet another preferred embodiment, a functionally equivalent KRC has the ability to bind Runx2 in the nucleoplasm of an immune cell, e.g. a B cell. In another preferred embodiment, a functionally equivalent KRC has the ability to bind Runx2. In yet another preferred embodiment, a functionally equivalent KRC has the ability to bind WWP 1. In yet another preferred embodiment, a functionally equivalent KRC has the ability to bind SMAD3, Runx2, and/or WWP1. In another preferred embodiment, a functional equivalent of a KRC molecule comprises a PPXY motif and has the ability to bind WWP1. In another preferred embodiment, a functional equivalent of a Runx2 molecule comprises the Runt domain, e.g., amino acids 102-229 of Runx2, and has the ability to bind KRC. In another preferred embodiment, a functional equivalent of a Runx2 molecule comprises a PPXY motif in its Runt domain, e.g., amino acids 102-229 of Runx2, and has the ability to bind WWP1. In yet another preferred embodiment, a functionally equivalent KRC has the ability to bind RSK2 and/or WWP1.

An "isolated" nucleic acid molecule is one which is separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid molecule is free of sequences which naturally flank the nucleic acid molecule (i.e., sequences located at the 5' and 3' ends of the nucleic acid molecule) in the genomic DNA of the organism from which the nucleic acid molecule is derived.

As used herein, an "isolated protein" or "isolated polypeptide" refers to a protein or polypeptide that is substantially free of other proteins, polypeptides, cellular material and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the KRC protein is derived, or substantially free from chemical precursors or other chemicals when chemically synthesized. The language "substantially free of cellular material" includes preparations of KRC protein in which the protein is separated from cellular components of the cells from which it is isolated or recombinantly produced.

The nucleic acids of the invention can be prepared, e.g., by standard recombinant DNA techniques. A nucleic acid of the invention can also be chemically synthesized using standard techniques. Various methods of chemically synthesizing polydeoxynucleotides are known, including solid-phase synthesis which has been automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

As used herein, the term "host cell" is intended to refer to a cell into which a nucleic acid molecule of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. Preferably a host cell is a mammalian cell, e.g., a human cell. In particularly preferred embodiments, it is a epithelial cell.

As used herein, the term "transgenic cell" refers to a cell containing a transgene.

As used herein, a "transgenic animal" includes an animal, e.g., a non-human mammal, e.g., a swine, a monkey, a goat, or a rodent, e.g., a mouse, in which one or more, and preferably essentially all, of the cells of the animal include a transgene. The transgene is introduced into the cell, directly or indirectly by introduction into a precursor of the cell, e.g., by microinjection, transfection or infection, e.g., by infection with a recombinant virus. The term genetic manipulation includes the introduction of a recombinant DNA molecule. This molecule may be integrated within a chromosome, or it may be extrachromosomally replicating DNA.

As used herein, the term "antibody" is intended to include immunoglobulin molecules and immunologically active portions of immunoglobulin molecules, i.e., molecules that contain an antigen binding site which binds (immunoreacts with) an antigen, such as Fab and F(ab')$_2$ fragments, single chain antibodies, intracellular antibodies, scFv, Fd, or other fragments, as well as intracellular antibodies. Preferably, antibodies of the invention bind specifically or substantially specifically to KRC, TRAF, c-Jun, c-Fos, GATA3, SMAD2, SMAD3, CBFβ, ATF4, RSK2, WWP 1 or Runx2, molecules (i.e., have little to no cross reactivity with non-KRC, non-TRAF, non-c-Jun, non-c-Fos, non-GATA3, non-SMAD2, non-SMAD3, non-WWP1, non-CBFβ, non-ATF4, non-RSK2, or non-Runx2, molecules). The terms "monoclonal antibodies" and "monoclonal antibody composition", as used herein, refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody compositions thus typically display a single binding affinity for a particular antigen with which it immunoreacts.

As used herein, the term "disorders that would benefit from the modulation of KRC activity or expression" or "KRC associated disorder" includes disorders in which KRC activity is aberrant or which would benefit from modulation of a KRC activity. Exemplary KRC associated disorders include disorders, diseases, conditions or injuries in which modulation of bone formation and mineralization would be beneficial.

In one embodiment, small molecules can be used as test compounds. The term "small molecule" is a term of the art and includes molecules that are less than about 7500, less than about 5000, less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., Cane et al. 1998. Science 282:63), and natural product extract libraries. In another embodiment, the compounds are small, organic non-peptidic compounds. In a further embodiment, a small molecule is not biosynthetic. For example, a small molecule is preferably not itself the product of transcription or translation.

Various aspects of the invention are described in further detail below:

II. Methods for Modulating Biological Responses Regulated by KRC

The present invention provides for both prophylactic and therapeutic methods of treating a subject at risk of (or susceptible to) a disorder or having a disorder associated with aberrant KRC expression and/or activity. For example, a disease, disorder, condition or injury that would benefit from increased or decreased bone formation and mineralization, as described herein.

Subjects at risk for such disorders can be identified by, for example, any or a combination of diagnostic or prognostic assays known in the art. Administration of a prophylactic agent can occur prior to the manifestation of symptoms, such that a disease, disorder, condition, or injury is prevented or, alternatively, delayed in its progression. Depending on the type of aberrancy, for example, a KRC antagonist or agonist agent can be used for treating a subject. The appropriate agent can be determined based on screening assays described herein.

Another aspect of the invention pertains to methods of modulating KRC activity for therapeutic purposes. KRC activity can be modulated in order to modulate bone formation and mineralization. KRC inhibits bone formation and mineralization, therefore decreasing KRC expression and/or biological activity results in increasing bone formation and mineralization. Conversely, increasing KRC expression and/or biological activity would result in decreased bone formation and mineralization.

Modulatory methods of the invention involve contacting a cell (e.g. a T cell B cell, and/or osteoblast, e.g., a mature osteoblast) with an agent that modulates the expression and/or biological activity of KRC. An agent that modulates KRC activity can be an agent as described herein, such as a KRC peptide (e.g., the agent may be a peptide comprising the amino acid residues 204-1055 of KRC, a peptide that binds to KRC, a KRC ZAS domain or a small molecule), a nucleic acid molecule encoding one of the aforementioned peptides, a KRC agonist or antagonist, a peptidomimetic of a KRC agonist or antagonist, a KRC peptidomimetic, or other small molecule identified using the screening methods described herein. Additional agents include, but are not limited to a nucleic acid molecule that is antisense to a KRC molecule, a nucleic acid molecule that is antisense to a SMAD3 molecule, a nucleic acid molecule that is antisense to a RUNX2 molecule, a nucleic acid molecule that is antisense to a WWP 1 molecule, a nucleic acid molecule that is antisense to a RSK2 molecule, a KRC siRNA molecule, a SMAD3 siRNA molecule, a RUNX2 siRNA molecule, a WWP 1 siRNA molecule, a RSK2 siRNA molecule, a dominant negative KRC molecule, a dominant negative SMAD3 molecule, a dominant negative Runx2 molecule, a dominant negative WWP1 molecule, a dominant negative RSK2 molecule, a SMAD3 polypeptide, a Runx2 polypeptide, a WWP1 polypeptide, a RSK2 polypeptide, or combinations thereof.

These modulatory methods can be performed in vitro (e.g., by contacting the cell with the agent) or, alternatively, in vivo (e.g., by administering the agent to a subject). Furthermore, the modulatory methods of the invention can be performed on a surface, in vitro or in vivo. For example, the surface of a surgically implanted, rod, pin, plate, screw, or other implement implanted for the purpose of stabilizing, repairing a bone, e.g., a fracture, a joint, a tooth, or a joint replacement, or a tooth replacement, may be treated with an agent of the invention such that bone formation and mineralization is modulated, e.g., enhanced or increased. As such, the present invention provides methods of treating an individual afflicted with a disease, condition, disorder or injury that would benefit from up- or down-modulation of a KRC polypeptide, e.g., a disorder characterized by an unwanted, insufficient, or aberrant immune response, or one in which modulation of bone formation and mineralization would be beneficial. In one embodiment, the method involves administering an agent (e.g., an agent identified by a screening assay described herein), or combination of agents that modulates (e.g., upregulates or downregulates) KRC expression or biological activity, as described herein.

Inhibition of KRC activity is desirable in situations in which KRC is abnormally upregulated and/or in which decreased KRC activity is likely to have a beneficial effect, for example in a situation when increased bone formation and mineralization is desirable. Such situations include conditions, disorders, diseases, or injuries include but are not limited to, for example, osteoporosis, osteomalacia, skeletal changes of hyperparathyroidism and chronic renal failure (renal osteodystrophy) and osteitis deformans (Paget's disease of bone).

Exemplary agents for use in upmodulating KRC (i.e., agonists) include, e.g., nucleic acid molecules encoding KRC, SMAD3, RUNX2, RSK2, and/or WWP1 polypeptides, KRC, SMAD3, RUNX2, RSK2, and/or WWP1 peptides, and compounds that stimulate the interaction of KRC with TRAF, GATA3, SMAD2, SMAD3, Runx2, GLα, c-Jun, CBFβ, RSK2, WWP1, for example (e.g., compounds identified in the subject screening assays).

Exemplary agents for use in downmodulating KRC (i.e., antagonists) include agents that inhibit the activity of KRC in cell, for example, nucleic acid molecules that are antisense to a KRC, SMAD3, RUNX2, RSK2, or WWP1 molecule, a KRC, SMAD3, RUNX2, RSK2, or WWP1 siRNA molecule, a dominant negative KRC, SMAD3, RUNX2, RSK2, or WWP 1 molecule, or combinations thereof (e.g., compounds identified in the subject screening assays).

A. Downregulation of KRC Biological Activities

There are numerous embodiments of the invention for downregulating the function of a KRC polypeptide to thereby upregulate or promote bone formation and mineralization. Downregulating the function of KRC can be in the form of promoting or increasing bone formation and mineralization prior to development of a condition or injury (e.g., in a subject diagnosed as likely to develop a condition that would benefit from increased bone growth or mineralization, such as for example a premenopausal woman) or may involve promoting the induction of bone formation and mineralization to treat, for example a bone fracture or break, an tooth replacement, either replacement of a subjects' own tooth or a prosthetic tooth, or ameliorate symptoms of an ongoing condition, such as for example, bone loss associated with, for example perimenopause or menopause. The functions of osteoblasts and/or activated immune cells can be modulated accordingly by upregulating bone formation and mineralization and/or downregulating immune cell responses, or by inducing specific anergy in immune cells, or both.

For example, KRC activity can be inhibited by contacting a cell which expresses KRC with an agent that inhibits the expression or activity of KRC. Such an agent can be a compound identified by the screening assays described herein. In another embodiment, the agent is a peptide. In a preferred embodiment, the agent can interact with the amino acid residues 204-1055 of KRC to inhibit KRC activity.

Agents that inhibit a KRC activity can be identified by their ability to inhibit immune cell proliferation and/or effector function, or to induce anergy when added to an in vitro assay. A number of art-recognized readouts of cell activation can be employed to measure, e.g., cell proliferation or effector function (e.g., cytokine production or phagocytosis) in the presence of the activating agent. The ability of a test agent to block this activation can be readily determined by measuring the ability of the agent to effect a decrease in proliferation or effector function being measured.

In another aspect of the invention, agents that inhibit a KRC activity can be identified by their ability to increase bone formation and mineralization. A number of art-recognized in vitro and in vivo assays of bone formation and mineralization can be employed to measure, e.g., osteoblast and osteoclast function using assays known in the art and described in more detail herein.

In another embodiment, bone formation and mineralization can be increased in a subject by removing osteoblasts, e.g., mature osteoblasts, from the patient, contacting the osteoblasts in vitro with an agent (e.g., a small molecule) that downregulates KRC activity, and reintroducing the in vitro-treated osteoblasts into the patient.

Increasing bone formation and mineralization by inhibiting KRC activity is useful in situations in which increased bone formation and mineralization would be beneficial. For example, osteoporosis, including idiopathic osteoporosis, secondary osteoporosis, transient osteoporosis of the hip, osteomalacia, Paget's disease of bone, and osteopenia in which there is progressive loss of bone density and thinning of bone tissue are conditions which would benefit from increased bone formation and mineralization such that breaks and/or fractures would not occur. Osteoporosis and osteopenia can result not only from aging and reproductive status, but can also be secondary to numerous diseases and disorders, as well as due to prolonged use of numerous medications, e.g., anticonvulsants (e.g., for epilepsy), corticosteroids (e.g., for rheumatoid arthritis and asthma), and/or immunosuppressive agents (e.g., for cancer). For example, glucocorticoid-induced osteoporosis is a form of osteoporosis that is caused by taking glucocorticoid medications such as prednisone (Deltasone, Orasone, etc.), prednisolone (Prelone), dexamethasone (Decadron, Hexadrol), and cortisone (Cortone Acetate). These medications are frequently used to help control many rheumatic diseases, including rheumatoid arthritis, systemic lupus erythematosus, inflammatory bowel disease, and polymyalgia rheumatica. Other diseases in which osteoporosis may be secondary include, but are not limited to, juvenile rheumatoid arthritis, diabetes, osteogenesis imperfecta, hyperthyroidism, hyperparathyroidism, Cushing's syndrome, malabsorption syndromes, anorexia nervosa and/or kidney disease. In addition, numerous behaviors have been associated with osteoporosis, such as, prolonged inactivity or immobility, inadequate nutrition (especially calcium, vitamin D), excessive exercise leading to amenorrhea (absence of periods), smoking, and/or alcohol abuse.

The administration of a molecule which inhibits the activity of KRC, e.g., by blocking the interaction of KRC with, for example, TRAP, Jun, GATA3, SMAD2, SMAD3, CBFβ, WWP1, RSK2, and/or Runx2, in osteoblasts, e.g. mature osteoblasts (such as a KRC, TRAF, Jun, GATA3, SMAD2, SMAD3, CBFβ, WWP1, RSK2, and/or Runx2 peptide or a small molecule) alone or in conjunction with another downmodulatory agent can increase bone formation and mineralization.

Other modulatory methods and/or agents that can be used in connection with the downmodulatory methods of the invention to increase bone formation and mineralization, include for example, surgery, Op-1$^R$, also known as BMP-7, a member of the Bone Morphogenetic Protein superfamily, BMP-2, vitamin D, calcium, hormone replacement therapy, bisphosphonates, e.g., analogues of endogenous pyrophosphates which inhibit bone resorption, such as, for example, alendronate, etidronate, pamidronate, Calcitonin, Clodronate, selective estrogen receptor modulators (SERMs), e.g., raloxifene, parathyroid hormone, e.g., teriparatide, fluoride, strontium ranelate, TNF-alpha antibodies, osteoprotegerin, beta-Cryptoxanthin, and thiazides can decrease urinary calcium excretion and slow bone loss, tyrosine phosphatase inhibitors, e.g., sodium orthovanadate, alfacalcidol, menatetrenone, statins, e.g., simvastatin Exemplary Inhibitory Compounds Since inhibition of KRC activity is associated with increased bone formation and mineralization, and/or a decreased immune response, to increase bone formation and mineralization and/or downmodulate or inhibit the immune response, cells (e.g., osteoblasts or T cells) are contacted with an agent that inhibits KRC activity. The cells may be contacted with the agent in vitro and then the cells can be administered to a subject or, alternatively, the agent may be administered to the subject (e.g., directly to an articular site at which T growth and/or differentiation is desired). The methods of the invention using KRC inhibitory compounds can be used in the treatment of disorders in which increased bone formation and mineralization is beneficial or in which the immune response is diminished, blocked, inhibited, downregulated or the like.

Inhibitory compounds of the invention can be, for example, intracellular binding molecules that act to specifically inhibit the expression or activity of KRC. As used herein, the term "intracellular binding molecule" is intended to include molecules that act intracellularly to inhibit the expression or activity of a protein by binding to the protein or to a nucleic acid (e.g., an mRNA molecule) that encodes the protein. Examples of intracellular binding molecules, described in further detail below, include antisense nucleic acids, siRNA molecules, intracellular antibodies, peptidic compounds that inhibit the interaction of KRC with a target molecule (e.g., calcineurin, Runx2, WWP1, and/or SMAD3) and chemical agents that specifically inhibit KRC activity.

i. Antisense or siRNA Nucleic Acid Molecules

In one embodiment, an inhibitory compound of the invention is an antisense nucleic acid molecule that is complementary to a gene encoding KRC, a gene encoding Runx2, a gene encoding SMAD3, a gene encoding WWP1, a gene encoding RSK2, or a molecule in a signal transduction pathway involving KRC, or to a portion of said genes, or a recombinant expression vector encoding said antisense nucleic acid molecules. For simplicity, the below-mentioned exemplary antisense and siRNA molecules will refer to KRC antisense and siRNA molecules. However, it is understood that exemplary antisense and siRNA molecules of the above-mentioned molecules, e.g., Runx2, SMAD3, RSK2, WWP1, a molecule in a signal transduction pathway involving KRC, or a portion of said genes, are also included in the invention. The use of antisense nucleic acids to downregulate the expression of a particular protein in a cell is well known in the art (see e.g., Weintraub, H. et al., Antisense RNA as a molecular tool for genetic analysis, *Reviews—Trends in Genetics*, Vol. 1(1) 1986; Askari, F. K. and McDonnell, W. M. (1996) *N. Eng. J. Med.* 334:316-318; Bennett, M. R. and Schwartz, S. M. (1995) *Circulation* 92:1981-1993; Mercola, D. and Cohen, J. S. (1995) *Cancer Gene Ther.* 2:47-59; Rossi, J. J. (1995) *Br. Med. Bull.* 51:217-225; Wagner, R. W. (1994) *Nature* 372: 333-335). An antisense nucleic acid molecule comprises a nucleotide sequence that is complementary to the coding strand of another nucleic acid molecule (e.g., an mRNA sequence) and accordingly is capable of hydrogen bonding to the coding strand of the other nucleic acid molecule. Antisense sequences complementary to a sequence of an mRNA can be complementary to a sequence found in the coding region of the mRNA, the 5' or 3' untranslated region of the mRNA or a region bridging the coding region and an untranslated region (e.g., at the junction of the 5' untranslated region and the coding region). Furthermore, an antisense nucleic acid can be complementary in sequence to a regulatory region of the gene encoding the mRNA, for instance a transcription initiation sequence or regulatory element. Preferably, an antisense nucleic acid is designed so as to be complementary to a region preceding or spanning the initiation codon on the coding strand or in the 3' untranslated region of an mRNA.

Given the coding strand sequences encoding KRC disclosed herein, antisense nucleic acids of the invention can be designed according to the rules of Watson and Crick base pairing. The antisense nucleic acid molecule can be complementary to the entire coding region of KRC mRNA, but more preferably is an oligonucleotide which is antisense to only a portion of the coding or noncoding region of KRC mRNA. For example, the antisense oligonucleotide can be complementary to the region surrounding the translation start site of KRC mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. To inhibit expression in cells, one or more antisense oligonucleotides can be used. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a KRC protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids. Res. 15:6625-6641). The antisense nucleic acid molecule can also comprise a 2'-o-methylribonucleotide (Inoue et al. (1987) Nucleic Acids Res. 15:6131-6148) or a chimeric RNA-DNA analogue (Inoue et al. (1987) FEBS Lett. 215:327-330). In another embodiment, an antisense nucleic acid of the invention is a compound that mediates RNAi. RNA interfering agents include, but are not limited to, nucleic acid molecules including RNA molecules which are homologous to the target gene or genomic sequence, e.g., KRC, c-Jun, c-Fos, GATA3, SMAD, and/or Runx2, or a fragment thereof, "short interfering RNA" (siRNA), "short hairpin" or "small hairpin RNA" (shRNA), and small molecules which interfere with or inhibit expression of a target gene by RNA interference (RNAi). RNA interference is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. Cell 101, 25-33 (2000). Tuschl, T. et al. Genes Dev. 13, 3191-3197 (1999)). The process occurs when an endogenous ribonuclease cleaves the longer dsRNA into shorter, 21- or 22-nucleotide-long RNAs, termed small interfering RNAs or siRNAs. The smaller RNA segments then mediate the degradation of the target mRNA. Kits for synthesis of RNAi are commercially available from, e.g. New England Biolabs and Ambion. In one embodiment one or more of the chemistries described above for use in antisense RNA can be employed.

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach, 1988, Nature 334:585-591) can be used to catalytically cleave KRC mRNA transcripts to thereby inhibit translation of KRC mRNA. A ribozyme having specificity for a KRC-encoding nucleic acid can be designed based upon the nucleotide sequence of SEQ ID NO:1 a nucleic acid molecule encoding another KRC family polypeptide. For example, a derivative of a Tetrahymena L-19 IVS RNA can be constructed in which the nucleotide sequence of the active site is complementary to the nucleotide sequence to be cleaved in a KRC-encoding mRNA. See, e.g., Cech et al. U.S. Pat. No. 4,987,071; and Cech et al. U.S. Pat. No. 5,116,742. Alternatively, KRC mRNA can be used to select a catalytic RNA having a specific ribonuclease activity from a pool of RNA molecules. See, e.g., Bartel, D. and Szostak, J. W., 1993, *Science* 261:1411-1418.

Alternatively, gene expression can be inhibited by targeting nucleotide sequences complementary to the regulatory region of KRC (e.g., the KRC promoter and/or enhancers) to form triple helical structures that prevent transcription of the KRC gene in target cells. See generally, Helene, C., 1991, *Anticancer Drug Des.* 6(6):569-84; Helene, C. et al., 1992, *Ann. N.Y. Acad. Sci.* 660:27-36; and Maher, L. J., 1992, *Bioassays* 14(12):807-15.

In yet another embodiment, the KRC nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al., 1996, *Bioorganic & Medicinal Chemistry* 4 (1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al., 1996, supra; Perry-O'Keefe et al., 1996, *Proc. Natl. Acad. Sci. USA* 93: 14670-675.

PNAs of KRC nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of KRC nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B., 1996, supra)); or as probes or primers for DNA sequencing or hybridization (Hyrup B. et al., 1996, supra; Perry-O'Keefe supra).

In another embodiment, PNAs of KRC can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of KRC nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B., 1996, supra). The synthesis of PNA-DNA chimeras can be performed as described in Hyrup B., 1996, supra and Finn P. J. et al., 1996, *Nucleic Acids Res.* 24 (17): 3357-63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA Gag, M. et al., 1989, *Nucleic Acid Res.* 17: 5973-88). PNA monomers are then coupled in a stepwise manner to produce a chimeric molecule with a 5' PNA segment and a 3' DNA segment (Finn P. J. et al., 1996, supra). Alternatively, chimeric molecules can be synthesized with a 5' DNA segment and a 3' PNA segment (Peterser, K. H. et al., 1975, *Bioorganic Med. Chem. Lett.* 5: 1119-11124).

In other embodiments, the oligonucleotide may include other appended groups such as peptides (e.g., for targeting host cell receptors in vivo), or agents facilitating transport across the cell membrane (see, e.g., Letsinger et al., 1989, *Proc. Natl. Acad. Sci. US.* 86:6553-6556; Lemaitre et al., 1987, *Proc. Natl. Acad. Sci. USA* 84:648-652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al., 1988, *Bio-Techniques* 6:958-976) or intercalating agents. (See, e.g., Zon, 1988, *Pharm. Res.* 5:539-549). To this end, the oligonucleotide may be conjugated to another molecule, (e.g., a peptide, hybridization triggered cross-linking agent, transport agent, or hybridization-triggered cleavage agent).

Antisense polynucleotides may be produced from a heterologous expression cassette in a transfectant cell or transgenic cell. Alternatively, the antisense polynucleotides may comprise soluble oligonucleotides that are administered to the external milieu, either in the culture medium in vitro or in the circulatory system or in interstitial fluid in vivo. Soluble antisense polynucleotides present in the external milieu have been shown to gain access to the cytoplasm and inhibit translation of specific mRNA species.

In another embodiment, a compound that promotes RNAi can be used to inhibit expression of KRC or a molecule in a signal transduction pathway involving KRC. RNA interference (RNAi is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. Cell 101, 25-33 (2000). Tuschl, T. et al. Genes Dev. 13, 3191-3197 (1999); Cottrell T R, and Doering T L. 2003. Trends Microbiol. 11:37-43; Bushman F. 2003. Mol. Therapy. 7:9-10; McManus M T and Sharp P A. 2002. Nat Rev Genet. 3:737-47). The process occurs when an endogenous ribonuclease cleaves the longer dsRNA into shorter, e.g., 21- or 22-nucleotide-long RNAs, termed small interfering RNAs or siRNAs. The smaller RNA segments then mediate the degradation of the target mRNA. Kits for synthesis of RNAi are commercially available from, e.g. New England Biolabs or Ambion. In one embodiment one or more of the chemistries described above for use in antisense RNA can be employed in molecules that mediate RNAi. Non-limiting exemplary siRNA molecules of the invention are listed below.

Exemplary siRNA molecules specific for human KRC (SEQ ID NO: 1) are shown below:

```
Beginning at position 1576:
                                      (SEQ ID NO: 4)
Sense strand siRNA: GACCAAGAGUAAUCUCUACtt (SEQ ID NO: 5)
Antisense strand siRNA: GUAGAGAUUACUCUUGGUCtt Beginning at position 3310:
                                      (SEQ ID NO: 6)
Sense strand siRNA: AUCUGAUUCUCUCGAGCAGtt (SEQ ID NO: 7)
Antisense strand siRNA: CUGCUCGAGAGAAUCAGAUtt Beginning at position 5725:
                                      (SEQ ID NO: 9)
Sense strand siRNA: GCCAAAUCACAUCCAGCAUtt (SEQ ID NO: 10)
Antisense strand siRNA: AUGCUGGAUGUGAUUUGGCtt
```

Exemplary siRNA molecules specific for human CBFβ (gi:47132616) are shown below:

```
Beginning at position 288 of gi: 47132616:
                                        (SEQ ID NO: 11)
Sense strand siRNA: GCAAGUUCGAGAACGAGGAtt
                                        (SEQ ID NO: 12)
Antisense strand siRNA: UCCUCGUUCUCGAACUUGCtt Beginning at position 692 of gi: 47132616:
                                        (SEQ ID NO: 13)
Sense strand siRNA: GAGGCUCGGAGAAGGACACtt (SEQ ID NO: 14)
Antisense strand siRNA: GUGUCCUUCUCCGAGCCUCtt Beginning at position 1155 of gi: 47132616:
                                        (SEQ ID NO: 15)
Sense strand siRNA: AAACAAGUCAAGAAAUUAAtt (SEQ ID NO: 16)
Antisense strand siRNA: UUAAUUUCUUGACUUGUUUtt
```

Exemplary siRNA molecules specific for human SMAD3 (gi:42476202) are shown below:

```
Beginning at position 556 of gi: 42476202:
                                        (SEQ ID NO: 17)
Sense strand siRNA: UAUGAAGAAGGACGAGGUCtt (SEQ ID NO: 18)
Antisense strand siRNA: GACCUCGUCCUUCUUCAUAtt Beginning at position 1231 of gi: 42476202:
                                        (SEQ ID NO: 19)
Sense strand siRNA: CCUGAAGAUCUUCAACAACtt (SEQ ID NO: 20)
Antisense strand siRNA: GUUGUUGAAGAUCUUCAGGtt Beginning at position 1557 of gi: 42476202:
                                        (SEQ ID NO: 21)
Sense strand siRNA: UUGGAACUCUACUCAACCCtt (SEQ ID NO: 22)
Antisense strand siRNA: GGGUUGAGUAGAGUUCCAAtt
```

Exemplary siRNA molecules specific for human WWP1 (gi:33946331) are shown below:

```
Beginning at position 831 of gi: 33946331:
                                        (SEQ ID NO: 23)
Sense strand siRNA: GGCACGAAUGGAAUAGAUAtt (SEQ ID NO: 24)
Antisense strand siRNA: UAUCUAUUCCAUUCGUGCCtt Beginning at position 2186 of gi: 33946331:
                                        (SEQ ID NO: 25)
Sense strand siRNA: GAACAACUAUUGUCUGCAGtt (SEQ ID NO: 26)
Antisense strand siRNA: CUGCAGACAAUAGUUGUUCtt Beginning at position 3256 of gi: 33946331:
                                        (SEQ ID NO: 27)
Sense strand siRNA: AGAUCAUCCUUAAAUUUUGtt (SEQ ID NO: 28)
Antisense strand siRNA: CAAAAUUUAAGGAUGAUCUtt
```

Exemplary siRNA molecules specific for human RSK2 (gi:56243494) are shown below:

```
Beginning at position 611 of gi: 56243494:
                                        (SEQ ID NO: 29)
Sense strand siRNA: GGUCACAUCAAGUUAACAGtt (SEQ ID NO: 30)
Antisense strand siRNA: CUGUUAACUUGAUGUGACCtt Beginning at position 3077 of gi: 56243494:
                                        (SEQ ID NO: 31)
Sense strand siRNA: GGAAGUAGUCCUUGCACUUtt (SEQ ID NO: 32)
Antisense strand siRNA: AAGUGCAAGGACUACUUCCtt Beginning at position 5364 of gi: 56243494:
                                        (SEQ ID NO: 33)
Sense strand siRNA: UGCAACAGACCCCCAACUUtt (SEQ ID NO: 34)
Antisense strand siRNA: AAGUUGGGGUCUGUUGCAtt
```

Exemplary siRNA molecules specific for human RUNX2 (gi:10863884) are shown below:

```
Beginning at position 486 of gi: 10863884:
                                        (SEQ ID NO: 35)
Sense strand siRNA: ACCAAGUAGCAAGGUUCAAtt (SEQ ID NO: 36)
Antisense strand siRNA: UUGAACCUUGCUACUUGGUtt Beginning at position 797 of gi: 10863884:
                                        (SEQ ID NO: 37)
Sense strand siRNA: GGACAGAGUCAGAUUACAGtt (SEQ ID NO: 38)
Antisense strand siRNA: CUGUAAUCUGACUCUGUCCtt Beginning at position 1423 of gi: 10863884:
                                        (SEQ ID NO: 39)
Sense strand siRNA: CCAGAAUGAUGGUGUUGACtt (SEQ ID NO: 40)
Antisense strand siRNA: GUCAACACCAUCAUUCUGGtt
``` ii. Intracellular Antibodies

Another type of inhibitory compound that can be used to inhibit the expression and/or activity of KRC protein in a cell is an intracellular antibody specific for KRC interacting polypeptides discussed herein. As stated above, for simplicity, the below-mentioned exemplary intracellular antibodies will refer to KRC intracellular antibodies. However, it is understood that exemplary intracellular antibodies of the above-mentioned molecules, e.g., Runx2, SMAD3, WWP 1, RSK2, a molecule in a signal transduction pathway involving KRC, or a portion of said genes, are also included in the invention. The use of intracellular antibodies to inhibit protein function in a cell is known in the art (see e.g., Carlson, J. R. (1988) *Mol. Cell. Biol.* 8:2638-2646; Biocca, S. et al. (1990) *EMBO J.* 9:101-108; Werge, T. M. et al. (1990) *FEBS Letters* 274:193-198; Carlson, J. R. (1993) *Proc. Natl. Acad. Sci. USA* 90:7427-7428; Marasco, W. A. et al. (1993) *Proc. Natl. Acad. Sci. USA* 90:7889-7893; Biocca, S. et al. (1994) *Bio/Technology* 12:396-399; Chen, S-Y. et al. (1994) *Human Gene Therapy* 5:595-601; Duan, L et al. (1994) *Proc. Natl. Acad. Sci. USA* 91:5075-5079; Chen, S-Y. et al. (1994) *Proc. Natl. Acad. Sci. USA* 91:5932-5936; Beerli, R. R. et al. (1994) *J. Biol. Chem.* 269:23931-23936; Beerli, R. R. et al. (1994) *Biochem. Biophys. Res. Commun.* 204:666-672; Mhashilkar, A. M. et al. (1995) *EMBO J.* 14:1542-1551; Richardson, J. H.

et al. (1995) *Proc. Natl. Acad. Sci. USA* 92:3137-3141; PCT Publication No. WO 94/02610 by Marasco et al.; and PCT Publication No. WO 95/03832 by Duan et al.).

To inhibit protein activity using an intracellular antibody, a recombinant expression vector is prepared which encodes the antibody chains in a form such that, upon introduction of the vector into a cell, the antibody chains are expressed as a functional antibody in an intracellular compartment of the cell. For inhibition of transcription factor activity according to the inhibitory methods of the invention, preferably an intracellular antibody that specifically binds the transcription factor is expressed within the nucleus of the cell. Nuclear expression of an intracellular antibody can be accomplished by removing from the antibody light and heavy chain genes those nucleotide sequences that encode the N-terminal hydrophobic leader sequences and adding nucleotide sequences encoding a nuclear localization signal at either the N- or C-terminus of the light and heavy chain genes (see e.g., Biocca, S. et al. (1990) *EMBO J.* 9:101-108; Mhashilkar, A. M. et al. (1995) *EMBO J.* 14:1542-1551). A preferred nuclear localization signal to be used for nuclear targeting of the intracellular antibody chains is the nuclear localization signal of SV40 Large T antigen (see Biocca, S. et al. (1990) *EMBO J.* 9:101-108; Mhashilkar, A. M. et al. (1995) *EMBO J.* 14:1542-1551).

To prepare an intracellular antibody expression vector, antibody light and heavy chain cDNAs encoding antibody chains specific for the target protein of interest, e.g., KRC protein, is isolated, typically from a hybridoma that secretes a monoclonal antibody specific for KRC protein. Preparation of antisera against KRC protein has been described in the art (see e.g., Rao et al, U.S. Pat. No. 5,656,452). Anti-KRC protein antibodies can be prepared by immunizing a suitable subject, (e.g., rabbit, goat, mouse or other mammal) with a KRC protein immunogen. An appropriate immunogenic preparation can contain, for example, recombinantly expressed KRC protein or a chemically synthesized KRC peptide. The preparation can further include an adjuvant, such as Freund's complete or incomplete adjuvant, or similar immunostimulatory compound. Antibody-producing cells can be obtained from the subject and used to prepare monoclonal antibodies by standard techniques, such as the hybridoma technique originally described by Kohler and Milstein (1975, *Nature* 256:495-497) (see also, Brown et al. (1981) *J Immunol* 127:539-46; Brown et al. (1980) *J Biol Chem* 255: 4980-83; Yeh et al. (1976) *PNAS* 76:2927-31; and Yeh et al. (1982) *Int. J. Cancer* 29:269-75). The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.,* 54:387-402; M. L. Gefter et al. (1977) *Somatic Cell Genet.,* 3:231-36). Briefly, an immortal cell line (typically a myeloma) is fused to lymphocytes (typically splenocytes) from a mammal immunized with a KRC protein immunogen as described above, and the culture supernatants of the resulting hybridoma cells are screened to identify a hybridoma producing a monoclonal antibody that binds specifically to the KRC protein. Any of the many well known protocols used for fusing lymphocytes and immortalized cell lines can be applied for the purpose of generating an anti-KRC protein monoclonal antibody (see, e.g., G. Galfre et al. (1977) *Nature,* 266:550-52; Gefter et al. *Somatic Cell Genet.,* cited supra; Lerner, Yale J. Biol. Med., cited supra; Kenneth, *Monoclonal Antibodies,* cited supra). Moreover, the ordinary skilled artisan will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody that specifically binds the maf protein are identified by screening the hybridoma culture supernatants for such antibodies, e.g., using a standard ELISA assay.

Alternative to preparing monoclonal antibody-secreting hybridomas, a monoclonal antibody that binds to a KRC can be identified and isolated by screening a recombinant combinatorial immunoglobulin library (e.g. an antibody phage display library) with the protein, or a peptide thereof, to thereby isolate immunoglobulin library members that bind specifically to the protein. Kits for generating and screening phage display libraries are commercially available (e.g., the Pharmacia *Recombinant Phage Antibody System,* Catalog No. 27-9400-01; and the Stratagene *SurfZAP™ Phage Display Kit,* Catalog No. 240612). Additionally, examples of methods and compounds particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J.* 12:725-734; Hawkins et al. (1992) *J Mol Biol* 226:889-896; Clarkson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; Barbas et al. (1991) *PNAS* 88:7978-7982; and McCafferty et al. *Nature* (1990) 348:552-554.

Once a monoclonal antibody of interest specific for KRC has been identified (e.g., either a hybridoma-derived monoclonal antibody or a recombinant antibody from a combinatorial library, including monoclonal antibodies to KRC that are already known in the art), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, cDNA encoding the light and heavy chains can be recovered from the display package (e.g., phage) isolated during the library screening process. Nucleotide sequences of antibody light and heavy chain genes from which PCR primers or cDNA library probes can be prepared are known in the art. For example, many such sequences are disclosed in Kabat, E. A., et al. (1991) *Sequences of Proteins of Immunological Interest, Fifth Edition*, U.S. Department of Health and Human Services, NIH Publication No. 91-3242 and in the "Vbase" human germline sequence database.

Once obtained, the antibody light and heavy chain sequences are cloned into a recombinant expression vector using standard methods. As discussed above, the sequences encoding the hydrophobic leaders of the light and heavy chains are removed and sequences encoding a nuclear localization signal (e.g., from SV40 Large T antigen) are linked in-frame to sequences encoding either the amino- or carboxy terminus of both the light and heavy chains. The expression vector can encode an intracellular antibody in one of several different forms. For example, in one embodiment, the vector encodes full-length antibody light and heavy chains such that a full-length antibody is expressed intracellularly. In another embodiment, the vector encodes a full-length light chain but only the VH/CH1 region of the heavy chain such that a Fab fragment is expressed intracellularly. In the most preferred embodiment, the vector encodes a single chain antibody (scFv) wherein the variable regions of the light and heavy chains are linked by a flexible peptide linker (e.g., (Gly$_4$Ser)$_3$) (SEQ ID NO:41) and expressed as a single chain molecule. To inhibit transcription factor activity in a cell, the expression vector encoding the KRC-specific intracellular antibody is introduced into the cell by standard transfection methods as described hereinbefore.

iii. KRC-Derived Peptidic Compounds

In another embodiment, an inhibitory compound of the invention is a peptidic compound derived from the KRC amino acid sequence. As stated above, for simplicity, the below-mentioned exemplary peptidic compounds will refer to peptidic compound derived from the KRC amino acid sequence. However, it is understood that exemplary peptidic compounds of the above-mentioned molecules, e.g., Runx2, SMAD3, WWP1, RSK2, a molecule in a signal transduction pathway involving KRC, or a portion of said genes, are also included in the invention. In particular, the inhibitory compound comprises a portion of KRC (or a mimetic thereof) that mediates interaction of KRC with a target molecule such that contact of KRC with this peptidic compound competitively inhibits the interaction of KRC with the target molecule. In an exemplary embodiment, the peptide compound is designed based on the region of KRC that mediates interaction of KRC with, for example, TRAF, Jun, GATA3, SMAD2, SMAD3, WWP1, CBFβ, RSK2, and/or Runx2. As described herein, amino acid residues 204-1055 of the KRC protein mediate the interaction of the KRC proteins with TRAF and peptides spanning the region inhibit the ability of TRAF to bind to and phosphorylate KRC proteins, without affecting the phosphatase activity of TRAF against other substrates. Moreover, when expressed intracellularly, peptides spanning this region inhibit KRC dephosphorylation, nuclear translocation and KRC-mediated gene expression in response to stimulation, thereby inhibiting KRC-dependent functions.

In a preferred embodiment, a KRC inhibitory compound is a peptidic compound, which is prepared based on a TRAF-interacting region of KRC. A peptide can be derived from the TRAF-interacting region of KRC having an amino acid sequence that comprises the amino acid residues 204-1055 of KRC. In another preferred embodiment, a KRC inhibitory compound is a peptidic compound, which is prepared based on a c-Jun-interacting region of KRC. A peptide can be derived from the c-Jun-interacting region of KRC having an amino acid sequence that comprises the amino acid residues 204-1055 of KRC. Alternatively, longer or shorter regions of human KRC can be used, such as a peptide.

The peptidic compounds of the invention can be made intracellularly in osteoblasts and/or immune cells by introducing into the cells an expression vector encoding the peptide. Such expression vectors can be made by standard techniques, using, for example, oligonucleotides that encode the amino acid sequences of SEQ ID NO: 2. The peptide can be expressed in intracellularly as a fusion with another protein or peptide (e.g., a GST fusion). Alternative to recombinant synthesis of the peptides in the cells, the peptides can be made by chemical synthesis using standard peptide synthesis techniques. Synthesized peptides can then be introduced into cells by a variety of means known in the art for introducing peptides into cells (e.g., liposome and the like).

Other inhibitory agents that can be used to specifically inhibit the activity of an KRC protein are chemical compounds that directly inhibit KRC activity or inhibit the interaction between KRC and target molecules. Such compounds can be identified using screening assays that select for such compounds, as described in detail above.

B. Upregulation of KRC Biological Activities

Stimulation of KRC activity as a means of downmodulating bone formation and mineralization is also useful in therapy. For example, decreasing or inhibiting bone formation and mineralization by enhancing KRC is beneficial in diseases, disorders, conditions or injuries in which there is premature fusing of two or more bone, or bone density is too high, such as for example, craniosynostosis (synostosis), osteopetrosis (including malignant infantile form, intermediate form, and adult form), primary extra-skeletal bone formation, e.g., multiple miliary osteoma cutis of the face, and osteitis condensans.

Alternatively, bone formation and mineralization decreased in a patient by removing cells from the patient, contacting cells in vitro with an agent (e.g., a small molecule) that enhances KRC activity, and reintroducing the in vitro-stimulated cells into the patient. In another embodiment, a method of enhancing immune responses or decreasing bone formation and mineralization involves isolating cells from a patient, transfecting them with a nucleic acid molecule encoding a KRC molecule and reintroducing the transfected cells into the patient.

In an additional embodiment, in performing any of the methods described herein, it is within the scope of the invention to inhibit bone formation and mineralization by administering one or more additional agents.

In another embodiment, a method of upregulating immune responses or decreasing bone formation and mineralization involves transfecting them with a nucleic acid molecule encoding a KRC molecule with a mutation or a peptide that enhances, for example, KRC-TRAF interaction (e.g., a TRAF-C domain), such that the cells express the KRC molecule (e.g., in the cell membrane) or the peptide (e.g. in the cytoplasm), and reintroducing the transfected cells into the patient. The ability of the transfected cells to be activated can thus be increased.

In an additional embodiment, in performing any of the methods described herein, it is within the scope of the invention to downregulate bone formation and mineralization by administering one or more additional agents. For example, surgical repair, surgical implantation of biodegradable devices, rosiglitazone, RANKL, tretinoin, enoxaparin can be used in conjunction with an agent that enhances KRC activity.

Exemplary Stimulatory Compounds

Since upregulation of KRC activity is associated with decreased bone formation and mineralization, a compound that specifically stimulates KRC activity and/or expression can be used to inhibit bone formation and mineralization. In the stimulatory methods of the invention, a subject is treated with a stimulatory compound that stimulates expression and/or activity of a KRC molecule. The methods of the invention using KRC stimulatory compounds can be used in the treatment of disorders in which the enhancement of bone formation and mineralization is desirable.

Examples of stimulatory compounds include active KRC protein or a molecule in a signal transduction pathway involving KRC, expression vectors encoding KRC and chemical agents that specifically stimulate KRC activity.

As stated above, for simplicity, the below-mentioned exemplary stimulatory compounds will refer to KRC stimulatory compounds. However, it is understood that exemplary stimulatory compounds of the above-mentioned molecules, e.g., Runx2, SMAD3, RSK2, WWP1, a molecule in a signal transduction pathway involving KRC, or a portion of said genes, are also included in the invention.

A preferred stimulatory compound is a nucleic acid molecule encoding KRC, wherein the nucleic acid molecule is introduced into the subject (e.g., T cells or osteoblasts of the subject) in a form suitable for expression of the KRC protein in the cells of the subject. For example, a KRC cDNA (full length or partial KRC cDNA sequence) is cloned into a recombinant expression vector and the vector is transfected into the immune cell using standard molecular biology techniques. The KRC cDNA can be obtained, for example, by amplification using the polymerase chain reaction (PCR) or by screening an appropriate cDNA library. The nucleotide sequences of KRC cDNA is known in the art and can be used for the design of PCR primers that allow for amplification of a cDNA by standard PCR methods or for the design of a hybridization probe that can be used to screen a cDNA library using standard hybridization methods.

Following isolation or amplification of KRC cDNA, the DNA fragment is introduced into a suitable expression vector, as described above. Nucleic acid molecules encoding KRC in the form suitable for expression of the KRC in a host cell, can be prepared as described above using nucleotide sequences known in the art. The nucleotide sequences can be used for the design of PCR primers that allow for amplification of a cDNA by standard PCR methods or for the design of a hybridization probe that can be used to screen a cDNA library using standard hybridization methods.

Another form of a stimulatory compound for stimulating expression of KRC in a cell is a chemical compound that specifically stimulates the expression or activity of endogenous KRC in the cell. Such compounds can be identified using screening assays that select for compounds that stimulate the expression or activity of KRC as described herein.

The method of the invention for modulating KRC activity in a subject can be practiced either in vitro or in vivo (the latter is discussed further in the following subsection). For practicing the method in vitro, cells (e.g., T cells or osteoblasts) can be obtained from a subject by standard methods and incubated (i.e., cultured) in vitro with a stimulatory or inhibitory compound of the invention to stimulate or inhibit, respectively, the activity of KRC. Methods for isolating immune cells and osteoblasts are known in the art.

Cells treated in vitro with either a stimulatory or inhibitory compound can be administered to a subject to influence the growth and/or differentiation of cells in the subject.

In other embodiments, a stimulatory or inhibitory compound is administered to a subject in vivo, such as directly to an articulation site of a subject. For stimulatory or inhibitory agents that comprise nucleic acids (e.g., recombinant expression vectors encoding KRC, antisense RNA, intracellular antibodies or KRC-derived peptides), the compounds can be introduced into cells of a subject using methods known in the art for introducing nucleic acid (e.g., DNA) into cells in vivo. Examples of such methods include:

Direct Injection:

Naked DNA can be introduced into cells in vivo by directly injecting the DNA into the cells (see e.g., Acsadi et al. (1991) *Nature* 332:815-818; Wolff et al. (1990) *Science* 247:1465-1468). For example, a delivery apparatus (e.g., a "gene gun") for injecting DNA into cells in vivo can be used. Such an apparatus is commercially available (e.g., from BioRad).

Receptor-Mediated DNA Uptake:

Naked DNA can also be introduced into cells in vivo by complexing the DNA to a cation, such as polylysine, which is coupled to a ligand for a cell-surface receptor (see for example Wu, G. and Wu, C. H. (1988) *J. Biol. Chem.* 263: 14621; Wilson et al. (1992) *J. Biol. Chem.* 267:963-967; and U.S. Pat. No. 5,166,320). Binding of the DNA-ligand complex to the receptor facilitates uptake of the DNA by receptor-mediated endocytosis. A DNA-ligand complex linked to adenovirus capsids which naturally disrupt endosomes, thereby releasing material into the cytoplasm can be used to avoid degradation of the complex by intracellular lysosomes (see for example Curiel et al. (1991) *Proc. Natl. Acad. Sci. USA* 88:8850; Cristiano et al. (1993) *Proc. Natl. Acad. Sci. USA* 90:2122-2126).

Retroviruses:

Defective retroviruses are well characterized for use in gene transfer for gene therapy purposes (for a review see Miller, A. D. (1990) *Blood* 76:271). A recombinant retrovirus can be constructed having a nucleotide sequences of interest incorporated into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include ψCrip, ψCre, ψ2 and ψAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol.* 150: 4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

Adenzoviruses:

The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431-434; and Rosenfeld et al. (1992) *Cell* 68:143-155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA* 89:6482-6486), hepatocytes (Herz and Gerard (1993) *Proc. Natl. Acad. Sci. USA* 90:2812-2816) and muscle cells (Quanitin et al. (1992) *Proc. Natl. Acad. Sci. USA* 89:2581-2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use are deleted for all or parts of the viral E1 and E3 genes but retain as much as 80% of the adenoviral genetic material.

Adeno-Associated Viruses:

Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158: 97-129). It is also one of the few viruses that may integrate its DNA into non-dividing cells, and exhibits a high frequency of stable integration (see for example Flotte et al. (1992) *Am. J. Respir. Cell. Mol. Biol.* 7:349-356; Samulski et al. (1989) *J. Virol.* 63:3822-3828; and McLaughlin et al. (1989) *J. Virol.* 62:1963-1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251-3260 can be used to introduce DNA into cells. A variety of nucleic acids have been introduced into different cell types using AAV vectors (see for example Hermnonat et al. (1984) *Proc. Natl. Acad. Sci. USA* 81:6466-6470; Tratschin et al. (1985) *Mol. Cell. Biol.* 4:2072-2081; Wondisford et al. (1988) *Mol. Endocrinol.* 2:32-39; Tratschin et al. (1984) *J. Virol.* 51:611-619; and Flotte et al. (1993) *J. Biol. Chem.* 268:3781-3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product, such as an enzymatic assay.

III. Diagnostic Assays

In another aspect, the invention features a method of diagnosing a subject for a disorder associated with aberrant biological activity or KRC (e.g., that would benefit from modulation of, e.g., modulation of bone formation and mineralization, modulation of osteoclastogenesis, modulation of osteoblast versus osteoclast activity, modulation of osteoblast versus osteoclast activity, modulation of osteocalcin gene transcription, modulation of the degradation of Runx 2, e.g., modulation of Runx2 protein levels, modulation of the ubiquitination of Runx2, modulation of the expression of RSK2, degradation of RSK2, e.g., modulation of RSK2 protein levels, ubiquitination of RSK2, modulation of the phosphorylation of RSK2, modulation of the expression of BSP, Coll($\alpha$)1, OCN, Osterix, RANKL, and ATF4, modulation of ATF4 protein levels, and/or modulation of the phosphorylation of ATF4.

In one embodiment, the invention comprises identifying the subject as one that would benefit from modulation of KRC activity, e.g., modulation of bone formation and mineralization, modulation of osteoclastogenesis, modulation of osteoblast versus osteoclast activity, modulation of osteocalcin gene transcription, modulation of the degradation of Runx 2, e.g., modulation of Runx2 protein levels, modulation of the ubiquitination of Runx2, modulation of the expression of RSK2, degradation of RSK2, e.g., modulation of RSK2 protein levels, ubiquitination of RSK2, modulation of the phosphorylation of RSK2, modulation of the expression of BSP, Coll($\alpha$)1, OCN, Osterix, RANKL, and ATF4, modulation of ATF4 protein levels, and/or modulation of the phosphorylation of ATF4.

For example, in one embodiment, expression of KRC or a molecule in a signal transduction pathway involving KRC can be detected in cells of a subject suspected of having a disorder associated with, aberrant biological activity of KRC. The expression of KRC or a molecule in a signal transduction pathway involving KRC in cells of said subject could then be compared to a control and a difference in expression of KRC or a molecule in a signal transduction pathway involving KRC in cells of the subject as compared to the control could be used to diagnose the subject as one that would benefit from modulation of KRC activity.

The "change in expression" or "difference in expression" of KRC or a molecule in a signal transduction pathway involving KRC in cells of the subject can be, for example, a change in the level of expression of KRC or a molecule in a signal transduction pathway involving KRC in cells of the subject as compared to a previous sample taken from the subject or as compared to a control, which can be detected by assaying levels of, e.g., KRC mRNA, for example, by isolating cells from the subject and determining the level of KRC mRNA expression in the cells by standard methods known in the art, including Northern blot analysis, microarray analysis, reverse-transcriptase PCR analysis and in situ hybridizations. For example, a biological specimen can be obtained from the patient and assayed for, e.g., expression or activity of KRC or a molecule in a signal transduction pathway involving KRC. For instance, a PCR assay could be used to measure the level of KRC in a cell of the subject. A level of KRC higher or lower than that seen in a control or higher or lower than that previously observed in the patient indicates that the patient would benefit from modulation of a signal transduction pathway involving KRC. Alternatively, the level of expression of KRC or a molecule in a signal transduction pathway involving KRC in cells of the subject can be detected by assaying levels of, e.g., KRC, for example, by isolating cells from the subject and determining the level of KRC or a molecule in a signal transduction pathway involving KRC protein expression by standard methods known in the art, including Western blot analysis, immunoprecipitations, enzyme linked immunosorbent assays (ELISAs) and immunofluorescence. Antibodies for use in such assays can be made using techniques known in the art and/or as described herein for making intracellular antibodies.

In another embodiment, a change in expression of KRC or a molecule in a signal transduction pathway involving KRC in cells of the subject results from one or more mutations (i.e., alterations from wildtype), e.g., the KRC gene and mRNA leading to one or more mutations (i.e., alterations from wildtype) in the amino acid sequence of the protein. In one embodiment, the mutation(s) leads to a form of the molecule with increased activity (e.g., partial or complete constitutive activity). In another embodiment, the mutation(s) leads to a form of the molecule with decreased activity (e.g., partial or complete inactivity). The mutation(s) may change the level of expression of the molecule for example, increasing or decreasing the level of expression of the molecule in a subject with a disorder. Alternatively, the mutation(s) may change the regulation of the protein, for example, by modulating the interaction of the mutant protein with one or more targets e.g., resulting in a form of KRC that cannot be phosphorylated or cannot interact with a KRC binding partner. Mutations in the nucleotide sequence or amino acid sequences of proteins can be determined using standard techniques for analysis of DNA or protein sequences, for example for DNA or protein sequencing, RFLP analysis, and analysis of single nucleotide or amino acid polymorphisms. For example, in one embodiment, mutations can be detected using highly sensitive PCR approaches using specific primers flanking the nucleic acid sequence of interest. In one embodiment, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1994) *PNAS* 91:360-364). This method can include the steps of collecting a sample of cells from a patient, isolating nucleic acid (e.g., genomic, DNA) from the cells of the sample, contacting the nucleic acid sample with one or more primers which specifically amplify a sequence under conditions such that hybridization and amplification of the sequence (if present) occurs, and detecting the presence or absence of an amplification product, or detecting the size of the amplification product and comparing the length to a control sample.

In one embodiment, the complete nucleotide sequence for KRC or a molecule in a signal transduction pathway involving KRC can be determined. Particular techniques have been developed for determining actual sequences in order to study polymorphism in human genes. See, for example, Proc. Natl. Acad. Sci. U.S.A. 85, 544-548 (1988) and Nature 330, 384-386 (1987); Maxim and Gilbert. 1977. *PNAS* 74:560; Sanger 1977. *PNAS* 74:5463. In addition, any of a variety of automated sequencing procedures can be utilized when performing diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Restriction fragment length polymorphism mappings (RFLPS) are based on changes at a restriction enzyme site. In one embodiment, polymorphisms from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Moreover, the use of sequence specific ribozymes (see, for example, U.S. Pat. No. 5,498,531) can be used to score for the presence of a specific ribozyme cleavage site.

Another technique for detecting specific polymorphisms in particular DNA segment involves hybridizing DNA segments which are being analyzed (target DNA) with a complimentary, labeled oligonucleotide probe. See Nucl. Acids Res. 9, 879-894 (1981). Since DNA duplexes containing even a single base pair mismatch exhibit high thermal instability, the differential melting temperature can be used to distinguish target DNAs that are perfectly complimentary to the probe from target DNAs that only differ by a single nucleotide. This method has been adapted to detect the presence or absence of a specific restriction site, U.S. Pat. No. 4,683,194. The method involves using an end-labeled oligonucleotide probe spanning a restriction site which is hybridized to a target DNA. The hybridized duplex of DNA is then incubated with the restriction enzyme appropriate for that site. Reformed restriction sites will be cleaved by digestion in the pair of duplexes between the probe and target by using the restriction endonuclease. The specific restriction site is present in the target DNA if shortened probe molecules are detected.

Other methods for detecting polymorphisms in nucleic acid sequences include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the polymorphic sequence with potentially polymorphic RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels. See, for example, Cotton et al. (1988) *Proc. Natl. Acad Sci USA* 85:4397; Saleeba et al. (1992) *Methods Enzymol.* 217:286-295. In a preferred embodiment, the control DNA or RNA can be labeled for detection.

In another embodiment, alterations in electrophoretic mobility can be used to identify polymorphisms. For example, single strand conformation polymorphism (SSCP) may be used to detect differences in electrophoretic mobility between mutant and wild type nucleic acids (Orita et al. (1989) *Proc Natl. Acad. Sci. USA:* 86:2766, see also Cotton (1993) *Mutat Res* 285:125-144; and Hayashi (1992) *Genet Anal Tech Appl* 9:73-79). Single-stranded DNA fragments of sample and control nucleic acids can be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment, the movement of nucleic acid molecule comprising polymorphic sequences in polyacrylamide gels containing a gradient of denaturant is assayed using denaturing gradient gel electrophoresis (DGGE) (Myers et al. (1985) *Nature* 313:495). When DGGE is used as the method of analysis, DNA can be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA Rosenbaum and Reissner (1987) *Biophys Chem* 265:12753).

Examples of other techniques for detecting polymorphisms include, but are not limited to, selective oligonucleotide hybridization, selective amplification, or selective primer extension. For example, oligonucleotide primers may be prepared in which the polymorphic region is placed centrally and then hybridized to target DNA under conditions which permit hybridization only if a perfect match is found (Saiki et al. (1986) *Nature* 324:163); Saiki et al. (1989) *Proc. Natl. Acad. Sci. USA* 86:6230). Such allele specific oligonucleotides are hybridized to PCR amplified target DNA or a number of different polymorphisms when the oligonucleotides are attached to the hybridizing membrane and hybridized with labeled target DNA.

Another process for studying differences in DNA structure is the primer extension process which consists of hybridizing a labeled oligonucleotide primer to a template RNA or DNA and then using a DNA polymerase and deoxynucleoside triphosphates to extend the primer to the 5' end of the template. Resolution of the labeled primer extension product is then done by fractionating on the basis of size, e.g., by electrophoresis via a denaturing polyacrylamide gel. This process is often used to compare homologous DNA segments and to detect differences due to nucleotide insertion or deletion. Differences due to nucleotide substitution are not detected since size is the sole criterion used to characterize the primer extension product.

Another process exploits the fact that the incorporation of some nucleotide analogs into DNA causes an incremental shift of mobility when the DNA is subjected to a size fractionation process, such as electrophoresis. Nucleotide analogs can be used to identify changes since they can cause an electrophoretic mobility shift. See, U.S. Pat. No. 4,879,214.

Many other techniques for identifying and detecting polymorphisms are known to those skilled in the art, including those described in "DNA Markers: Protocols, Applications and Overview," G. Caetano-Anolles and P. Gresshoff ed., (Wiley-VCH, New York) 1997, which is incorporated herein by reference as if fully set forth.

In addition, many approaches have also been used to specifically detect SNPs. Such techniques are known in the art and many are described e.g., in DNA Markers: Protocols, Applications, and Overviews. 1997. Caetano-Anolles and Gresshoff, Eds. Wiley-VCH, New York, pp 199-211 and the references contained therein). For example, in one embodiment, a solid phase approach to detecting polymorphisms such as SNPs can be used. For example an oligonucleotide ligation assay (OLA) can be used. This assay is based on the ability of DNA ligase to distinguish single nucleotide differences at positions complementary to the termini of co-terminal probing oligonucleotides (see, e.g., Nickerson et al. 1990. *Proc. Natl. Acad. Sci. USA* 87:8923. A modification of this approach, termed coupled amplification and oligonucleotide ligation (CAL) analysis, has been used for multiplexed genetic typing (see, e.g., Eggerding 1995 *PCR Methods Appl.* 4:337); Eggerding et al. 1995 Hum. Mutat. 5:153).

In another embodiment, genetic bit analysis (GBA) can be used to detect a SNP (see, e.g., Nikiforov et al. 1994. Nucleic Acids Res. 22:4167; Nikiforov et al. 1994. PCR Methods Appl. 3:285; Nikiforov et al. 1995. Anal Biochem. 227:201). In another embodiment, microchip electrophoresis can be used for high-speed SNP detection (see e.g., Schmalzing et al. 2000. *Nucleic Acids Research,* 28). In another embodiment, matrix-assisted laser desorption/ionization time-of-flight mass (MALDI TOF) mass spectrometry can be used to detect SNPs (see, e.g., Stoerker et al. Nature Biotechnology 18:1213).

In another embodiment, a difference in a biological activity of KRC between a subject and a control can be detected. For example, an activity of KRC or a molecule in a signal transduction pathway involving KRC can be detected in cells of a subject suspected of having a disorder associated with aberrant biological activity of KRC. The activity of KRC or a molecule in a signal transduction pathway involving KRC α in cells of the subject could then be compared to a control and a difference in activity of KRC or a molecule in a signal transduction pathway involving KRC in cells of the subject as compared to the control could be used to diagnose the subject as one that would benefit from modulation of an KRC activity. Activities of KRC or molecules in a signal transduction pathway involving KRC can be detected using methods described herein or known in the art.

In preferred embodiments, the diagnostic assay is conducted on a biological sample from the subject, such as a cell sample or a tissue section (for example, a freeze-dried or fresh frozen section of tissue removed from a subject). In another embodiment, the level of expression of KRC or a molecule in a signal transduction pathway involving KRC in cells of the subject can be detected in vivo, using an appropriate imaging method, such as using a radiolabeled antibody.

In one embodiment, the level of expression of KRC or a molecule in a signal transduction pathway involving KRC in cells of the test subject may be elevated (i.e., increased) relative to the control not associated with the disorder or the subject may express a constitutively active (partially or completely) form of the molecule. This elevated expression level of, e.g., KRC or expression of a constitutively active form of KRC, can be used to diagnose a subject for a disorder associated with increased KRC activity.

In another embodiment, the level of expression of KRC or a molecule in a signal transduction pathway involving KRC in cells of the subject may be reduced (i.e., decreased) relative to the control not associated with the disorder or the subject may express an inactive (partially or completely) mutant form of KRC. This reduced expression level of KRC or expression of an inactive mutant form of sKRC can be used to diagnose a subject for a disorder, such as immunodeficiency disorders characterized by insufficient cytokine production.

In one embodiment, the level of expression of gene whose expression is regulated by KRC can be measured (e.g., IL-2, BSP, ColI(α1)), OCN, RANKL, Osterix, RSK2, and/or ATF4.

In another embodiment, an assay diagnosing a subject as one that would benefit from modulation of KRC expression, post-translational modification, and/or activity (or a molecule in a signal transduction pathway involving KRC) is performed prior to treatment of the subject.

The methods described herein may be performed, for example, by utilizing pre-packaged diagnostic kits comprising at least one probe/primer nucleic acid or other reagent (e.g., antibody), which may be conveniently used, e.g., in clinical settings to diagnose patients exhibiting symptoms or family history of a disease or illness involving KRC or a molecule in a signal transduction pathway involving KRC.

IV. Administration of Modulating Agents

Modulating agents of the invention are administered to subjects in a biologically compatible form suitable for pharmaceutical administration in vivo or on a surface to either enhance or suppress immune responses (e.g., T cell mediated immune responses) or increase or decrease bone formation and mineralization. By "biologically compatible form suitable for administration in vivo" is meant a form of the protein to be administered in which any toxic effects are outweighed by the therapeutic effects of the modulating agent. The term subject is intended to include living organisms in which an immune response or bone formation and mineralization can be elicited, e.g., mammals. Examples of subjects include humans, dogs, cats, mice, rats, and transgenic species thereof, including but not limited to the transgenic KRC mouse described herein. Administration of an agent as described herein can be in any pharmacological form including a therapeutically active amount of an agent alone or in combination with a pharmaceutically acceptable carrier.

Administration of a therapeutically active amount of the therapeutic compositions of the present invention is defined as an amount effective, at dosages and for periods of time necessary to achieve the desired result. For example, a therapeutically active amount of a modulating agent may vary according to factors such as the disease state, age, sex, reproductive state, and weight of the individual, and the ability of the agent to elicit a desired response in the individual. Dosage regimen may be adjusted to provide the optimum therapeutic response. For example, several divided doses may be administered daily or the dose may be proportionally reduced as indicated by the exigencies of the therapeutic situation.

The therapeutic or pharmaceutical compositions of the present invention can be administered by any suitable route known in the art including for example intravenous, subcutaneous, intramuscular, transdermal, intrathecal or intracerebral or administration to cells in ex vivo treatment protocols, or delivered on a surface, e.g., a biocompatible surface, for example on the surface of a surgically implanted device, e.g., as, for example, a putty, for the stabilization, replacement, etc., of a bone, joint, tooth, etc. Administration can be either rapid as by injection or over a period of time as by slow infusion or administration of slow release formulation.

The KRC modulator can also be linked or conjugated with agents that provide desirable pharmaceutical or pharmacodynamic properties. For example, KRC can be stably linked to a polymer such as polyethylene glycol to obtain desirable properties of solubility, stability, half-life and other pharmaceutically advantageous properties. (See for example Davis et al., 1978, *Enzyme Eng* 4: 169-73; Burnham, 1994, *Am J Hosp Pharm* 51: 210-218, which are incorporated by reference).

Furthermore, the KRC modulator can be in a composition which aids in delivery into the cytosol of a cell. For example, the agent may be conjugated with a carrier moiety such as a liposome that is capable of delivering the peptide into the cytosol of a cell. Such methods are well known in the art (for example see Amselem et al., 1993, *Chem Phys Lipids* 64: 219-237, which is incorporated by reference). Alternatively, the KRC modulator can be modified to include specific transit peptides or fused to such transit peptides which are capable of delivering the KRC modulator into a cell. In addition, the agent can be delivered directly into a cell by microinjection.

The compositions are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous. KRC can also be incorporated into a solid or semi-solid biologically compatible matrix which can be implanted into tissues requiring treatment.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion by continuous or periodic infusion.

Dose administration can be repeated depending upon the pharmacokinetic parameters of the dosage formulation and the route of administration used. It is also provided that certain formulations containing the KRC modulator are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, olyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic degradation and/or substances which promote absorption such as, for example, surface active agents.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals. The specific dose can be readily calculated by one of ordinary skill in the art, e.g., according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

Toxicity and therapeutic efficacy of such compounds can be determined by standard pharmaceutical procedures in cell cultures or experimental animals, e.g. for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method for the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In one embodiment of this invention, a KRC modulator may be therapeutically administered by implanting into patients vectors or cells capable of producing a biologically-active form of KRC or a precursor of KRC, i.e. a molecule that can be readily converted to a biological-active form of KRC by the body. In one approach cells that secrete KRC may be encapsulated into semipermeable membranes for implantation into a patient. The cells can be cells that normally express KRC or a precursor thereof or the cells can be transformed to express KRC or a biologically active fragment thereof or a precursor thereof. It is preferred that the cell be of human origin and that the KRC polypeptide be human KRC when the patient is human. However, the formulations and methods herein can be used for veterinary as well as human applications and the term "patient" or "subject" as used herein is intended to include human and veterinary patients.

Monitoring the influence of agents (e.g., drugs or compounds) on the expression or activity of a KRC protein can be applied not only in basic drug screening, but also in clinical trials. For example, the effectiveness of an agent determined by a screening assay as described herein to increase KRC gene expression, protein levels, or upregulate KRC activity, can be monitored in clinical trials of subjects exhibiting decreased KRC gene expression, protein levels, or downregulated KRC activity. Alternatively, the effectiveness of an agent determined by a screening assay to decrease KRC gene expression, protein levels, or downregulate KRC activity, can be monitored in clinical trials of subjects exhibiting increased KRC gene expression, protein levels, or upregulated KRC activity. In such clinical trials, the expression or activity of a KRC gene, and preferably, other genes that have been implicated in a disorder can be used as a "read out" or markers of the phenotype of a particular cell.

For example, and not by way of limitation, genes, including KRC, that are modulated in cells by treatment with an agent (e.g., compound, drug or small molecule) which modulates KRC activity (e.g., identified in a screening assay as described herein) can be identified. Thus, to study the effect of agents on a KRC associated disorder, for example, in a clinical trial, cells can be isolated and RNA prepared and analyzed for the levels of expression of KRC and other genes implicated in the KRC associated disorder, respectively. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of KRC or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a KRC protein, mRNA, or genomic DNA in the pre-administration sample; (iii) obtaining one or more post-administration samples from the subject; (iv) detecting the level of expression or activity of the KRC protein, mRNA, or genomic DNA in the post-administration samples; (v) comparing the level of expression or activity of the KRC protein, mRNA, or genomic DNA in the pre-administration sample with the KRC protein, mRNA, or genomic DNA in the post administration sample or samples; and (vi) altering the administration of the agent to the subject accordingly. For example, increased administration of the agent may be desirable to increase the expression or activity of KRC to higher levels than detected, i.e., to increase the effectiveness of the agent. Alternatively, decreased administration of the agent may be desirable to decrease expression or activity of KRC to lower levels than detected, i.e. to decrease the effectiveness of the agent. According to such an embodiment, KRC expression or activity may be used as an indicator of the effectiveness of an agent, even in the absence of an observable phenotypic response.

In a preferred embodiment, the ability of a KRC modulating agent to modulate inflammation or apoptosis in a epithelial cell of a subject that would benefit from modulation of the expression and/or activity of KRC can be measured by detecting an improvement in the condition of the patient after the administration of the agent. In another preferred embodiment, the ability of a KRC modulating agent to modulate bone formation and mineralization in a subject that would benefit from modulation of the expression and/or activity of KRC can be measured by detecting an improvement in the condition of the patient after the administration of the agent. Such improvement can be readily measured by one of ordinary skill in the art using indicators appropriate for the specific condition of the patient. Monitoring the response of the patient by measuring changes in the condition of the patient is preferred in situations Were the collection of biopsy materials would pose an increased risk and/or detriment to the patient.

It is likely that the level of KRC may be altered in a variety of conditions and that quantification of KRC levels would provide clinically useful information. Furthermore, because it has been demonstrated herein that increased levels of KRC expressed by a cell can shift the cell death regulatory mechanism of that cell to decrease viability, it is believed that measurement of the level of KRC in a cell or cells such as in a group of cells, tissue or neoplasia, like will provide useful information regarding apoptotic state of that cell or cells. In addition, it can also be desirable to determine the cellular levels of these KRC-interacting polypeptides.

Furthermore, in the treatment of disease conditions, compositions containing KRC can be administered exogenously and it would likely be desirable to achieve certain target levels of KRC polypeptide in sera, in any desired tissue compartment or in the affected tissue. It would, therefore, be advantageous to be able to monitor the levels of KRC polypeptide in a patient or in a biological sample including a tissue biopsy sample obtained form a patient and, in some cases, also monitoring the levels of KRC and, in some circumstances, also monitoring levels of TRAM, c-Jun or another KRC-interacting polypeptide, such as Runx2, SMAD3, RSK2, ATF4, and/or WWP1, for example. Accordingly, the present invention also provides methods for detecting the presence of KRC in a sample from a patient.

V. Screening Assays to Identify KRC Modulating Agents

Modulators of KRC activity can be known (e.g. dominant negative inhibitors of KRC activity, antisense KRC intracellular antibodies that interfere with KRC activity, peptide inhibitors derived from KRC) or can be identified using the methods described herein. The invention provides methods (also referred to herein as "screening assays") for identifying other modulators, i.e., candidate or test compounds or agents (e.g., peptidomimetics, small molecules or other drugs) which modulate KRC activity and for testing or optimizing the activity of other agents.

For example, in one embodiment, molecules which bind, e.g., to KRC or a molecule in a signaling pathway involving KRC (e.g., TRAF, NF-kB, JNK, GATA3, SMAD2, SMAD3, CBFβ, Runx2, WWP1, RSK2, and/or AP-1) or have a stimulatory or inhibitory effect on the expression and or activity of KRC or a molecule in a signal transduction pathway involving KRC can be identified. For example, c-Jun, NF-kB, TRAF, GATA3, SMAD2, SMAD3, Runx2, WWP1, CBFβ, JNK, TGFβ, ATF4, RSK2, and/or AP-1 function in a signal transduction pathway involving KRC, therefore, any of these molecules can be used in the subject screening assays. Although the specific embodiments described below in this section and in other sections may list one of these molecules as an example, other molecules in a signal transduction pathway involving KRC can also be used in the subject screening assays.

In one embodiment, the ability of a compound to directly modulate the expression, post-translational modification (e.g., phosphorylation), or activity of KRC is measured in an indicator composition using a screening assay of the invention.

The indicator composition can be a cell that expresses the KRC protein or a molecule in a signal transduction pathway involving KRC, for example, a cell that naturally expresses or, more preferably, a cell that has been engineered to express the protein by introducing into the cell an expression vector encoding the protein. Preferably, the cell is a mammalian cell, e.g., a human cell. In one embodiment, the cell is a T cell. In another embodiment, the cell is a B cell. In another embodiment, the cell is a osteoblast. In another embodiment, the cell is a mature osteoblast. Alternatively, the indicator composition can be a cell-free composition that includes the protein (e.g., a cell extract or a composition that includes e.g., either purified natural or recombinant protein).

Compounds identified using the assays described herein can be useful for treating disorders associated with aberrant expression, post-translational modification, or activity of KRC or a molecule in a signaling pathway involving KRC e.g.: disorders that would benefit from modulation of modulation of bone formation and mineralization, modulation of osteoclastogenesis, modulation of osteoblast versus osteoclast activity, modulation of osteocalcin gene transcription, modulation of the degradation of Runx 2, e.g., modulation of Runx2 protein levels, modulation of the ubiquitination of Runx2, modulation of the expression of RSK2, degradation of RSK2, e.g. modulation of RSK2 protein levels, ubiquitination of RSK2, modulation of the phosphorylation of RSK2, modulation of the expression of BSP, ColI(α)1, OCN, Osterix, RANKL, and ATF4, modulation of ATF4 protein levels, and/or modulation of the phosphorylation of ATF4.

Conditions that can benefit from modulation of a signal transduction pathway involving KRC include diseases, disorders, conditions, or injuries in which modulation of bone formation and mineralization would be beneficial.

In another aspect, the invention pertains to a combination of two or more of the assays described herein. For example, a modulating agent can be identified using a cell-based or a cell-free assay, and the ability of the agent to modulate the activity of KRC or a molecule in a signal transduction pathway involving KRC can be confirmed in vivo, e.g., in an animal, such as, for example, an animal model for, e.g., osteoporosis or osteopetrosis.

Moreover, a modulator of KRC or a molecule in a signaling pathway involving KRC identified as described herein (e.g., an antisense nucleic acid molecule, or a specific antibody, or a small molecule) can be used in an animal model to determine the efficacy, toxicity, or side effects of treatment with such a modulator. Alternatively, a modulator identified as described herein can be used in an animal model to determine the mechanism of action of such a modulator.

In another embodiment, it will be understood that similar screening assays can be used to identify compounds that indirectly modulate the activity and/or expression of KRC e.g., by performing screening assays such as those described above using molecules with which KRC interacts, e.g., molecules that act either upstream or downstream of KRC in a signal transduction pathway.

The cell based and cell free assays of the invention are described in more detail below.

A. Cell Based Assays

The indicator compositions of the invention can be cells that express at least one of a KRC protein or non-KRC protein in the KRC signaling pathway (such as, e.g., TRAF, NF-kB, JNK, Jun, TGFβ, GATA3, SMAD2, SMAD3, CBFβ, WWP1, Runx2, RSK2, ATF4, and/or AP-1) for example, a cell that naturally expresses the endogenous molecule or, more preferably, a cell that has been engineered to express an exogenous KRC, TRAF, NF-kB, JNK, Jun, TGFβ, GATA3, SMAD2, SMAD3, CBFβ, WWP1, Runx2, ATF4, RSK2, and/or protein by introducing into the cell an expression vector encoding the protein(s). Alternatively, the indicator composition can be a cell-free composition that includes at least one of a KRC or a non-KRC protein such as TRAF, NF-kB, JNK, Jun, TGFβ, GATA3, SMAD2, SMAD3, WWP1, CBFβ, Runx2, ATF4, RSK2, and/or (e.g., a cell extract from a cell expressing the protein or a composition that includes purified KRC, TRAF, NF-kB, JNK, Jun, TGFβ, GATA3, SMAD2, SMAD3, WWP1, Runx2, ATF4, RSK2, and/or protein, either natural or recombinant protein).

Compounds that modulate expression and/or activity of KRC, or a non-KRC protein that acts upstream or downstream of can be identified using various "read-outs."

For example, an indicator cell can be transfected with an expression vector, incubated in the presence and in the absence of a test compound, and the effect of the compound on the expression of the molecule or on a biological response regulated by can be determined. The biological activities of include activities determined in vivo, or in vitro, according to standard techniques. Activity can be a direct activity, such as an association with a target molecule or binding partner (e.g., a protein such as the Jun, e.g., c-Jun, TRAF, e.g., TRAF2, GATA3, SMAD, e.g., SMAD2, SMAD3, CBFβ, Runx2, RSK2, and/or WWP1. In one embodiment, the interaction of Runx2 and CBFβ is measured. Alternatively, the activity is an indirect activity, such as a cellular signaling activity occurring downstream of the interaction of the protein with a target molecule or a biological effect occurring as a result of the signaling cascade triggered by that interaction. For example, biological activities of KRC include: modulation of TNFα production, modulation of IL-2 production, modulation of a JNK signaling pathway, modulation of an NFkB signaling pathway, modulation of a TGFβ signaling pathway, modulation of AP-1 activity, modulation of Ras and Rac activity, modulation of actin polymerization, modulation of ubiquitination of AP-1, modulation of ubiquitination of TRAF2, modulation of the degradation of c-Jun, modulation of the degradation of c-Fos, modulation of degradation of SMAD3, modulation of degradation of GATA3, modulation of effector T cell function, modulation of T cell anergy, modulation of apoptosis, or modulation of T cell differentiation, modulation of IgA germline transcription, modulation of bone formation and mineralization, modulation of osteoclastogenesis, modulation of osteoblast versus osteoclast activity, modulation of osteocalcin gene transcription, modulation of the degradation of Runx 2, e.g., modulation of Runx2 protein levels, modulation of the ubiquitination of Runx2, modulation of the expression of RSK2, degradation of RSK2, e.g., modulation of RSK2 protein levels, ubiquitination of RSK2, modulation of the phosphorylation of RSK2, modulation of the expression of BSP, ColI(α)1, OCN, Osterix, RANKL, and ATF4, modulation of ATF4 protein levels, and/or modulation of the phosphorylation of ATF4.

To determine whether a test compound modulates KRC protein expression, or the expression of a protein in a signal transduction pathway involving KRC as described herein, in vitro transcriptional assays can be performed. In one example of such an assay, a regulatory sequence (e.g., the full length promoter and enhancer) of KRC can be operably linked to a reporter gene such as chloramphenicol acetyltransferase (CAT), GFP, or luciferase, e.g., OSE2-luciferase, and introduced into host cells. Other techniques are known in the art.

To determine whether a test compound modulates KRC mRNA expression, or the expression of genes modulated by KRC, e.g., BSP, ColI(α)1, OCN, RANKL, Osterix, RSK2, and ATF4, various methodologies can be performed, such as quantitative or real-time PCR.

As used interchangeably herein, the terms "operably linked" and "operatively linked" are intended to mean that the nucleotide sequence is linked to a regulatory sequence in a manner which allows expression of the nucleotide sequence in a host cell (or by a cell extract). Regulatory sequences are art-recognized and can be selected to direct expression of the desired protein in an appropriate host cell. The term regulatory sequence is intended to include promoters, enhancers, polyadenylation signals and other expression control elements. Such regulatory sequences are known to those skilled in the art and are described in Goeddel, *Gene Expression Technology: Methods in Enzymology* 185, Academic Press, San Diego, Calif. (1990). It should be understood that the design of the expression vector may depend on such factors as the choice of the host cell to be transfected and/or the type and/or amount of protein desired to be expressed.

A variety of reporter genes are known in the art and are suitable for use in the screening assays of the invention. Examples, of suitable reporter genes include those which encode chloramphenicol acetyltransferase, beta-galactosidase, alkaline phosphatase, green fluorescent protein, or luciferase. Standard methods for measuring the activity of these gene products are known in the art.

A variety of cell types are suitable for use as an indicator cell in the screening assay. Preferably a cell line is used which expresses low levels of endogenous KRC (or, e.g., TRAF, Fos, Jun, NF-kB, TGFβ, GATA3, SMAD2, SMAD3, CBFβ, WWP1, AP-1, ATF4, RSK2, and/or Runx2) and is then engineered to express recombinant protein. Cells for use in the subject assays include both eukaryotic and prokaryotic cells. For example, in one embodiment, a cell is a bacterial cell. In another embodiment, a cell is a fungal cell, such as a yeast cell. In another embodiment, a cell is a vertebrate cell, e.g., an avian cell or a mammalian cell (e.g., a murine cell, or a human cell).

In one embodiment, the level of expression of the reporter gene in the indicator cell in the presence of the test compound is higher than the level of expression of the reporter gene in the indicator cell in the absence of the test compound and the test compound is identified as a compound that stimulates the expression of KRC (or, e.g., TRAF, Fos, Jun, NF-kB, TGFβ, GATA3, SMAD2, SMAD3, CBFβ, WWP1, AP-1, ATF4, RSK2, and/or Runx2). In another embodiment, the level of expression of the reporter gene in the indicator cell in the presence of the test compound is lower than the level of expression of the reporter gene in the indicator cell in the absence of the test compound and the test compound is identified as a compound that inhibits the expression of KRC (or, e.g., TRAF, Fos, Jun, NF-kB, TGFβ, GATA3, SMAD2, SMAD3, CBFβ, WWP1, AP-1, ATF4, RSK2, and/or Runx2).

In one embodiment, the invention provides methods for identifying compounds that modulate cellular responses in which KRC is involved.

In one embodiment differentiation of cells, e.g., T cells, can be used as an indicator of modulation of KRC or a signal transduction pathway involving KRC. Cell differentiation can be monitored directly (e.g. by microscopic examination of the cells for monitoring cell differentiation), or indirectly, e.g., by monitoring one or more markers of cell differentiation (e.g., an increase in mRNA for a gene product associated with cell differentiation, or the secretion of a gene product associated with cell differentiation, such as the secretion of a protein (e.g., the secretion of cytokines) or the expression of a cell surface marker (such as CD69). Standard methods for detecting mRNA of interest, such as reverse transcription-polymerase chain reaction (RT-PCR) and Northern blotting, are known in the art. Standard methods for detecting protein secretion in culture supernatants, such as enzyme linked immunosorbent assays (ELISA), are also known in the art. Proteins can also be detected using antibodies, e.g., in an immunoprecipitation reaction or for staining and FACS analysis.

In another embodiment, the ability of a compound to modulate effector T cell function can be determined. For example, in one embodiment, the ability of a compound to modulate T cell proliferation, cytokine production, and/or cytotoxicity can be measured using techniques well known in the art.

In one embodiment, the ability of a compound to modulate IL-2 production can be determined. Production of IL-2 can be monitored, for example, using Northern or Western blotting. IL-2 can also be detected using an ELISA assay or in a bioassay, e.g., employing cells which are responsive to IL-2 (e.g., cells which proliferate in response to the cytokine or which survive in the presence of the cytokine) using standard techniques.

In another embodiment, the ability of a compound to modulate apoptosis can be determined. Apoptosis can be measured in the presence or the absence of Fas-mediated signals. In one embodiment, cytochrome C release from mitochondria during cell apoptosis can be detected, e.g., plasma cell apoptosis (as described in, for example, Bossy-Wetzel E. et al. (2000) *Methods in Enzymol.* 322:235-42). Other exemplary assays include: cytofluorometric quantitation of nuclear apoptosis induced in a cell-free system (as described in, for example, Lorenzo H. K. et al. (2000) *Methods in Enzymol.* 322:198-201); apoptotic nuclease assays (as described in, for example, Hughes F. M. (2000) *Methods in Enzymol.* 322:47-62); analysis of apoptotic cells, e.g., apoptotic plasma cells, by flow and laser scanning cytometry (as described in, for example, Darzynkiewicz Z. et al. (2000) *Methods in Enzymol.* 322:18-39); detection of apoptosis by annexin V labeling (as described in, for example, Bossy-Wetzel E. et al. (2000) *Methods in Enzymol.* 322:15-18); transient transfection assays for cell death genes (as described in, for example, Miura M. et al. (2000) *Methods in Enzymol.* 322:480-92); and assays that detect DNA cleavage in apoptotic cells, e.g., apoptotic plasma cells (as described in, for example, Kauffman S. H. et al. (2000) *Methods in Enzymol.* 322:3-15). Apoptosis can also be measured by propidium iodide staining or by TUNEL assay. In another embodiment, the transcription of genes associated with a cell signaling pathway involved in apoptosis (e.g., JNK) can be detected using standard methods.

In another embodiment, mitochondrial inner membrane permeabilization can be measured in intact cells by loading the cytosol or the mitochondrial matrix with a die that does not normally cross the inner membrane, e.g., calcein (Bernardi et al. 1999. Eur. J. Biochem. 264:687; Lemasters, J., J. et al. 1998. Biochem. Biophys. Acta 1366:177. In another embodiment, mitochondrial inner membrane permeabilization can be assessed, e.g., by determining a change in the mitochondrial inner membrane potential ($\Delta\Psi m$). For example, cells can be incubated with lipophilic cationic fluorochromes such as DiOC6 (Gross et al. 1999. Genes Dev. 13:1988) (3,3'dihexyloxacarbocyanine iodide) or JC-1(5,5', 6,6'-tetrachloro-1,1',3,3'-tetraethylbenzimidazolylcarbocyanine iodide). These dyes accumulate in the mitochondrial matrix, driven by the $\Psi m$. Dissipation results in a reduction of the fluorescence intensity (e.g., for DiOC6 (Gross et al. 1999. Genes Dev. 13:1988) or a shift in the emission spectrum of the dye. These changes can be measured by cytofluorometry or microscopy.

In yet another embodiment, the ability of a compound to modulate translocation of KRC to the nucleus can be determined. Translocation of KRC to the nucleus can be measured, e.g., by nuclear translocation assays in which the emission of two or more fluorescently-labeled species is detected simultaneously. For example, the cell nucleus can be labeled with a known fluorophore specific for DNA, such as Hoechst 33342. The KRC protein can be labeled by a variety of methods, including expression as a fusion with GFP or contacting the sample with a fluorescently-labeled antibody specific for KRC. The amount KRC that translocates to the nucleus can be determined by determining the amount of a first fluorescently-labeled species, i.e., the nucleus, that is distributed in a correlated or anti-correlated manner with respect to a second fluorescently-labeled species, i.e., KRC, as described in U.S. Pat. No. 6,400,487, the contents of which are hereby incorporated by reference.

In one embodiment, the effect of a compound on a JNK signaling pathway can be determined. The JNK group of MAP kinases is activated by exposure of cells to environmental stress or by treatment of cells with pro-inflammatory cytokines. A combination of studies involving gene knockouts and the use of dominant-negative mutants have implicated both MKK4 and MKK7 in the phosphorylation and activation of JNK. Targets of the JNK signal transduction pathway include the transcription factors ATF2 and c-Jun. JNK binds to an $NH_2$-terminal region of ATF2 and c-Jun and phosphorylates two sites within the activation domain of each transcription factor, leading to increased transcriptional activity. JNK is activated by dual phosphorylation on Thr-183 and Tyr-185. To determine the effect of a compound on a JNK signal transduction pathway, the ability of the compound to modulate the activation status of various molecules in the signal transduction pathway can be determined using standard techniques. For example, in one embodiment, the phosphorylation status of JNK can be examined by immunoblotting with the anti-ACTIVE-JNK antibody (Promega), which specifically recognizes the dual phosphorylated TPY motif.

In another embodiment, the effect of a compound on an NFkB signal transduction pathway can be determined. The ability of the compound to modulate the activation status of various components of the NFkB pathway can be determined using standard techniques. NFkB constitutes a family of Rel domain-containing transcription factors that play essential roles in the regulation of inflammatory, anti-apoptotic, and immune responses. The function of the NFkB/Rel family members is regulated by a class of cytoplasmic inhibitory proteins termed IBs that mask the nuclear localization domain of NFkB causing its retention in the cytoplasm. Activation of NFkB by TNF-$\alpha$ and IL-1 involves a series of signaling intermediates, which may converge on the NFkB-inducing kinase (NIK). This kinase in turn activates the 1B kinase (IKK) isoforms. These IKKs phosphorylate the two regulatory serines located in the N termini of IB molecules, triggering rapid ubiquitination and degradation of IB in the 26S proteasome complex. The degradation of IB unmasks a nuclear localization signal present in the NFkB complex, allowing its rapid translocation into the nucleus, where it engages cognate B enhancer elements and modulates the transcription of various NFkB-responsive target genes. In one embodiment, the ability of a compound to modulate one or more of: the status of NFkB inhibitors, the ability of NFkB to translocate to the nucleus, or the activation of NFkB dependent gene transcription can be measured.

In one embodiment, the ability of a compound to modulate AP-1 activity can be measured. The AP-1 complex is comprised of the transcription factors Fos and Jun. The AP-1 complex activity is controlled by regulation of Jun and Fos transcription and by posttranslation modification, for example, the activation of several MAPKS, ERK, p38 and JN, is required for AP-1 transcriptional activity. In one embodiment, the modulation of transcription mediated by AP-1 can be measured. In another embodiment, the ability of a compound to modulate the activity of AP-1, e.g., by modulating its phosphorylation or its ubiquitination can be measured. In one embodiment, the ubiquitination of AP-1 can be measured using techniques known in the art. In another embodiment, the degradation of AP-1 (or of c-Jun and/or c-Fos) can be measured using known techniques.

The loss of AP-1 has been associated with T cell anergy. Accordingly, in one embodiment, the ability of a test compound to modulate T cell anergy can be determined, e.g, by assaying secondary T cell responses. If the T cells are unresponsive to the secondary activation attempts, as determined by IL-2 synthesis and/or T cell proliferation, a state of anergy or has been induced. Standard assay procedures can be used to measure T cell anergy, for example, T cell proliferation can be measured, for example, by assaying [$^3$H] thymidine incorporation. In another embodiment, signal transduction can be measured, e.g., activation of members of the MAP kinase cascade or activation of the AP-1 complex can be measured. In another embodiment, intracellular calcium mobilization, protein levels members of the NFAT cascade can be measured.

In another embodiment, the effect of a compound on Ras and Rac activity can be measured using standard techniques. In one embodiment, actin polymerization, e.g., by measuring the immunofluorescence of F-actin can be measured.

In another embodiment, the effect of the compound on ubiquitination of, for example, AP1, SMAD, TRAF, RSK2, and/or Runx2, can be measured, by, for example in vitro or in vivo ubiquitination assays. In vitro ubiquitination assays are described in, for example, Fuchs, S. Y., Bet al. (1997) J. Biol. Chem. 272:32163-32168. In vivo ubiquitination assays are described in, for example, Treier, M., L. et al. (1994) Cell 78:787-798.

In another embodiment, the effect of the compound on the degradation of, for example, a KRC target molecule and/or a KRC binding partner, can be measured by, for example, coimmunoprecipitation of KRC, e.g., full-length KRC and/or a fragment thereof, with, e.g., SMAD, GATA3, Runx2, RSK2, TRAF, Jun, and/or Fos. Western blotting of the coimmunoprecipitate and probing of the blots with antibodies to KRC and the KRC target molecule and/or a KRC binding partner can be quantitated to determine whether degradation has occurred. Pulse-chase experiments can also be performed to determine protein levels.

In one embodiment, the ability of the compound to modulate TGFβ signaling in B cells can be measured. For example, as described herein, KRC is a coactivator of GLα promoter activity and a corepressor of the osteocalcin gene. In the absence of KRC, GLα transcription is diminished in B cells, and osteocalcin gene transcription is augmented in osteoblasts. Accordingly, in one embodiment, the ability of the compound to modulate TGFβ signaling in B cells can be measured by measuring the transcription of GLα. In another embodiment, osteocalcin gene transcription can be measured. In one embodiment, RT-PCR is used to measure the transcription. Furthermore, given the ability of KRC to interact with SMAD and drive the transcription of a SMAD reporter construct, the ability of a compound to modulate TGFβ signaling in B cells can be measured by measuring the transcriptional ability of SMAD. In one embodiment, SMAD, or a fragment thereof, e.g., a basic SMAD-binding element, is operably linked to a luciferase reporter gene. Other TGFβ regulated genes are known in the art (e.g., Massague and Wotton. 2000 EMBO 19:1745.).

In one embodiment, the ability of the compound to modulate ATF4 signaling in osteoblasts can be measured. For example, as described herein, overexpression of KRC inhibits ATF4-driven transcription and RSK2-mediated potentiation of ATF4 function. In the absence of KRC, ATF4 mRNA and protein levels are elevated, hyperphosphorylated ATF4 accumulates, and RSK2 autophosphorylation is increased. Accordingly, in one embodiment, the ability of a compound to modulate ATF4 signaling in osteoblasts can be measured by, for example, measuring the transcription of ATF4. In another embodiment, the phosphorylation of ATF4 is measured. In yet another embodiment, the autophosphorylation of RSK2 is measured. Phosphorylation can be determined by, for example, the use of in vitro kinase assays, and the autophosphorylation of a protein such as RSK2, can be measured by, for example, immunoblotting with antibodies specific for phosphorylated- and/or unphosphorylated forms of the protein, and/or immunoblotting with an antibody that recognizes phosphorylated serine/threonine preceeded by two upstream arginine residues, a consensus motif for Rsk protein substrates.

In another embodiment, the ability of the compound to modulate bone formation and mineralization can be measured. For example, as described herein, animals deficient in KRC develop an osteosclerotic phenotype associated due to augmented osteoblast activity and bone formation. The formation of a multimeric complex between KRC, Runx2, Smad3, and/or the E3 ubiquitin ligase, WWP1 inhibits Runx2 function due to the ability of WWP1 to promote Runx2 polyubiquitination and proteasome-dependent degradation. KRC is an integral and required component of this complex, since its absence in osteoblasts results in elevated levels of Runx2 protein, enhanced Runx2 transcriptional activity, elevated transcription of Runx2 target genes, and profoundly increased bone formation in vivo. Similarly, the formation of a multimeric complex between KRC, RSK2, and/or the E3 ubiquitin ligase, WWP1 inhibits RSK2 function due to the ability of WWP1 to promote RSK2 polyubiquitination and the ability of KRC and WWP1 to inhibit RSK2 autophosphorylation. In the absence of KRC, RSK2 autophosphorylation is increased demonstrating an critical role of KRC in the regulation of RSK2 function. Various in vitro techniques for determining the ability of compound to modulate bone formation and mineralization are known to the skilled artisan. For example, skeletal architecture can be assayed by digital radiography of, trabeculation (i.e., the anastomosing bony spicules in cancellous bone which form a meshwork of intercommunicating spaces that are filled with bone marrow) can be determined by three-dimensional μ-QCT imaging, and by analyses of bone cross-sections. In addition, trabecular number, trabecular thickness, bone volume per tissue volume (BV/TV), and bone mineral density (BMD) can also be determined by μ-QCT imaging. These analyses can be performed on whole skeleton preparations or individual bones. Mineralized bone and non-mineralized cartilage formation can be determined by histochemical analyses, such as by alizarin red/alcian blue staining. To assay a compound for an effect on osteoblast function versus osteoclast function, in vitro osteoclast differentiation assays are performed by culturing bone marrow (BM) in the presence of M-CSF and RANKL to generate TRAP+ osteoclasts. In vivo determinations of whether a compound effects osteoblast function or osteoclast can be performed by, for example, bone marrow transfers. In addition, various histomorphometric parameters can be analyzed to determine bone formation rates. For example, dual calcein-labeling of bone visualized with fluorescent micrography allows the determination of bone formation rate (BFR), which is calculated by multiplying the mineral apposition rate (MAR), which is a reflection of the bone formation capabilities of osteoblasts, by the area of mineralized surface per bone surface (MS/BS). In addition, the total osteoblast surface, which a reliable indicator of osteoblast population, can be measured, as can osteoid thickness, i.e., the thickness of bone that has not undergone calcification. Sections of bone can also be analyzed by staining with Von Kossa and Toluidine Blue for analysis of in vivo bone formation. The ex vivo culturing of osteoblast precursors and immature osteoblasts can also be performed to determine if cells possess the capacity to form mineralized nodules, which reflects the generation of extracellular matrix, i.e., the mineralized matrix of bone. Furthermore, these cultures can be assayed for their proliferative ability, e.g., by cell counting, and can be stained for the presence of various markers of bone formation, such as for example, alkaline phosphatase. These same cultures can also be used for various analyses of mRNA and protein production of numerous molecules known to be involved in bone formation and mineralization, and osteoclastogenesis, such as, for example, BSP, ColI(α)1, and OCN, ALP, LRP5, Osterix, Runx2, RANKL, RSK2, and ATF4.

The ability of the test compound to modulate KRC (or a molecule in a signal transduction pathway involving to KRC) binding to a substrate or target molecule (e.g., TRAF, GATA3, SMAD2, SMAD3, CBFβ, WWP1, AP-1, RSK2, and/or Runx2, in the case of KRC) can also be determined. Determining the ability of the test compound to modulate KRC binding to a target molecule (e.g. a binding partner such as a substrate) can be accomplished, for example, by coupling the target molecule with a radioisotope or enzymatic label such that binding of the target molecule to KRC or a molecule in a signal transduction pathway involving KRC can be determined by detecting the labeled KRC target molecule in a complex. Alternatively, KRC be coupled with a radioisotope or enzymatic label to monitor the ability of a test compound to modulate KRC binding to a target molecule in a complex. Determining the ability of the test compound to bind to KRC can be accomplished, for example, by coupling the compound with a radioisotope or enzymatic label such that binding of the compound to KRC can be determined by detecting the labeled compound in a complex. For example, targets can be labeled with $^{125}I$, $^{35}S$, $^{14}C$, or $^3H$, either directly or indirectly, and the radioisotope detected by direct counting of radioemmission or by scintillation counting. Alternatively, compounds can be labeled, e.g., with, for example, horseradish peroxidase, alkaline phosphatase, or luciferase, and the enzymatic label detected by determination of conversion of an appropriate substrate to product.

In another embodiment, the ability of KRC or a molecule in a signal transduction pathway involving KRC to be acted on by an enzyme or to act on a substrate can be measured. For example, in one embodiment, the effect of a compound on the phosphorylation of KRC can be measured using techniques that are known in the art.

It is also within the scope of this invention to determine the ability of a compound to interact with KRC or a molecule in a signal transduction pathway involving KRC without the labeling of any of the interactants. For example, a microphysiometer can be used to detect the interaction of a compound with a KRC molecule without the labeling of either the compound or the molecule (McConnell, H. M. et al. (1992) Science 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and Exemplary target molecules of KRC include: Jun, TRAF (e.g., TRAF2) GATA3, SMAD, e.g., SMAD2 and SMAD3, CBFβ, RSK2, and/or Runx2.

In another embodiment, a different (i.e., non-KRC) molecule acting in a pathway involving KRC that acts upstream or downstream of KRC can be included in an indicator composition for use in a screening assay. Compounds identified in a screening assay employing such a molecule would also be useful in modulating KRC activity, albeit indirectly. For example, the ability of TRAF (e.g., TRAF2) to activate NFKβ dependent gene expression can be measured, or the ability of SMAD to activate TGFβ-dependent gene transcription can be measured.

The cells used in the instant assays can be eukaryotic or prokaryotic in origin. For example, in one embodiment, the cell is a bacterial cell. In another embodiment, the cell is a fungal cell, e.g., a yeast cell. In another embodiment, the cell is a vertebrate cell, e.g., an avian or a mammalian cell. In a preferred embodiment, the cell is a human cell.

The cells of the invention can express endogenous KRC or another protein in a signaling pathway involving KRC or can be engineered to do so. For example, a cell that has been engineered to express the KRC protein and/or a non protein which acts upstream or downstream of can be produced by introducing into the cell an expression vector encoding the protein.

Recombinant expression vectors that can be used for expression of KRC or a molecule in a signal transduction pathway involving KRC (e.g., a protein which acts upstream or downstream of KRC) are known in the art. For example, the cDNA is first introduced into a recombinant expression vector using standard molecular biology techniques. A cDNA can be obtained, for example, by amplification using the polymerase chain reaction (PCR) or by screening an appropriate cDNA library. The nucleotide sequences of cDNAs for or a molecule in a signal transduction pathway involving (e.g., human, murine and yeast) are known in the art and can be used for the design of PCR primers that allow for amplification of a cDNA by standard PCR methods or for the design of a hybridization probe that can be used to screen a cDNA library using standard hybridization methods.

Following isolation or amplification of a cDNA molecule encoding KRC or a non-KRC molecule in a signal transduction pathway involving KRC the DNA fragment is introduced into an expression vector. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid molecule in a form suitable for expression of the nucleic acid in a host cell, which means that the recombinant expression vectors include one or more regulatory sequences, selected on the basis of the host cells to be used for expression and the level of expression desired, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell, those which direct expression of the nucleotide sequence only in certain host cells (e.g., tissue-specific regulatory sequences) or those which direct expression of the nucleotide sequence only under certain conditions (e.g. inducible regulatory sequences).

When used in mammalian cells, the expression vector's control functions are often provided by viral regulatory elements. For example, commonly used promoters are derived from polyoma virus, adenovirus, cytomegalovirus and Simian Virus 40. Non-limiting examples of mammalian expression vectors include pCDM8 (Seed, B., (1987) *Nature* 329: 840) and pMT2PC (Kaufman et al. (1987), *EMBO J.* 6:187-195). A variety of mammalian expression vectors carrying different regulatory sequences are commercially available. For constitutive expression of the nucleic acid in a mammalian host cell, a preferred regulatory element is the cytomegalovirus promoter/enhancer. Moreover, inducible regulatory systems for use in mammalian cells are known in the art, for example systems in which gene expression is regulated by heavy metal ions (see e.g., Mayo et al. (1982) *Cell* 29:99-108; Brinster et al. (1982) *Nature* 296:39-42; Searle et al. (1985) *Mol. Cell. Biol.* 5:1480-1489), heat shock (see e.g., Nouer et al. (1991) in *Heat Shock Response*, e.d. Nouer, L., CRC, Boca Raton, Fla., pp 167-220), hormones (see e.g., Lee et al. (1981) *Nature* 294:228-232; Hynes et al. (1981) *Proc. Natl. Acad. Sci. USA* 78:2038-2042; Klock et al. (1987) *Nature* 329:734-736; Israel & Kaufman (1989) *Nucl. Acids Res.* 17:2589-2604; and PCT Publication No. WO 93/23431), FK506-related molecules (see e.g., PCT Publication No. WO 94/18317) or tetracyclines (Gossen, M. and Bujard, H. (1992) *Proc. Natl. Acad. Sci. USA* 89:5547-5551; Gossen, M. et al. (1995) *Science* 268:1766-1769; PCT Publication No. WO 94/29442; and PCT Publication No. WO 96/01313). Still further, many tissue-specific regulatory sequences are known in the art, including the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Baneiji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916) and mammary gland-specific promoters (e.g. milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the $\alpha$-fetoprotein promoter (Campes and Tilghman (1989) *Genes Dev.* 3:537-546).

Vector DNA can be introduced into mammalian cells via conventional transfection techniques. As used herein, the various forms of the term "transfection" are intended to refer to a variety of art-recognized techniques for introducing foreign nucleic acid (e.g., DNA) into mammalian host cells, including calcium phosphate co-precipitation, DEAE-dextran-mediated transfection, lipofection, or electroporation. Suitable methods for transfecting host cells can be found in Sambrook et al. (*Molecular Cloning: A Laboratory Manual*, 2nd Edition, Cold Spring Harbor Laboratory press (1989)), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding, a selectable marker can be introduced into a host cell on a separate vector from that encoding KRC or, more preferably, on the same vector. Cells stably transfected with the introduced nucleic acid can be identified by drug selection (e.g., cells that have incorporated the selectable marker gene will survive, while the other cells die).

In one embodiment, within the expression vector coding sequences are operatively linked to regulatory sequences that allow for constitutive expression of the molecule in the indicator cell (e.g., viral regulatory sequences, such as a cytomegalovirus promoter/enhancer, can be used). Use of a recombinant expression vector that allows for constitutive expression of KRC or a molecule in a signal transduction pathway involving KRC in the indicator cell is preferred for identification of compounds that enhance or inhibit the activity of the molecule. In an alternative embodiment, within the expression vector the coding sequences are operatively linked to regulatory sequences of the endogenous gene for KRC or a molecule in a signal transduction pathway involving KRC (i.e., the promoter regulatory region derived from the endogenous gene). Use of a recombinant expression vector in which expression is controlled by the endogenous regulatory sequences is preferred for identification of compounds that enhance or inhibit the transcriptional expression of the molecule.

In yet another aspect of the invention, the KRC protein or fragments thereof can be used as "bait protein" e.g., in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with KRC ("binding proteins" or "bp") and are involved in KRC activity. Such KRC-binding proteins are also likely to be involved in the propagation of signals by the KRC proteins or KRC targets such as, for example, downstream elements of an KRC-mediated signaling pathway. Alternatively, such KRC-binding proteins can be KRC inhibitors.

The two-hybrid system is based on the modular nature of most transcription factors, which consist of separable DNA-binding and activation domains. Briefly, the assay utilizes two different DNA constructs. In one construct, the gene that codes for an KRC protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an KRC dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the KRC protein or a molecule in a signal transduction pathway involving KRC.

B. Cell-Free Assays

In another embodiment, the indicator composition is a cell free composition. KRC or a non-KRC protein in a signal transduction pathway involving KRC expressed by recombinant methods in a host cells or culture medium can be isolated from the host cells, or cell culture medium using standard methods for protein purification. For example, ion-exchange chromatography, gel filtration chromatography, ultrafiltration, electrophoresis, and immunoaffinity purification with antibodies can be used to produce a purified or semi-purified protein that can be used in a cell free composition. Alternatively, a lysate or an extract of cells expressing the protein of interest can be prepared for use as cell-free composition.

In one embodiment, compounds that specifically modulate KRC activity or the activity of a molecule in a signal transduction pathway involving KRC are identified based on their ability to modulate the interaction of KRC with a target molecule to which KRC binds. The target molecule can be a DNA molecule, e.g., a KRC-responsive element, such as the regulatory region of a chaperone gene) or a protein molecule. Suitable assays are known in the art that allow for the detection of protein-protein interactions (e.g., immunoprecipitations, two-hybrid assays and the like) or that allow for the detection of interactions between a DNA binding protein with a target DNA sequence (e.g., electrophoretic mobility shift assays, DNAse I footprinting assays and the like). By performing such assays in the presence and absence of test compounds, these assays can be used to identify compounds that modulate (e.g., inhibit or enhance) the interaction of KRC with a target molecule.

In one embodiment, the amount of binding of KRC or a molecule in a signal transduction pathway involving KRC to the target molecule in the presence of the test compound is greater than the amount of binding of KRC to the target molecule in the absence of the test compound, in which case the test compound is identified as a compound that enhances binding of KRC to a target. In another embodiment, the amount of binding of the KRC to the target molecule in the presence of the test compound is less than the amount of binding of the KRC (or e.g., Jun, TRAF, GATA3, SMAD2, SMAD3, Runx2, and/or WWP1) to the target molecule in the absence of the test compound, in which case the test compound is identified as a compound that inhibits binding of KRC to the target. Binding of the test compound to KRC or a molecule in a signal transduction pathway involving KRC can be determined either directly or indirectly as described above. Determining the ability of KRC protein to bind to a test compound can also be accomplished using a technology such as real-time Biomolecular Interaction Analysis (BIA) (Sjolander, S, and Urbaniczky, C. (1991) *Anal. Chem.* 63:2338-2345; Szabo et al. (1995) *Curr. Opin. Struct. Biol.* 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In the methods of the invention for identifying test compounds that modulate an interaction between KRC (or e.g., Jun, TRAF, GATA3, SMAD2, SMAD3, Runx2, RSK2, and/or WWP1) protein and a target molecule, a polypeptide comprising the complete KRC amino acid sequence can be used in the method, or, alternatively, a polypeptide comprising only portions of the protein can be used. For example, an isolated KRC interacting domain (e.g., consisting of amino acids 204-1055 or a larger subregion including an interacting domain) can be used. In another embodiment, a polypeptide comprising the Runt domain of Runx2 or the isolated domain can be used in an assay of the invention. In yet another embodiment, the PPXY motif of the Runt domain of Runx2 can be used in an assay of the invention. An assay can be used to identify test compounds that either stimulate or inhibit the interaction between the KRC protein and a target molecule. A test compound that stimulates the interaction between the protein and a target molecule is identified based upon its ability to increase the degree of interaction between, e.g., KRC and a target molecule as compared to the degree of interaction in the absence of the test compound and such a compound would be expected to increase the activity of KRC in the cell. A test compound that inhibits the interaction between the protein and a target molecule is identified based upon its ability to decrease the degree of interaction between the protein and a target molecule as compared to the degree of interaction in the absence of the compound and such a compound would be expected to decrease KRC activity.

In one embodiment of the above assay methods of the present invention, it may be desirable to immobilize either KRC (or a molecule in a signal transduction pathway involving KRC, e.g., Jun, TRAF, GATA3, SMAD2, SMAD3, Runx2, RSK2, and/or WWP1) or a respective target molecule for example, to facilitate separation of complexed from uncomplexed forms of one or both of the proteins, or to accommodate automation of the assay. Binding of a test compound to a KRC or a molecule in a signal transduction pathway involving KRC, or interaction of an KRC protein (or a molecule in a signal transduction pathway involving KRC) with a target molecule in the presence and absence of a test compound, can be accomplished in any vessel suitable for containing the reactants. Examples of such vessels include microtitre plates, test tubes, and micro-centrifuge tubes. In one embodiment, a fusion protein can be provided in which a domain that allows one or both of the proteins to be bound to a matrix is added to one or more of the molecules. For example, glutathione-S-transferase fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or KRC protein, and the mixture incubated under conditions conducive to complex formation (e.g., at physiological conditions for salt and pH). Following incubation, the beads or microtitre plate wells are washed to remove any unbound components, the matrix is immobilized in the case of beads, and complex formation is determined either directly or indirectly, for example, as described above. Alternatively, the complexes can be dissociated from the matrix, and the level of binding or activity determined using standard techniques.

Other techniques for immobilizing proteins on matrices can also be used in the screening assays of the invention. For example, either an KRC protein or a molecule in a signal transduction pathway involving KRC, or a target molecule can be immobilized utilizing conjugation of biotin and streptavidin. Biotinylated protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies which are reactive with protein or target molecules but which do not interfere with binding of the protein to its target molecule can be derivatized to the wells of the plate, and unbound target or KRC protein is trapped in the wells by antibody conjugation. Methods for detecting such complexes, in addition to those described above for the GST-immobilized complexes, include immunodetection of complexes using antibodies reactive with KRC or a molecule in a signal transduction pathway involving KRC or target molecule, as well as enzyme-linked assays which rely on detecting an enzymatic activity associated with the KRC protein or target molecule.

C. Assays Using Knock-Out Cells

In another embodiment, the invention provides methods for identifying compounds that modulate a biological effect of KRC or a molecule in a signal transduction pathway involving KRC using cells deficient in KRC (or e.g., Jun, TRAF, GATA3, SMAD2, SMAD3, Runx2, ATF4, RSK2, and/or WWP1). As described in the Examples, inhibition of KRC activity (e.g., by disruption of the KRC gene) in cells results, e.g., in increased bone formation and mineralization. Thus, cells deficient in KRC or a molecule in a signal transduction pathway involving KRC can be used identify agents that modulate a biological response regulated by KRC by means other than modulating KRC itself (i.e., compounds that "rescue" the KRC deficient phenotype). Alternatively, a "conditional knock-out" system, in which the gene is rendered non-functional in a conditional manner, can be used to create deficient cells for use in screening assays. For example, a tetracycline-regulated system for conditional disruption of a gene as described in WO 94/29442 and U.S. Pat. No. 5,650,298 can be used to create cells, or animals from which cells can be isolated, be rendered deficient in KRC (or a molecule in a signal transduction pathway involving KRC e.g., Jun, TRAF, GATA3, SMAD2, SMAD3, Runx2, CBFβ, ATF4, RSK2, and/or WWP1) in a controlled manner through modulation of the tetracycline concentration in contact with the cells. Specific cell types, e.g., lymphoid cells (e.g., thymic, splenic and/or lymph node cells) or purified cells such as T cells, B cells, osteoblasts, osteoclasts, from such animals can be used in screening assays. In one embodiment, the entire 5.4 kB exon 2 of KRC can be replaced, e.g., with a neomycin cassette, resulting in an allele that produces no KRC protein. This embodiment is described in the appended examples.

In the screening method, cells deficient in KRC or a molecule in a signal transduction pathway involving KRC can be contacted with a test compound and a biological response regulated by KRC or a molecule in a signal transduction pathway involving KRC can be monitored. Modulation of the response in cells deficient in KRC or a molecule in a signal transduction pathway involving KRC (as compared to an appropriate control such as, for example, untreated cells or cells treated with a control agent) identifies a test compound as a modulator of the KRC regulated response.

In one embodiment, the test compound is administered directly to a non-human knock out animal, preferably a mouse (e.g., a mouse in which the KRC gene or a gene in a signal transduction pathway involving KRC is conditionally disrupted by means described above, or a chimeric mouse in which the lymphoid organs are deficient in KRC or a molecule in a signal transduction pathway involving KRC as described above), to identify a test compound that modulates the in vivo responses of cells deficient in KRC. In another embodiment, cells deficient in KRC are isolated from the non-human KRC deficient animal or a molecule in a signal transduction pathway involving KRC deficient animal, and contacted with the test compound ex vivo to identify a test compound that modulates a response regulated by KRC in the cells Cells deficient in KRC or a molecule in a signal transduction pathway involving KRC can be obtained from a non-human animals created to be deficient in KRC or a molecule in a signal transduction pathway involving KRC. Preferred non-human animals include monkeys, dogs, cats, mice, rats, cows, horses, goats and sheep. In preferred embodiments, the deficient animal is a mouse. Mice deficient in KRC or a molecule in a signal transduction pathway involving KRC can be made using methods known in the art. One example of such a method and the resulting KRC heterozygous and homozygous animals is described in the appended examples. Non-human animals deficient in a particular gene product typically are created by homologous recombination. In an exemplary embodiment, a vector is prepared which contains at least a portion of the gene into which a deletion, addition or substitution has been introduced to thereby alter, e.g., functionally disrupt, the endogenous KRC. The gene preferably is a mouse gene. For example, a mouse KRC gene can be isolated from a mouse genomic DNA library using the mouse KRC cDNA as a probe. The mouse KRC gene then can be used to construct a homologous recombination vector suitable for modulating an endogenous KRC gene in the mouse genome. In a preferred embodiment, the vector is designed such that, upon homologous recombination, the endogenous gene is functionally disrupted (i.e., no longer encodes a functional protein; also referred to as a "knock out" vector).

Alternatively, the vector can be designed such that, upon homologous recombination, the endogenous gene is mutated or otherwise altered but still encodes functional protein (e.g., the upstream regulatory region can be altered to thereby alter the expression of the endogenous KRC protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced gene has homologously recombined with the endogenous gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In one embodiment of the screening assay, compounds tested for their ability to modulate a biological response regulated by KRC or a molecule in a signal transduction pathway involving KRC are contacted with deficient cells by administering the test compound to a non-human deficient animal in vivo and evaluating the effect of the test compound on the response in the animal.

The test compound can be administered to a non-knock out animal as a pharmaceutical composition. Such compositions typically comprise the test compound and a pharmaceutically acceptable carrier. As used herein the term "pharmaceutically acceptable carrier" includes any and all solvents, dispersion media, coatings, antibacterial and antifungal compounds, isotonic and absorption delaying compounds, and the like, compatible with pharmaceutical administration. The use of such media and compounds for pharmaceutically active substances is well known in the art. Except insofar as any conventional media or compound is incompatible with the active compound, use thereof in the compositions is contemplated. Supplementary active compounds can also be incorporated into the compositions. Pharmaceutical compositions are described in more detail below.

In another embodiment, compounds that modulate a biological response regulated by KRC or a signal transduction pathway involving KRC are identified by contacting cells deficient in KRC ex vivo with one or more test compounds, and determining the effect of the test compound on a read-out. In one embodiment, KRC deficient cells contacted with a test compound ex vivo can be readministered to a subject.

For practicing the screening method ex vivo, cells deficient, e.g., in KRC, Jun, TRAF, GATA3, SMAD2, SMAD3, Runx2, ATF4, RSK2, and/or WWP1, can be isolated from a non-human deficient animal or embryo by standard methods and incubated (i.e., cultured) in vitro with a test compound. Cells (e.g., T cells, B cells, and/or osteoblasts) can be isolated from e.g., KRC, Jun, TRAF, GATA3, SMAD2, SMAD3, Runx2, ATF4, RSK2, and/or WWP1, deficient animals by standard techniques. In another embodiment, the cells are isolated form animals deficient in one or more of KRC, Jun, TRAF, GATA3, SMAD2, SMAD3, Runx2, ATF4, RSK2, and/or WWP1.

In another embodiment, cells deficient in more than one member of a signal transduction pathway involving KRC can be used in the subject assays.

Following contact of the deficient cells with a test compound (either ex vivo or in vivo), the effect of the test compound on the biological response regulated by KRC or a molecule in a signal transduction pathway involving KRC can be determined by any one of a variety of suitable methods, such as those set forth herein, e.g., including light microscopic analysis of the cells, histochemical analysis of the cells, production of proteins, induction of certain genes, e.g., cytokine gene, such as IL-2, degradation of certain proteins, e.g., ubiquitination of certain proteins, as described herein.

D. Test Compounds

A variety of test compounds can be evaluated using the screening assays described herein. The term "test compound" includes any reagent or test agent which is employed in the assays of the invention and assayed for its ability to influence the expression and/or activity of KRC or a molecule in a signal transduction pathway involving KRC. More than one compound, e.g., a plurality of compounds, can be tested at the same time for their ability to modulate the expression and/or activity of, e.g., KRC in a screening assay. The term "screening assay" preferably refers to assays which test the ability of a plurality of compounds to influence the readout of choice rather than to tests which test the ability of one compound to influence a readout. Preferably, the subject assays identify compounds not previously known to have the effect that is being screened for. In one embodiment, high throughput screening can be used to assay for the activity of a compound.

In certain embodiments, the compounds to be tested can be derived from libraries (i.e., are members of a library of compounds). While the use of libraries of peptides is well established in the art, new techniques have been developed which have allowed the production of mixtures of other compounds, such as benzodiazepines (Bunin et al. (1992). *J. Am. Chem. Soc.* 114:10987; DeWitt et al. (1993). *Proc. Natl. Acad. Sci. USA* 90:6909) peptoids (Zuckermann. (1994). *J. Med. Chem.* 37:2678) oligocarbamates (Cho et al. (1993). *Science.* 261: 1303-), and hydantoins (DeWitt et al. supra). An approach for the synthesis of molecular libraries of small organic molecules with a diversity of 104-105 as been described (Carell et al. (1994). *Angew. Chem. Int. Ed. Engl.* 33:2059-; Carell et al. (1994) *Angew. Chem. Int. Ed. Engl.* 33:2061-).

The compounds of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145). Other exemplary methods for the synthesis of molecular libraries can be found in the art, for example in: Erb et al. (1994). *Proc. Natl. Acad. Sci. USA* 91:11422-; Horwell et al. (1996) *Immunopharmacology* 33:68-; and in Gallop et al. (1994); *J. Med. Chem.* 37:1233-.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); In still another embodiment, the combinatorial polypeptides are produced from a cDNA library.

Exemplary compounds which can be screened for activity include, but are not limited to, peptides, nucleic acids, carbohydrates, small organic molecules, and natural product extract libraries.

Candidate/test compounds include, for example, 1) peptides such as soluble peptides, including Ig-tailed fusion peptides and members of random peptide libraries (see, e.g., Lam, K. S. et al. (1991) *Nature* 354:82-84; Houghten, R. et al. (1991) *Nature* 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al. (1993) *Cell* 72:767-778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); 4) small organic and inorganic molecules (e.g., molecules obtained from combinatorial and natural product libraries); 5) enzymes (e.g., endoribonucleases, hydrolases, nucleases, proteases, synthatases, isomerases, polymerases, kinases, phosphatases, oxido-reductases and ATPases), and 6) mutant forms of KRC (e.g., dominant negative mutant forms of the molecule).

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997), *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds can be presented in solution (e.g. Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

Compounds identified in the subject screening assays can be used in methods of modulating one or more of the biological responses regulated by KRC. It will be understood that it may be desirable to formulate such compound(s) as pharmaceutical compositions (described supra) prior to contacting them with cells.

Once a test compound is identified that directly or indirectly modulates, e.g., KRC expression or activity, or a molecule in a signal transduction pathway involving KRC, by one of the variety of methods described hereinbefore, the selected test compound (or "compound of interest") can then be further evaluated for its effect on cells, for example by contacting the compound of interest with cells either in vivo (e.g., by administering the compound of interest to a subject) or ex vivo (e.g., by isolating cells from the subject and contacting the isolated cells with the compound of interest or, alternatively, by contacting the compound of interest with a cell line) and determining the effect of the compound of interest on the cells, as compared to an appropriate control (such as untreated cells or cells treated with a control compound, or carrier, that does not modulate the biological response).

The instant invention also pertains to compounds identified in the subject screening assays.

VI. Pharmaceutical Compositions

A pharmaceutical composition of the invention is formulated to be compatible with its intended route of administration. For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid; buffers such as acetates, citrates or phosphates and compounds for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition will preferably be sterile and should be fluid to the extent that easy syringability exists. It will preferably be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal compounds, for example, parabens, chlorobutanol, phenol, ascorbic acid, thimerosal, and the like. In many cases, it will be preferable to include isotonic compounds, for example, sugars, polyalcohols such as manitol, sorbitol, sodium chloride in the composition. Prolonged absorption of the injectable compositions can be brought about by including in the composition an compound which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

In one embodiment, the test compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from, e.g., Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

VII. Kits of the Invention

Another aspect of the invention pertains to kits for carrying out the screening assays, modulatory methods or diagnostic assays of the invention. For example, a kit for carrying out a screening assay of the invention can include an indicator composition comprising KRC or a molecule in a signal transduction pathway involving KRC, means for measuring a readout (e.g., protein secretion) and instructions for using the kit to identify modulators of biological effects of KRC. In another embodiment, a kit for carrying out a screening assay of the invention can include cells deficient in KRC or a molecule in a signal transduction pathway involving KRC, means for measuring the readout and instructions for using the kit to identify modulators of a biological effect of KRC.

In another embodiment, the invention provides a kit for carrying out a modulatory method of the invention. The kit can include, for example, a modulatory agent of the invention (e.g., KRC inhibitory or stimulatory agent) in a suitable carrier and packaged in a suitable container with instructions for use of the modulator to modulate a biological effect of KRC.

Another aspect of the invention pertains to a kit for diagnosing a disorder associated with a biological activity of KRC in a subject. The kit can include a reagent for determining expression of KRC (e.g., a nucleic acid probe for detecting KRC mRNA or an antibody for detection of KRC protein), a control to which the results of the subject are compared, and instructions for using the kit for diagnostic purposes.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

This invention is further illustrated by the following examples which should not be construed as limiting. The contents of all references, patents, and published patent applications cited throughout this application, as well as the figures and the sequence listing, are hereby incorporated by reference.

EXAMPLES

The following materials and methods were used throughout the Examples:

Generation of KRC-Deficient Mice.

The Shn3 targeting vector was created by cloning a 5-kb genomic fragment between Exons 3 and 4 and a 5.5-kb fragment of Exon 2 into the PGKNEO vector. The targeting construct was linearized and electroporated into ES cells. The gene-targeting vector replaced amino acids 1-108 of Exon 4 with a neomycin resistance cassette by homologous recombination, resulting in an allele that produces no Shn3 protein. Shn3-targeted ES clones were identified by Southern blot analysis and injected into C57BL/6 blastocysts. Shn3 ES cells transmitted the disrupted allele to 129/B6 offspring. Heterozygous pups were backcrossed to wild-type C57BL/6 mice for five generations before analysis. Mice analyzed in all studies are sex-matched littermates that are derived from heterozygous F5 intercrosses. Genotyping was performed by PCR on tail DNA using neomycin-specific primers and primers that span amino acids 1-103 of exon 4 of the Shn3 gene.

Bone and Cartilage Staining

Newborn mice were skinned, eviscerated and dehydrated in 95% ETOH overnight. The samples wee then transferred into acetone for an additional forty-eight hour incubation. Skeletal preparations were stained for four days using alcian blue and alizarin red as described previously (McLeod, M. J. (1980). *Teratology* 22, 299-301). Following staining, the samples were washed for thirty minutes, three times in 95% ETOH. The soft tissue was then cleared in 1% KOH.

Histomorphometric Analysis

For analysis of in vivo bone formation, calcein (1.6 mg/kg body weight) was administered by intraperitoneal injection to 2 month old WT and Shn3$^{-/-}$ mice at 8 days and 3 days prior to sacrifice. Tibias were harvested, cleared of soft tissue and fixed in 70% ethanol. Histomorphometric analysis was conducted by Development and Discovery Services at Charles River Laboratories. Briefly, bones were embedded in methylmethacrylate blocks without decalcification. Sections were stained with Von Kossa and Toluidine Blue or left unstained. Histomorphometry was performed in the secondary spongiosa approximately 1 mm below the lowest portion of the growth plate. Analysis was conducted with Bioquant True Colors software utilizing an Olympus BX-60 fluorescence-equipped microscope and an Optronics digital camera system.

Cell and Tissue Cultures

For in vitro osteoclatogenesis, bone marrow cells were isolated from the femur and tibia of mice in αMEM (Mediatech, Inc.). After red blood cell lysis, the cells were washed once and resuspended in αMEM+10% FBS. The bone marrow cells were then plated in a 48-well plate at a concentration of $2\times10^5$ cells per 250 µl of αMEM+10% FBS. The cells were then cultured for two days in the presence of 50 ng/ml M-CSF (Peprotech). After the initial two day culture period, the cells were then cultured for an additional five days in the presence of M-CSF (50 ng/ml) and either 25 ng/ml or 100 ng/ml RANKL (Peprotech). The cells were then fixed and stained for the presence of tartrate-resistant alkaline phosphatase (TRAP) per manufacture's instructions (Sigma).

Osteoblastic cells were isolated from calvariae of neonatal WT and Shn3$^{-/-}$ littermates as previously described (Yoshida, Y., et al. (2000). *Cell* 103, 1085-1097). Calvarial-derived cells were plated in αMEM+10% FBS+50 µg/ml ascorbic acid+5 mM β-glycerophosphate in a 6-well dish. Cells were harvested at a sub-confluent stage and replated in a 6-well dish at a concentration of $10^4$ cells/cm2 in αMEM+10% FBS+50 µg/ml ascorbic acid+5 mM β-glycerophosphate. For von Kossa staining, cells were fixed at day 21 of culture with 10% neutral buffered formalin and stained with 5% silver nitrate for 30 minutes. For ALP, cultures were fixed in 100% ethanol at day 14 of culture, and stained utilizing an alkaline phosphatase kit (Sigma) per manufacturer's instructions. For cell proliferation assays, calvarial-derived cells ($10^5$ cells/well at day 0) were plated in 6-well dish in αMEM+10% FBS+50 µg/ml ascorbic acid+5 mM β-glycerophosphate. Cells were harvested and counted at day 5 of culture utilizing a hemocytometer following trypan blue exclusion staining for cell viability.

Bone Marrow Transfers

Bone marrow cells were collected from the femur and tibia of 8-week old WT mice by flushing with RPMI 1640 (Mediatech, Inc.)+10% FBS using a syringe with a 26-gauge needle. Following RBC lysis, cells were washed in RPMI 1640+10% FBS and resuspended in PBS (Gibco). $1\times10^7$ WT bone marrow cells were then transferred by tail vein injection into γ-irradiated (1200 rads) 4-week old WT and Shn3$^{-/-}$ mice. The irradiated mice were analyzed by radiography four weeks after transfer.

Quantitative Real-Time PCR

For quantitative real-time PCR, total RNA was extracted from Shn3$^{-/-}$ and WT osteoblasts and at day 14 of culture utilizing Trizol (Invitrogen). Reverse transcription was performed on 1 µg RNA using iScript cDNA Synthesis kit (Bio-Rad) following the treatment of isolated RNA with amplification-grade DNase I (Invitrogen). Quantitative PCR was then performed on an ABI Prism 7700 Sequence Detection System (Applied Biosystems). PCR reaction were carried out in 25 µl volumes using SYBR Green PCR master mix (Applied Biosystems) and 0.2 µM of specific primers. Relative levels of mRNA for a specific gene between two samples were calculated utilizing the ΔΔCT method where the amount of cDNA in each sample was normalized to the β-actin Ct (Livak, K. J., and Schmittgen, T. D. (2001). *Methods* 25, 402-408).

Transient Transfections and Reporter Gene Assays

The preosteoblast cell line, MC3T3-E1 Subclone 4, and the murine mesenchymal stem cell line, C3H10T1/2, were obtained from ATCC and maintained in DMEM (Mediatech, Inc.)+10% FBS. For transient transfections, cells were seeded overnight in a 12-well dish at a concentration of $8\times10^4$ cells/well. Cells were then transfected with a luciferase reporter gene plasmid and the different combinations of expression constructs, as indicated, using Effectene transfection reagent (Qiagen). Total amounts of transfected DNA were kept constant by supplementing with control empty expression vector plasmids as needed. All cells were cotransfected with pRL-TK (Promega) as a normalization control for transfection efficiency. Forty-eight hours after transfection, cells were harvested and lysed in 1× Passive Lysis Buffer (Promega). Luciferase assays were performed using the Dual-Luciferase Reporter Assay System (Promega). The Shn3 expression plasmid has been described previously (Oukka, M., et al. (2002). *Mol Cell* 9, 121-131).

Immunoprecipitation and Immunoblotting

For immunoprecipitation, 293T cells ($6\times10^6$ cells/dish) were plated in 10 cm dishes in DMEM+10% FBS and transiently transfected with Effectene transfection reagent. Thirty-six to forty-eight hours later, cells were harvested and lysed in TNT lysis buffer (20 mM Tris, pH 8.0, 200 mM NaCl, 0.5% Triton X-100) supplemented with protease inhibitors. Lysates were subjected to immunoprecipitation with agarose-conjugated anti-FLAG (M2, Sigma) or anti-Myc (9E10, Santa Cruz) monoclonal antibodies at 4° C. overnight. Immunoprecipitates were then washed three times in lysis buffer and subjected to SDS-PAGE followed by immunoblotting for Shn-3 (Oukka, M., et al. (2002). *Mol Cell* 9, 121-131), FLAG (M2, Sigma), or Myc (9E10, SantaCruz).

To detect the interaction between endogenous Shn3 and Runx2, MC3T3-E1 cells were grown to confluency in DMEM+10% fetal calf serum in 10 cm dishes. When cells reached confluency, medium was changed to αMEM+10% fetal calf serum supplemented with 10 mM β-glycerophosphate, 50 µM ascorbic acid, and with or without BMP-2 (100 ng/ml), as described (Zamurovic, N., et al. (2004). *J Biol Chem* 279, 37704-37715). Cells were differentiated for an additional 3-4 days. Eighteen-hours prior to lysis TGFβ (2 ng/ml, R+D Systems) was added to some cultures, and 2 hours prior to lysis MG132 (10 µM, Boston Biochem) was added to all cultures. Cells were harvested and lysed in TNT buffer. Lysates were subjected to immunoprecipitation with 3 µg anti-Runx2 antibody (Santa Cruz) or control rabbit IgG at 4° C. overnight. Protein A/G-agarose (Santa Cruz) was added to precipitate immune complexes, which were then washed five times with lysis buffer followed by SDS-PAGE and immunoblotting for Shn3.

Additional co-immunoprecipitation experiments were conducted with FLAG-epitope-tagged Runx2 deletion mutants. Full length (amino acids 1-521) contains QA, Runt and PST domains. QA mutant (amino acids 48-89) contains QA domain but lacks both Runt and PST domains. Runt mutant (amino acids 102-229) contains Runt and PST domain. Runt/PST mutant (amino acids 102-521) contains Runt and PST domain but lacks QA domain. Shn3 interaction with these mutants was determined by Western blot analysis with anti-Shn3 antibody following immunoprecipitation with anti-FLAG antibody.

To detect endogenous Atf4 and Runx2 protein levels in Shn3$^{-/-}$ and WT osteoblasts, calvarial osteoblast cultures at days 14 and 21 were lysed in RIPA buffer supplemented with protease inhibitors. Protein concentrations were determined and 50 µg protein per sample was resolved by SDS-PAGE followed by immunoblotting for Runx2 (EMD Biosciences), Atf4 (Santa Cruz), or Hsp90 (Santa Cruz).

Ubiquitination Assays

To detect ubiquitination of Runx2 in 293T cells, a previously established protocol was followed (Campanero, M. R., and Flemington, E. K. (1997). *Proc Natl Acad Sci USA* 94, 2221-2226). In brief, 293T cells were transiently transfected with combinations of His-Ub, FLAG-Runx2, Myc-WWP1, and Shn3. Thirty-six to forty-eight hours later, cells were treated with 10 µM MG132 for 2 hours. Cells were washed and lysed in buffer containing 6M guanidium-HCl. Ubiquitinated proteins were precipitated with Ni-NTA-agarose (Novagen), and washed in lysis buffer followed by wash buffer containing 25 mM Tris pH 6.8, 20 mM imidazole. Precipitates were resolved by SDS-PAGE and ubiquitinated FLAG-Runx2 was detected by immunoblotting with anti-FLAG (M2, Sigma) antibody.

To assay the ability of immunoprecipitated Runx2/Shn3 complexes to promote ubiquitination in vitro, various combinations of FLAG-Runx2 and Shn3 were transiently transfected in 293T cells as above. Thirty-six to forty-eight hours later, cells were treated with 10 µM MG132 for 2 hours. Cells were washed, lysed in TNT buffer, and anti-FLAG immunoprecipitations were performed as above. Immune complexes were washed in TNT buffer, then in ubiquitination assay (UA) buffer containing 50 mM Tris, pH 8, 50 mM NaCl, 1 mM DTT, 5 mM MgCl2, and 1 mM ATP. Immunoprecipitates were resuspended in UA buffer supplemented ubiquitin and biotinylated ubiquitin (Boston Biochem) with or without recombinant E1, and E2 (UbcH5a and UbcH7, Boston Biochem). Ubiquitination reactions were allowed to proceed at 30° C. for two hours. Reactions were subsequently resolved by SDS-PAGE, transferred to PVDF membranes, and ubiquitinated proteins were visualized by blotting with streptavidin-HRP (Zymed).

Pulse-Chase Analysis 293T cells (1×10$^6$ cells) were transiently transfected with FLAG-Runx2 (200 ng) with or without Shn3 (1 µg) in 6 well plates. After thirty-six hours, cells were washed and incubated in cysteine/methionine-free medium for one hour. Cells were then labeled with 0.1 mCi/ml S$^{35}$-labelled cysteine/methionine for one hour. Next, cells were chased in medium containing excess non-radioactive cysteine/methionine for the indicated times. Cells were collected and lysed in TNT buffer supplemented with protease inhibitors, and anti-FLAG immunoprecipitations (M2 agarose slurry, Sigma) were performed at 4° C. overnight. Immunoprecipitates were washed four times in lysis buffer, resolved by SDS-PAGE, and immunoprecipitated proteins were visualized by fluography and quantified with PhosphoImager.

Example 1

Generation of Shn3 Deficient Mice

To investigate the function of Shn3 in vivo, mice bearing a null mutation in the murine Shn3 gene were generated by homologous recombination. Exon 4 of the Shn3 gene, on mouse chromosome 4, contains 5.4 kB of DNA that includes the ATG start codon as well as the coding sequence for eighty-percent of the entire protein. When the ATG start codon in Exon 4 was replaced with a neomycin-resistance cassette, it resulted in a null Shn3 allele that produced no detectable mRNA or protein. The targeted Shn3 allele was maintained at expected frequencies as 129/B6 Shn3 heterozygous mice. All subsequent experiments were performed using Shn3$^{-/-}$ and WT mice backcrossed at least five generations to C57BL/6 mice.

Example 2

Increased Bone Mass in Shn3 Deficient Mice

Homozygous Shn3 mutant (Shn3$^{-/-}$) mice were born at the expected Mendelian ratio and were healthy with no apparent gross phenotypic abnormalities in the major organs examined. However, analysis of 8-week old wild-type (WT) and Shn3$^{-/-}$ mice by three-dimensional µ-QCT digital radiography showed an increased radiopacity in the long bones of mature homozygous mutant mice. Further analysis of the skeletal architecture in these mice by two-dimensional µ-QCT revealed a dramatic increase in trabeculation present within the long bones and vertebrae of Shn3$^{-/-}$ mice. Serial cross-sections of femurs from Shn3$^{-/-}$ mice show that increased trabecular bone is present throughout the length of the femur, including distal regions of the diaphysis (FIG. 1E). In contrast, femurs isolated from WT mice show no trabeculation within the diaphysis and only modest levels of trabecular bone in the epiphysis and metaphysis of the femur. Quantitative analysis shows both the trabecular number and trabecular thickness is increased in the femurs of Shn3$^{-/-}$ mice. The increase in these two parameters results in the trabecular bone volume (BV/TV) of Shn3$^{-/-}$ mice being increased 4.5-fold over the trabecular bone volume observed in WT control mice. Additionally, the bone mineral density (BMD) of Shn3$^{-/-}$ mice is 250% that of WT mice.

The elevated bone mass present in mature Shn3$^{-/-}$ mice may result from dysfunctional prenatal bone development and/or a dysfunction in postnatal skeletal remodeling. To better understand if the increased bone mass present in Shn3$^{-/-}$ mice is a result of a dysregulation in bone morphogenesis, bone growth and development was analyzed in newborn WT and Shn3$^{-/-}$ mice. Whole skeletal preparations from P4 WT and Shn3$^{-/-}$ mice were stained with alizarin red/alcian blue to analyze mineralized bone and non-mineralized cartilage formation, respectively. Skeletal morphogenesis occurs normally in Shn3$^{-/-}$ mice analyzed at P4, with no premature cartilage mineralization being detected in those areas of the skeleton undergoing endochondral ossification. Collectively, these results suggest a postnatal role for Shn3 in skeletal remodeling in which Shn3 functions to inhibit bone formation.

Example 3

Shn3 is not Required for Osteoclast Differentiation or Function

To understand the role of Shn3 in skeletal remodeling, Shn3 expression was examining in those cell types involved in bone remodeling. Shn3 mRNA can be detected in whole bone, osteoblasts, and, to a lesser extent, in osteoclasts. The nonrestrictive pattern of Shn3 expression suggests that increased bone mass observed in the Shn3$^{-/-}$ mice may result from alterations in osteoblast and/or osteoclast function. To determine whether Shn3 functions to regulate osteoclast biology, in vitro osteoclast differentiation assays were performed by following previously established protocols in which bone marrow is harvested and cultured in the presence of M-CSF and RANKL to generate TRAP+ osteoclasts. Differentiation of bone marrow harvested from Shn3$^{-/-}$ mice resulted in similar numbers of multi-nucleated TRAP+ cells when compared to WT bone marrow cultured under identical conditions. Similar numbers of osteoclasts were also observed when WT and Shn3$^{-/-}$ splenocytes were cultured under conditions that promote osteoclastogenesis. These results suggest that Shn3 expression is dispensable for the differentiation of osteoclasts from precursor cells.

It has previously been reported that skeletal abnormalities that result from defects intrinsic to the osteoclast can be rescued following transfer of wild-type bone marrow into irradiated hosts (Li, J., et al. (2000). *Proc Natl Acad Sci USA* 97, 1566-1571). Rescue of the host phenotype occurs as a result of the WT donor osteoclasts, which are derived from hematopoietic progenitors, repopulating the microenvironment of the host bone and mediating bone resorption. To confirm that the skeletal phenotype observed in the Shn3$^{-/-}$ mice is not the result of an intrinsic defect in the osteoclast, a series of bone marrow transfer experiments were performed in which bone marrow cells harvested from WT mice were injected into lethally irradiated 4-week-old Shn3$^{-/-}$ mice. After four weeks, the mice were sacrificed and the femurs were analyzed by radiography. The transfer of WT bone marrow failed to reduce the amount of trabeculation present in the femurs of recipient Shn3$^{-/-}$ mice. These results further indicate that the increased bone mass present in the Shn3$^{-/-}$ mice is not the result of deficiencies in the osteoclast lineage, but rather, results from an increased osteoblast function and dysregulated bone formation.

Example 4

Increased Bone Formation Rate in Shn3-Deficient Mice

To determine if the increased bone mass seen in Shn3$^{-/-}$ mice results from alterations in bone formation, a number of histomorphometric parameters were analyzed in 8-week old Shn3$^{-/-}$ and WT mice, including calcein double-labeling and fluorescent micrography to examine in vivo bone formation rates. The increased distance between the two calcein labels observed in the tibial bones of Shn3$^{-/-}$ mice demonstrates that these mice have elevated levels of new bone formation when compared to WT mice. Quantitative analysis reveals the bone formation rate in Shn3$^{-/-}$ mice to be five-fold the rate observed in WT control animals. BFR is calculated by multiplying the mineral apposition rate (MAR), which is a reflection of the bone formation capabilities of osteoblasts, by the area of mineralized surface per bone surface (NS/BS). Additional histomorphometric analysis shows the Shn3$^{-/-}$ mice have increases in both mineral apposition rate (MAR) and mineralizing surface (MS/BS. However, the osteoblast surface (Ob.S/BS) (a reliable indicator of osteoblast population) in Shn3$^{-/-}$ mice is comparable to WT mice. These data suggest that the increased rate of bone formation observed in the Shn3$^{-/-}$ mice is caused by a functional augmentation of the osteoblasts and not by an increase in the number of osteoblasts. Interestingly, the thickness of the osteoid layer was comparable between WT and Shn3$^{-/-}$ mice. Since Shn3$^{-/-}$ mice have a similar osteoid thickness but an increase in MAR when compared to WT control mice, the time between osteoid formation and onset of mineralization must be decreased in Shn3$^{-/-}$ mice. Therefore, the osteosclerotic phenotype present in Shn3$^{-/-}$ mice results from aberrant bone formation and mineralization.

Example 5

Altered In Vitro Activity of Shn3$^{-/-}$ Osteoblasts

To verify that the increased bone mass observed in Shn3$^{-/-}$ mice is the effect of dysregulated osteoblast activity, a series of in vitro experiments were conducted on primary osteoblasts derived from the calvariae of newborn Shn3$^{-/-}$ and WT mice. These ex vivo osteoblast cultures have been reported to consist mainly of osteoblast precursors and immature osteoblasts. When matured in culture, these osteoblasts possess the capacity to form mineralized nodules, which reflects the cells' ability to generate extracellular matrix (Ducy, P., et al. (1999). *Genes Dev* 13, 1025-1036; Yoshida, Y., et al. (2000). *Cell* 103, 1085-1097). When Shn3$^{-/-}$ and WT osteoblast cultures were examined by von Kossa staining at days 0 and 5 for the presence of mineralized matrix, it was found that Shn3$^{-/-}$ cultures have an increased number of mineralized bone nodules. Furthermore, the mineralized nodules formed in the Shn3$^{-/-}$ osteoblast cultures were generally larger when compared to the mineralized nodules formed in the WT osteoblast cultures. The increased mineralized matrix present within Shn3$^{-/-}$ cultures did not result from these cultures containing an increased number of osteoblasts as WT and Shn3$^{-/-}$ cultures had a similar number of alkaline phosphatase (ALP) positive cells and displayed similar rates of cellular proliferation. The increased activity by the Shn3$^{-/-}$ osteoblasts in vitro correlates with the Shn3$^{-/-}$ mice exhibiting an increased BFR in vivo, and further demonstrates that dysregulated osteoblast activity is responsible for the observed phenotype.

The increase in mineralized nodule formation by Shn3$^{-/-}$ osteoblasts may result from alterations in the expression of genes involved in osteogenesis. Analysis of gene transcription by quantitative real-time PCR (Q-PCR) revealed Shn3$^{-/-}$ osteoblasts to express enhanced levels of BSP, ColI($\alpha$)1, and OCN mRNA but similar levels of ALP mRNA when compared to WT osteoblasts. ATF4, a key regulator of osteoblast biology (Yang, X., et al. (2004). *Cell* 117, 387-398), was also elevated in Shn3$^{-/-}$ osteoblasts at both the mRNA and protein level. Additionally, Shn3 itself was upregulated during osteoblast differentiation in vitro, further highlighting an osteoblast-intrinsic role for Shn3. Therefore, Shn3 regulates the expression of a number of genes that are important in bone formation and mineralization.

Example 6

Shn3 Regulates Runx2 Protein Stability through a Direct Interaction

Since the osteoblast-specific genes that were overexpressed in Shn3$^{-/-}$ osteoblasts are all direct targets of the transcription factor Runx2 (Stein, G. S., et al. (2004). *Oncogene* 23, 4315-4329; Yang, X., et al. (2004). *Cell* 117, 387-398), Shn3 may exert its inhibitory influence on osteoblast activity via an effect on Runx2 itself. Accordingly, levels of Runx2 mRNA and protein were quantitating in Shn3$^{-/-}$ and WT osteoblasts. Interestingly, Shn3$^{-/-}$ osteoblasts showed elevated levels of Runx2 protein even though levels of Runx2 mRNA were comparable between Shn3$^{-/-}$ and WT osteoblasts. This led to the question of whether Shn3 may regulate Runx2 protein stability. When overexpressed in 293T cells, Shn3 led to a dose-dependent decrease in steady-state Runx2 levels. Furthermore, overexpression of Shn3 led to accelerated degradation kinetics of overexpressed Runx2, as judged by pulse-chase experiments.

A number of possible mechanisms whereby Shn3 promotes Runx2 degradation can be envisioned, and the relationship between Shn3, Runx2, and TGF-β was investigated for the following reasons. First, in vivo overexpression of TGF-β in bone leads to osteoporosis (Erlebacher, A., and Derynck, R. (1996). *J Cell Biol* 132, 195-210; Erlebacher, A., et al. (1998). *Mol Biol Cell* 9, 1903-1918), while osteoblast-specific overexpression of a dominant-negative TGFβR leads to increased trabecular bone mass (Filvaroff, E., et al. (1999). *Development* 126, 4267-4279) similar to that observed in Shn3$^{-/-}$ mice. Second, it has been previously observed, that similar to the binding of Shn to Mad in *Drosophila*, Shn3 could directly interact with R-Smad proteins, most notably the TGF-β-dependent R-Smad, Smad3. Third, a well-documented binding partner of Runx2 is Smad3 (Alliston, T., et al. (2001). *Embo J* 20, 2254-2272; Ito, Y., and Zhang, Y. W. (2001). *J Bone Miner Metab* 19, 188-194; Sowa, H., et al. (2004). *J Biol Chem* 279, 40267-40275).

It was therefore reasoned that Shn3 regulates Runx2 protein stability by physical interaction. Indeed, Runx2 specifically co-immunoprecipitated Shn3 in cotransfection studies, and this interaction was mediated via the Runt (DNA binding) domain of Runx2. Additionally, it was possible to detect an interaction between endogenous Runx2 and Shn3 in MC3T3-E1 osteoblastic cells further differentiated into mature osteoblasts with ascorbic acid, β-glycerophosphate, and BMP-2 (Zamurovic, N., et al. (2004). *J Biol Chem* 279, 37704-37715). Although low levels of Shn3/Runx2 association were detected in cells following differentiation, treating the differentiated cells with TGF-β dramatically enhanced the association between Runx2 and Shn3.

To determine the consequences of the Runx2/Shn3 interaction with respect to Runx2 function, the Osteocalcin promoter, a well-characterized Runx2-binding site termed OSE2 (Ducy, P., et al. (1997). *Cell* 89, 747-754), was utilized. While Runx2 potently activated transcription from a multimerized OSE2-luciferase reporter construct, co-expression of Shn3 dose-dependently inhibited Runx2 activity. Co-treatment of cells with TGF-β, or co-expression of Smad3 further augmented Shn3's inhibitory effects towards Runx2. From these studies, it is concluded that Shn3 physically associates with Runx2, this association is promoted by TGF-β signaling, and Shn3 can inhibit Runx2 function in the context of this TGF-β-inducible complex.

Example 7

Shn3 Promotes the Ubiquitination of Runx2

Since it was demonstrated that Shn3 associates with and promotes the degradation of Runx2, it was determined whether Shn3 could promote the ubiquitination of Runx2. In overexpression studies, Shn3 promoted Runx2 ubiquitination. Furthermore, when Shn3/Runx2 complexes were immunopurified from 293T cells and used in in vitro ubiquitination assays, specific ubiquitin ligase activity was detected.

Although Shn3 promoted the ubiquitination of Runx2, Shn3 itself contains no canonical E3 ubiquitin ligase domains (RING, HECT, or U box, for review see, Patterson, C. (2002). *Sci STKE* 2002, PE4; Pickart, C. M. (2001). *Annu Rev Biochem* 70, 503-533,). Additionally, various recombinant protein fragments of Shn3 possessed no detectable in vitro E3 ubiquitin ligase activity. These observations led to the hypothesis that Shn3 may associate with a known E3 ubiquitin ligase to promote Runx2 ubiquitination. It has previously been demonstrated that Runx2 could be ubiquitinated by Smurf1 (Zhao, M., et al. (2004). *J Biol Chem* 279, 12854-12859; Zhao, M., et al. (2003). *J Biol Chem* 278, 27939-27944). Smurf1 belongs to a family of HECT domain-containing E3 ligases termed the Nedd4 family, all of which possess N-terminal C2 domains for membrane targeting, internal WW domains responsible for recognition of substrates with PPXY motifs, and C-terminal HECT E3 ligase domains (Ingham, R. J., et al. (2004). *Oncogene* 23, 1972-1984).

Although a physical interaction between Shn3 and Smurf1 was not detected, Shn3 did co-immunoprecipitate another member of the Nedd4 family of E3 ubiquitin ligases, WWP1. WWP1 has previously been shown to interact with all R- and I-Smad proteins, and to promote the ubiquitination of Smad6 and Smad7 (Komuro, A., et al. (2004). *Oncogene* 23, 6914-6923); however, the ability of WWP1 to ubiquitinate Runx proteins, which also possess PPXY motifs in their Runt domains (Jin, Y. H., et al. (2004). *J Biol Chem* 279, 29409-29417), had not been investigated. It was observed that WWP1 promoted low levels of Runx2 ubiquitination when overexpressed in 293T cells. However, when WWP1 was coexpressed with Shn3, the two synergistically acted to promote Runx2 ubiquitination.

Although not wishing to be bound by theory, these data suggest a model in which TGF-β signaling in osteoblasts promotes the formation of a multimeric complex between Runx2, Smad3, Shn3, and the E3 ubiquitin ligase WWP1. This complex inhibits Runx2 function due to the ability of WWP1 to promote Runx2 polyubiquitination and proteasome-dependent degradation. Shn3 is an integral component of this complex, since in its absence osteoblasts show elevated levels of Runx2 protein, enhanced Runx2 transcriptional activity, elevated transcription of Runx2 target genes, and increased bone formation in vivo. Signaling through the TGFβ receptor expressed on the surface of osteoblasts results in Smad3 complexing with Smad4 and translocating to the nucleus. Shn3, through its interaction with Smad3, associates with this complex in the nucleus to repress the transcription of genes involved in bone matrix biosynthesis. The nuclear Shn3/Smad complex further associates with WWP1, a HECT-domain containing E3 ligase. This complex interacts with and promotes the ubiquitination of Runx2, a key transcriptional regulator of genes involved in osteoblast differentiation and extracellular matrix biosynthesis. The ubiquitination of Runx2 by the Smad/Shn3/WWP1 complex targets Runx2 for proteosome-mediated degradation and/or the ubiquitination of Runx2 inhibits the transcriptional activity of this protein.

Example 8

Defective Osteoclastogenesis Occurs in Shn3$^{-/-}$ Mice In Vivo

A component of the high bone mass phenotype observed in our Shn3-deficient mice is clearly due to increased osteoblast matrix synthetic activity. In addition to their ability to synthesize and direct the mineralization of bone matrix, osteoblasts are known to produce RANKL, the critical cytokine known to induce osteoclastogenesis in vivo (Teitelbaum and Ross (2003) *Nat Rev Genet.* 4(8):63849). To determine if defective osteoclastogenesis in vivo may account for the osteosclerotic phenotype observed in our Shn3−/− strain, neonatal calvarial whole mount preparations were stained in situ for TRAP, a specific marker of mature osteoclasts. Decreased numbers of TRAP-positive cells in Shn3-deficient skulls, indicating decreased osteoclastogenesis in vivo. RANKL mRNA levels from whole bone or from calvarial osteoblast cultures were analyzed. Shn3-deficient osteoblasts show reduced levels of RANKL transcripts throughout the course of in vitro differentiation. Therefore, although hyperactive osteoblast matrix synthesis contributes to the elevated bone formation rates observed in vivo, the pronounced elevation in overall bone mass may due to both increased osteoblast activity and defective osteoclastogenesis in vivo.

Example 9

TGFβ Requires SHN3 to Reduce Bone Mass In Vivo

In the model organism *Drosophila*, the Schnurri gene is known to function in the Decapentaplegic (Dpp) signaling pathway. A mammalian homologue of the Dpp cytokine is the pleiotropic signaling molecule Transforming Growth Factor-β (TGFβ). Since SHN3 (also called KRC) is a mammalian homologue of *Drosophila* Schnurri, it was determined whether the ability of SHN3 to antagonize bone formation is downstream of TGFβ.

Previous studies have suggested an important role for TGFβ in skeletal biology. Mice overexpressing activated TGFβ in bone (termed D4 mice) display a dramatic osteopenia with reductions in mineralized trabecular bone, disorganized and hypercellular cortical bone, and spontaneous fractures (Erlebacher, et al. (1998) *Mol Biol Cell.* 9(7):1903-18)).

It had previously been reported that TGFβ signaling protein Smad3 binds and inhibits Runx2-mediated gene expression in osteoblasts (Alliston, et al. (2001) *EMBO J.* 20(9): 2254-72; Kang, et al. (2005) *EMBO J.* 24(14): 2543-2555). To determine if TGFβ requires SHN3 to reduce bone mass in vivo, 293T cells were transfected with Shn3 along with FLAG-tagged versions of Smad1-8. Forty-eight hours later, cells were harvested followed by anti-FLAG immunoprecipitations. Bound proteins were resolved by SDS-PAGE and immunoblotted for Shn3 or FLAG. The results show that SHN3 can interact with Smad3 proteins.

Moreover, the interaction between SHN3 and Runx2 was promoted by TGFβ. It was therefore determined whether SHN3 is downstream of TGFβ in vivo. Indeed, while D4 mice on a wild type background show the aforementioned skeletal abnormalities, D4 SHN3−/− mice show a pronounced rescue of trabecular bone mass, as well as more organized cortical bone and reduced spontaneous fractures. Therefore, SHN3 is required for the ability of TGFβ to reduce bone mass in vivo.

Example 10

Shn3 Regulates RSK2Function Through a Direct Interaction

An outstanding question is whether substrates for the SHN3/WWP1 ubiquitin ligase complex other than Runx2 exist. The possibility that the RSK2/ATF4 pathway is directly regulated by SHN3/WWP1 was investigated for the following reasons: (1) ATF4 is a transcription factor required for high levels of collagen synthesis by mature osteoblasts; (2) RSK2 is a kinase known to phosphorylate ATF4 that is required for optimal extracellular matrix production by osteoblasts (Yang, et al. (2004) *Cell.* 117(3):387-98.); (3) SHN3−/− osteoblasts show elevated levels of ATF4 mRNA and protein, as well as an accumulation of hyperphosphorylated ATF4.

Indeed, just as SHN3 overexpression inhibits Runx2-driven transcription in reporter assays, SHN3 overexpression inhibits ATF4-driven transcription as well as RSK2-mediated potentiation of ATF4 function. SHN3 and WWP1 do not physically associate with ATF4 protein, but both readily co-immunoprecipitate with RSK2. WWP1 can promote low levels of RSK2 ubiquitination. Additionally, both SHN3 and WWP1 can inhibit RSK2 function in in vitro kinase assays.

Importantly, levels of RSK2 autophosphorylation are increased in SHN3−/− osteoblasts, and increased immunoreactivity of several protein species detectable with a phosphospecific anti-RSK substrate antibody are detected in SHN3−/− osteoblasts. Interestingly, although ATF4 is thought to be an important substrate for RSK2 in wild type osteoblasts, SHN3−/−ATF4−/− mice show increased trabecular bone volumes comparable to SHN3−/− mice, suggesting that RSK2 substrates other than ATF4 play an important role in the increased bone formation seen in SHN3−/− mice.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of identifying compounds useful in modulating bone formation and mineralization comprising,
   a) providing an indicator composition comprising recombinant KRC;
   b) contacting the indicator composition with each member of a library of test compounds;
   c) selecting from the library of test compounds a compound of interest that modulates a biological activity of KRC, wherein the biological activity of KRC is selected from the group consisting of modulation of osteocalcin gene transcription, modulation of Runx2 degradation, modulation of Runx2 ubiquitination, modulation of RSK2 expression, modulation of RSK2 degradation, modulation of RSK2 ubiquitination, modulation of RSK2 phosphorylation, modulation of the expression of BSP, ColI(α)1, OCN, Osterix, RANKL, and/or ATF4, modulation of ATF4 protein levels, and/or modulation of ATF4 phosphorylation;
   d) testing the ability of the compound selected in step c) to modulate bone formation and mineralization; and
   e) selecting a compound that modulates bone formation or mineralization to thereby identify a compound useful in modulating bone formation and mineralization.

2. A method of identifying compounds useful in modulating bone formation and mineralization comprising,
   a) providing an indicator composition comprising recombinant KRC;
   b) contacting the indicator composition with each member of a library of test compounds;
   c) selecting from the library of test compounds a compound of interest that modulates a biological activity of KRC, wherein the indicator composition further comprises Runx2 and the ability of the compound to modulate a biological activity of KRC is measured by testing the ability of the compound to modulate the interaction of KRC and Runx2;
   d) testing the ability of the compound selected in step c) to modulate bone formation and mineralization; and
   e) selecting a compound that modulates bone formation or mineralization to thereby identify a compound useful in modulating bone formation and mineralization.

3. The method of claim 2, wherein the indicator composition is a cell comprising a KRC polypeptide and a Runx2 polypeptide.

4. The method of claim 2, wherein the indicator composition is a cell comprising a KRC polypeptide, a Runx2 polypeptide or transcriptionally active portion thereof, and a reporter gene responsive to the Runx2 polypeptide; and the effect of the test compound on the ability of the compound to modulate the interaction of KRC and Runx2 is determined by evaluating the expression of the reporter gene in the presence and absence of the test compound.

5. The method of claim 2, wherein a SMAD3 molecule is also present in the indicator composition.

6. The method of claim 2, wherein the indicator composition further comprises CBFβ and the compound modulates the interaction of Runx2 and CBFβ.

7. A method of identifying compounds useful in modulating bone formation and mineralization comprising,
   a) providing an indicator composition comprising recombinant KRC;
   b) contacting the indicator composition with each member of a library of test compounds;
   c) selecting from the library of test compounds a compound of interest that modulates a biological activity of KRC, wherein the indicator composition further comprises recombinant WWP1 and the ability of the compound to modulate a biological activity of KRC is measured by testing the ability of the compound to modulate the interaction of KRC and WWP1;
   d) testing the ability of the compound selected in step c) to modulate bone formation and mineralization; and
   e) selecting a compound that modulates bone formation or mineralization to thereby identify a compound useful in modulating bone formation and mineralization.

8. The method of claim 7, wherein a Runx2 molecule, or transcriptionally active portion thereof, is also present in the indicator composition.

9. The method of claim 7, wherein a RSK2 molecule is also present in the indicator composition.

* * * * *